United States Patent
Hielscher et al.

(10) Patent No.: US 9,495,516 B2
(45) Date of Patent: Nov. 15, 2016

(54) SYSTEMS, METHODS, AND DEVICES FOR IMAGE RECONSTRUCTION USING COMBINED PDE-CONSTRAINED AND SIMPLIFIED SPHERICAL HARMONICS ALGORITHM

(71) Applicant: The Trustees of Columbia University in the City of New York, New York, NY (US)

(72) Inventors: Andreas H. Hielscher, Brooklyn, NY (US); Hyun Keol Kim, Cresskill, NJ (US); Ludguier D. Montejo, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/441,730
(22) PCT Filed: Nov. 21, 2013
(86) PCT No.: PCT/US2013/071269
§ 371 (c)(1),
(2) Date: May 8, 2015
(87) PCT Pub. No.: WO2014/081945
PCT Pub. Date: May 30, 2014

(65) Prior Publication Data
US 2015/0286785 A1     Oct. 8, 2015

Related U.S. Application Data

(60) Provisional application No. 61/737,975, filed on Dec. 17, 2012, provisional application No. 61/729,536, filed on Nov. 23, 2012, provisional application No. 61/729,255, filed on Nov. 21, 2012.

(51) Int. Cl.
*G06K 9/00*     (2006.01)
*G06F 19/00*     (2011.01)
(Continued)

(52) U.S. Cl.
CPC ........... *G06F 19/345* (2013.01); *A61B 5/0073* (2013.01); *G06K 9/00127* (2013.01);
(Continued)

(58) Field of Classification Search
None
See application file for complete search history.

(56) References Cited

U.S. PATENT DOCUMENTS 6,687,010 B1    2/2004    Horii et al.
8,190,245 B2    5/2012    Mitra
(Continued)

FOREIGN PATENT DOCUMENTS

WO    WO 2006/128889    12/2006
WO    WO 2011/137247    11/2011
(Continued)

OTHER PUBLICATIONS

Kim et al (NPL: "A PDE-contrained SQP algorthim for optical tomography based on the frequency-domain equation of radiative transfer", Department of Biomedical Engineering, Columbia University, Inverse Problems 25 (2009) 015010 (20pp, hereafter referred to as Kim).*

(Continued)

*Primary Examiner* — Bhavesh Mehta
*Assistant Examiner* — Oneal R Mistry
(74) *Attorney, Agent, or Firm* — Potomac Law Group, PLLC; Mark Catan

(57) ABSTRACT

Systems, methods, and devices for image reconstruction using combined PDE-constrained and simplified spherical harmonics (SPN) algorithm are presented herein. SPN equations can be used as the forward model in diffuse optical tomography (DOT) and employed in a PDE-constrained reduced space sequential quadratic programming (rSQP) optimization method to reconstruct spatially distributed optical properties, such as absorption, scattering, fat, oxygenated hemoglobin, de-oxygenated hemoglobin, fluorescent concentration, quantum yield, etc. The SPN algorithm with the PDE-constrained rSQP optimization method allows for DOT imaging that uses significantly less computational resources (e.g., time and random-access memory (RAM)) than methods employing the equation of radiative transfer (ERT). The techniques disclosed herein allow for more expeditious image processing as well as the potential for clinical diagnosis using DOT imaging. Diagnosis can be performed by a computer-aided diagnosis (CAD) system, which can provide clinically relevant analysis and interaction shortly after patient imaging.

17 Claims, 30 Drawing Sheets

(51) Int. Cl.
- A61B 5/00 (2006.01)
- G06T 7/00 (2006.01)
- G06K 9/46 (2006.01)
- G06T 11/00 (2006.01)

(52) U.S. Cl.
CPC .......... *G06K9/4661* (2013.01); *G06T 7/0012* (2013.01); *G06T 11/006* (2013.01); *G06T 2207/10101* (2013.01); *G06T 2207/20081* (2013.01); *G06T 2207/30004* (2013.01); *G06T 2207/30008* (2013.01)

(56) References Cited

U.S. PATENT DOCUMENTS

| | | | |
|---|---|---|---|
| 8,194,072 | B2 | 6/2012 | Jones et al. |
| 8,254,023 | B2 | 8/2012 | Watson et al. |
| 8,294,901 | B2 | 10/2012 | Yoshida et al. |
| 2002/0041710 | A1 | 4/2002 | Magarcy et al. |
| 2004/0052328 | A1* | 3/2004 | Sabol ............ G06T 7/0012 378/37 |
| 2007/0081725 | A1* | 4/2007 | Hong ............. G06T 7/0083 382/173 |
| 2010/0292569 | A1 | 11/2010 | Hielscher et al. |
| 2013/0066219 | A1* | 3/2013 | Jiang ............ A61B 5/026 600/504 |
| 2013/0289394 | A1 | 10/2013 | Hielscher et al. |

FOREIGN PATENT DOCUMENTS

| | | |
|---|---|---|
| WO | WO 2012/065140 | 5/2012 |
| WO | WO 2012/082789 | 6/2012 |
| WO | WO 2012/082804 | 6/2012 |
| WO | WO 2013/070923 | 5/2013 |
| WO | WO 2013/070982 | 5/2013 |

OTHER PUBLICATIONS

Sanchez et al ("Evaluation of a Computer Aided Diagnosis System for Diabetic Retinopathy Screening of Public Data", Investigative Ophthalmology & Visual Science, Jun. 2011, vol. 52, No. 7 4866 Copyright 2011 The Association for Research in Vision and Ophthalmology, Inc.).*

Guina et al (NPL: "Light-Emitting Diode Emitting at 650 nm with 200 MHz Small-Signal Modulation Bandwidth", IEEE Photonics Technology Letters, vol. 12, No. 7, Jul. 2000.).*

Cygler et al (NPL: "MOSFET dosimetry in radiotherapy", The Ottawa Hospital Regional Cancer Centre, p. 51).*

The PC Guide "How much RAM P4 3GHz Support" p. 3.*

Intel 845 Chipset Family Motherboard, Intel 2001, p. 52.*

Boas et al., "Imaging the body with diffuse optical tomography," *IEEE Signal Processing Magazine*, 2001, 18(6): pp. 57-75.

Bouza Dominguez et al., "Diffuse optical tomographic imaging of biological media by time-dependent parabolic SPN equations: a two-dimensional study," *Journal of Biomedical Optics*, Aug. 2012, 17(8): 086012.

Dehgahi et al., "Numerical modeling and image reconstruction in diffuse optical tomography," *Philosophical Transactions of the Royal Society A*, 2009, 367(1900): pp. 3073-3093.

International Search Report and Written Opinion, mailed Apr. 21, 2014, for International Application No. PCT/US13/71269.

Kim et al., "A PDE-constrained SQP algorithm for optical tomography based on the frequency-domain equation of radiative transfer," *Inverse Problems*, 2009, 25(015010): pp. 1-20.

Klose et al., "Investigations of RA-diagnostics applying optical tomography in frequency-domain," *Proceedings of the SPIE*, 1998, 3196: pp. 194-205.

Klose et al., "Light transport in biological tissue based on the simplified spherical harmonics equations," *Journal of Computational Physics*, Sep. 2006, 220: pp. 441-470.

Montejo et al., "A finite-volume algorithm for modeling light transport with the time-independent simplified spherical harmonics approximation to the equation of radiative transfer," *Proceedings of the SPIE: Optical, Tomography and Spectroscopy of Tissue IX*, Feb. 2011, 7896(0J): pp. 1-6.

Zhai et al., "Fast tomographic reconstruction strategy for diffuse optical tomography," *Optics Express*, 2009, 17(7): pp. 5285-5297.

* cited by examiner

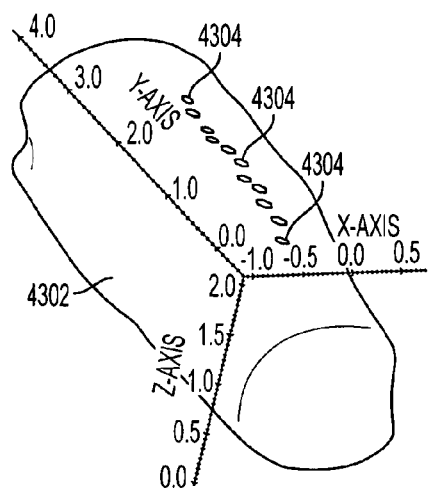
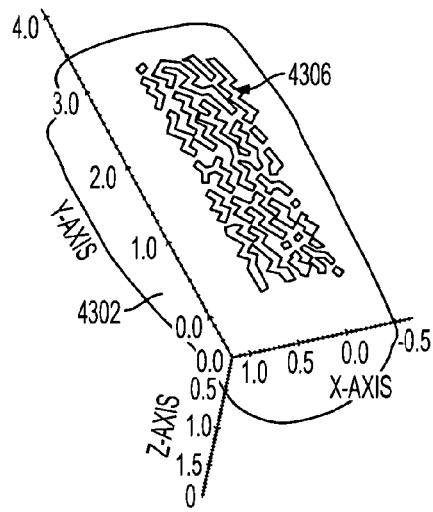
FIG. 43A  FIG. 43B
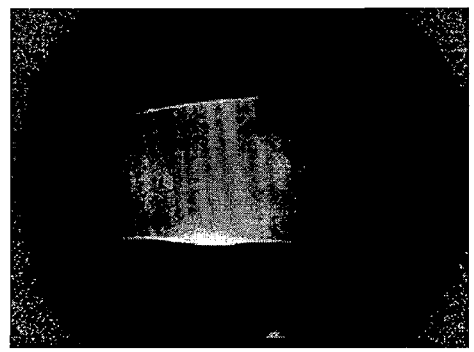
FIG. 44A  FIG. 44B
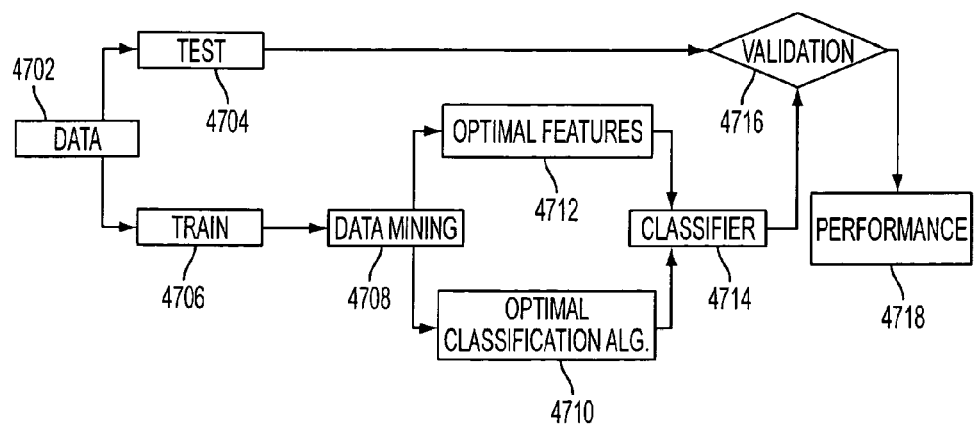
FIG. 47

SYSTEMS, METHODS, AND DEVICES FOR IMAGE RECONSTRUCTION USING COMBINED PDE-CONSTRAINED AND SIMPLIFIED SPHERICAL HARMONICS ALGORITHM

CROSS-REFERENCE TO RELATED APPLICATIONS

The present application claims the benefit of U.S. Provisional Application No. 61/729,255, filed Nov. 21, 2012, U.S. Provisional Application No. 61/729,536, filed Nov. 23, 2012, and U.S. Provisional Application No. 61/737,975, filed Dec. 17, 2012, all of which are hereby incorporated by reference herein in their entireties.

FIELD

The present disclosure relates generally to optical tomographic imaging, and, more particularly, to image reconstruction employing a combination of partial differential equation (PDE) constrained and simplified spherical harmonics (SPN) algorithms.

BACKGROUND

Diffuse optical tomography (DOT) imaging can be used as a medical imaging modality where near-infrared (NIR) photons are used to probe tissue. NIR photons are injected into the tissue of interest, for example by focusing a non-invasive NIR laser onto the tissue surface. The NIR photons interact with the underlying physiology. The interactions result in absorption or scattering events, i.e., NIR photons are either annihilated or redirected from their incoming direction, respectively. Scattered photons may eventually escape the tissue of interest. Information gathered from these exiting photons can be used to reconstruct the spatial distribution of physiologically relevant parameters such as tissue absorption and scattering coefficients, concentration of oxygenated and deoxygenated hemoglobin, and concentration of fluorescent and bioluminescent probes. Thus, DOT imaging can be used as tool for monitoring and detecting physiological processes and pathologies.

An application of DOT imaging can be the diagnosis of rheumatoid arthritis (RA) through imaging of finger joints. As compared to other anatomical features, fingers are relatively small, and so the intensity of light transmitted through the fingers can be relatively high, thereby allowing for simple signal detection. Additionally, the scattering properties of the synovial fluid inside the joints changes as a result of the onset of RA. Thus, the optical contrast between healthy joints and joints with RA can be used in the DOT diagnosis of RA.

DOT data acquisition of a structure such as a finger can take on the order of 15 minutes, for example. However, the computational time required to obtain the optical properties of finger joints remains considerably long (e.g., on the order of 3 hours or more per finger). Indeed, computation time can be much longer than 3 hours, depending on the numerical accuracy of the light models employed. Computation times on the order of 12 hours per finger are not unheard of. Moreover, the processing of the DOT data can require significant computational resources (e.g., on the order of 6 GB of RAM or more per finger) that severely limit the practical use of this modality.

A primary factor affecting computation time is the selection of algorithms employed in image reconstruction. In particular, the equation of radiative transfer (ERT) is typically used for modeling light propagation in finger joints because it is the most accurate deterministic model of light propagation in small volumes. Although they are accurate, the ERT-based reconstruction algorithms are also highly complex and require substantial computational resources, thereby increasing the computation time and system requirements necessary to perform such an analysis.

SUMMARY

Systems, methods, and devices for image reconstruction using combined partial differential equation (PDE)-constrained and simplified spherical harmonics (SPN) algorithm are presented herein. SPN equations can be used as the forward model in diffuse optical tomography (DOT) and employed in a PDE-constrained reduced space sequential quadratic programming (rSQP) optimization method to reconstruct spatially distributed optical properties, such as absorption, scattering, fat, oxygenated hemoglobin, de-oxygenated hemoglobin, fluorescent concentration, quantum yield, etc. The use of the SPN algorithm with the PDE-constrained rSQP optimization method allows for DOT imaging that uses significantly less computational resources (e.g., time and random-access memory (RAM)) than other approaches, such as the equation of radiative transfer (ERT). The techniques disclosed herein allows for more expeditious image processing as well as the potential for clinical diagnosis using DOT imaging.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some features may not be illustrated to assist in the illustration and description of underlying features. Throughout the figures, like reference numerals denote like elements.

FIGS. 43A-43B show the locations of sources and detectors on a finger section including a PIP joint, according to one or more embodiments of the disclosed subject matter.

FIGS. 44A-44B are transillumination images captured by a detector unit on a posterior surface of a PIP joint belonging to a subject with RA and a health subject, respectively, according to one or more embodiments of the disclosed subject matter.

FIG. 47 is a process flow chart of an exemplary method for cross-validation, according to one or more embodiments of the disclosed subject matter.

DETAILED DESCRIPTION

Figure 1:
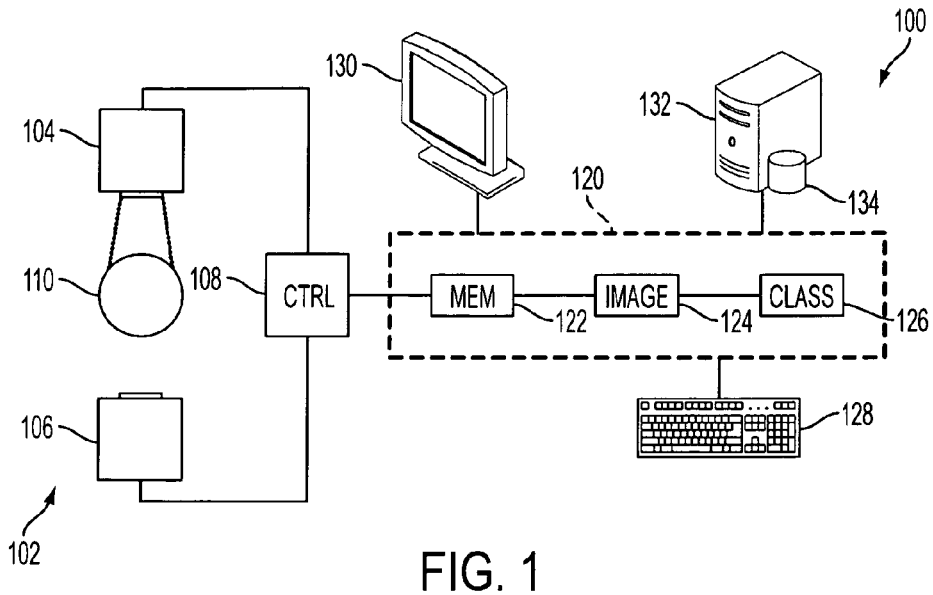
FIG. 1 is a diagram showing features of a computer aided diagnostic system, according to one or more embodiments of the disclosed subject matter.

Simplified spherical harmonics (SPN) can be used to approximate the process of light propagation in biological tissue (it approximates the average photon-tissue interaction). The SPN equations are derived from the more general equation of radiate transfer (ERT). While the ERT model is known to work best compared to all other deterministic models (i.e., diffusion approximation and SPN approximations), it is computationally expensive to use. Frequency-domain (FD) SPN equations can be used as the forward model in optical tomography and employed in a PDE-constrained reduced space sequential quadratic programming (rSQP) optimization method to reconstruct spatially distributed optical properties (such as absorption, scattering, fat, oxygenated hemoglobin, de-oxygenated hemoglobin, fluorescent concentration, quantum yield, etc.) by employing significantly less computational resources (e.g., time and random-access memory (RAM)) than the ERT approach.

The general method of SPN allows an approximate solution of arbitrary order of accuracy to be obtained by transforming the original governing equation into a set of simultaneous partial differential equations. Therefore, the greatest advantage of using the SPN method is the conversion of an integro-differential equation of radiative transfer into relatively simple partial differential equations. However, the orthogonality properties of SPN can lead to infinitely many coupled equations, so only low-order approximations (e.g., $SP_1$, $SP_3$, $SP_5$, $SP_7$, and so on) may be practical.

The SPN model of low-order approximations can be used with a PDE-constrained optimization algorithm. The SPN equations, which are an approximation to the ERT, are strongly coupled with each other, and this coupling may be accurately taken into account within the framework of PDE-constrained optimization. Another computation aspect specific to this SPN-based PDE-constrained optimization is that stable convergence and computational speedup are guaranteed as in the ERT-based PDE-constrained method by employing a safeguard called "self-correcting second-order corrections."

Compared to using a FD-ERT rSQP algorithm, the FD-SPN rSQP algorithm may yield optical tomographic results of similar accuracy but at significantly reduced computational cost. For example, solving the FD-ERT forward model on a medium of 10,000 mesh elements (10,000 "unknowns") with S8 discrete ordinates angular discretization (80 discrete angles per mesh element) results in a forward system of 800,000 unknowns. Comparatively, an SP3 equations on the same mesh results in only 20,000 unknowns in the forward model with only moderate losses in accuracy for optical regimes commonly encountered in analyzing biological structures and appendages, for example, the breast, fingers, etc. The savings in computational speed obtained from the forward model (e.g., by using the FD-SPN instead of the FD-ERT model) translates to substantial computational savings in the PDE-constrained rSQP based reconstructions since the scheme solves the forward model throughout the optimization process.

Computer-aided diagnosis (CAD) can be performed using the images that result from solving optical tomography problems with the FD-SPN PDE-constrained rSQP algorithm. The classification (i.e., diagnostic) accuracy obtained with the SPN solutions may be similar to those obtained with the ERT equation, in terms of sensitivity and specificity, and can be obtained at significantly faster computational times. In particular, performing CAD with images obtained from the FD-SPN PDE-constrained rSQP algorithm may be attractive because the diagnostic accuracy is not significantly diminished (as compared to the ERT-based algorithms). Moreover, diagnosis can be achieved sooner after a subject is imaged since the reconstruction time using SPN algorithms described herein is much quicker than those employing a non-SPN PDE-constrained rSQP approach or a FD-ERT PDE-constrained rSQP approach.

FIG. 1 illustrates various exemplary aspects associated with a computer aided diagnostic (CAD) system 100 according to embodiments of the disclosed subject matter. CAD system 100 can include a diffuse optical tomography (DOT) imaging device 102, which has at least one illumination source 104 for illuminating a sample 110, such as, but not limited to, the finger of a patient, with near-infrared radiation. Illumination of the sample 110 can be modulated, for example, at a frequency in a range of 200 MHz to 800 MHz (e.g., 600 MHz). DOT imaging device 102 can also include one or more detectors 106, for example a CCD camera. Alternatively or additionally, detector 106 can include one or more waveguides, for example, optical fibers, for transmitting light exiting the sample 110 to a remote detection unit, for example, a photodiode or other sensor.

A control unit 108 can control operation of source 104 and detector 106, for example, by coordinating the illumination modulation and the detection. In addition, the control unit 108 can take the signals from detector 106 and convey them to data processing module 120. Data processing module 120 can receive data in raw form and process it as described herein for reconstruction and classification purposes. The optical tomographic data can be representative of the features of interrogated sample 110.

Processing module 120 can include a data storage 122 that receives the optical tomographic data from the control unit 108 and stores it therein for later or immediate use by processing module 120. The processing module 120 can also include an image processing module 124, which receives the optical tomographic data from the data storage 122. The image processing module 124 can be configured to estimate volumetric properties of the sample 110 by performing a PDE-constrained optimization, in which the constraint is defined by a simplified spherical harmonics approximation to the ERT. The properties can include at least one, or ones, of: volumetric absorption, volumetric scattering, volumetric fat distribution, volumetric distribution of oxygenated hemoglobin, and/or de-oxygenated hemoglobin, volumetric fluorophore concentration and/or distribution, and/or volumetric quantum yield.

The image processing module 124 can be configured to perform the optimization such that the inverse and forward problems are solved simultaneously and independently. The forward problem can be represented by solving a simplified spherical harmonics approximation to the ERT, with simplified spherical coefficients. The PDE-constrained optimization can include minimizing a Lagrangian function. The PDE-constrained optimization and the simplified spherical harmonics (SPN) approximation are discussed in further detail below. The image processing module 124 can have a single computing core or can have multiple computer cores, thereby allowing parallel processing of the disclosed algorithms. Because of the use of PDE-constrained optimization and the SPN approximation, computational resources can be reduced as compared to ERT-based reconstructions, and the image processing module 124 can operate with significantly less RAM in performing the reconstructions as compared to ERT-based methods. The combined SPN approximation with PDE-constrained optimization can thus be performed with at least ten (10) times less RAM (e.g., at least eighty (80) times less RAM) than would otherwise be required for an ERT-based reconstruction.

The processing module 120 can also include a classification module 126, which receives the reconstructed images from the image processing module 124. For example, the reconstructed images can include maps of scattering and absorption coefficients within the sample. Based on the reconstructed images, the classification module 126 can make a determination with respect to classification of the sample. For example, the classification module 126 can provide an indication of whether a patient has rheumatoid arthritis based on the reconstructed images and prior training data, as described in more detail below. Other classification applications are also possible according to one or more contemplated embodiments, and embodiments of the disclosed subject matter are not specifically limited to rheumatoid arthritis diagnosis. Embodiments of the disclosed subject matter may include the analysis and/or diagnosis of other diseases or conditions, such as, but not limited to, Dermatomyositis, Graves disease, Hashimoto's thyroiditis, Multiple sclerosis, Myasthenia gravis, Pernicious anemia, Reactive arthritis, Sjogren syndrome, Systemic lupus erythematosus, and Type I diabetes. Moreover, embodiments may further include the analysis of temporal and spatial-temporal images/data.

Processing module 120 can interact with a user through input/output devices, for example, keyboard 128, and can be configured to interact with remote devices, such as, server 132, which may include a database 134 of information for use in, for example, classification of features by classification module 126. The processing module 120 can output display data, for example, to a display 130. The display data can include classification data representing the volumetric properties of sample 110 or a classification of the features of the sample 110. For example, display 130 can provide an indication of whether a patient has rheumatoid arthritis.

The system 100 can be configured to allow a user, for example, a physician or other medical service provider, to interact with the system 100 before, during, or after image reconstruction. For example, a user can view image reconstruction data on display 130 and can interact with processing module 120 via input/output device 128. The user may select areas of interest from which some or all of additional features can be extracted so that classification routine may be enhanced. Alternatively or additionally, DOT imaging device 102 can include a detector that images visible light, which image can be displayed by system 100 on display 130. The user may use the visible image to position the patient for subsequent DOT imaging by device 102, for example, by using visual on-screen markers on the display 130 or in an area. Prior to or during the image reconstruction, the user can select areas of interest on the visible light image for subsequent DOT interrogation and/or image reconstruction.

Although features or components illustrated in FIG. 1 are shown separately, it is also possible that the features or components can be combined together, separated, or rearranged to create additional features or components. For example, control unit 108 of DOT imaging device 102 and processing module 120 can be combined together in a single computer system. Alternatively, data storage device 122 can be incorporated together with the control unit 108 in a separate module. In still another alternative, processing module 120 can exist as a separate stand-alone unit from the DOT imaging device 102 and can be configured to receive data from imaging device 102 without a direct link, for example, by way of the Internet, portable memory storage device, or wirelessly. Moreover, features indicated as separate, for example, image processing module 124 and classification module 126, may be embodied by a single device performing both functions, for example, by a processor configured to perform said functions. Accordingly, aspects of the disclosed subject matter are not limited to the specific arrangement and grouping illustrated in FIG. 1

A finite volume (FV) approximation can be used for each of the FD-SPN models (FV-FDSPN). In particular, a node-centered FV discretization of the computational domain can be employed. The resulting system of linear algebraic equations can be solved with the restarted generalized minimal residual method (GMRES), which is a Krylov subspace iterative method for solving systems of linear equations and allows for improved computational efficiency. The algorithm can be implemented, for example, using objective-oriented programming in C++. Such an approach to solving the FD-SPN equations as applied to DOT imaging is attractive because the node-centered finite volume method (FVM) takes advantage of the beneficial properties associated with the finite-element method (FEM) and the standard FVM technique. It combines the conservation properties of the FVM formulation and the geometric flexibility of the FEM approach.

Furthermore, the FVM implementation described herein is advantageous over the finite differences method (FDM), where the computational space is discretized with Cartesian grids, because it can be easily formulated on unstructured grids to accommodate geometries of arbitrary shape. Such properties can be advantageous for DOT applications, which often involve the imaging of complex geometries (e.g., mice, fingers, etc.) that can be most accurately modeled by unstructured grids.

Discussed below is a framework for the implementation of an algorithm that solves the FV-FD-SPN equations. The FV-FD-SPN algorithm can be implemented in, for example, C++ programming language, and may be computationally efficient, thereby requiring low system memory and converging to acceptable solutions significantly faster than other algorithms that may use unstructured grids. The algorithm can accurately model light propagation in geometries of arbitrary shape as the imaging object is discretized with unstructured grids. The algorithm can be validated through numerical simulations, for example, by using the ERT model as a benchmark.

Finite Volume Mesh

Figure 2A:
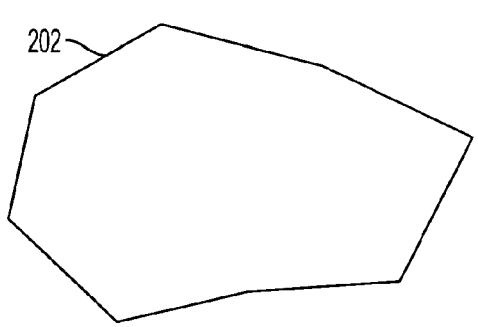
FIGS. 2A-2B show an example of a physical object and associated mesh discretization, respectively, according to one or more embodiments of the disclosed subject matter.
Figure 2B:
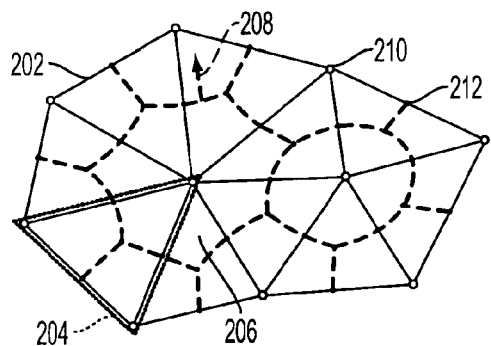

As shown in FIGS. 2A-2B, an imaging domain 202 can be discretized with a computational domain V, composed of linked unstructured Euclidean simplex elements. For example, these shapes can be triangles in two-dimensional space and/or tetrahedral in three-dimensional space. The discretized domain V can include M mesh nodes, where each mesh node $m (m \in M)$ is the center of a finite volume dV and there are M distinct finite volume elements. Thus, m refers to a specific mesh node and also to a specific finite volume element 206, as shown in FIG. 2B. Finite volume element m (e.g., 206) has $S_I$ internally facing surfaces (i.e., not on the surface of V) and $S_B$ boundary surfaces (i.e., on the surface of V). The mesh is referred to herein as an FEM mesh because it is used when solving systems of equations with an FEM algorithm.

Without loss of generality, consider a two-dimensional object discretized by triangular elements 204. When dealing with three-dimensional objects can be discretized using tetrahedral elements. FIG. 2A shows an example of a simple two-dimensional object 202. FIG. 2B shows the corresponding discretization of object 202 into an unstructured triangular FEM mesh (e.g., only one mesh element 204 is highlighted in FIG. 2B) with its corresponding unstructured FVM mesh superimposed (e.g., dashed lines in FIG. 2B). In an example, the object 202 can first be discretized into the unstructured triangular mesh, from which the FVM mesh can be subsequently computed.

The mesh conversion process refers to finding the dual FVM mesh (dashed lines) of the original FEM mesh (e.g., triangular elements 204). Each node 210 in the FEM mesh (e.g., open larger dots in FIG. 2B) becomes the center of an FVM element 206, which is surrounded with faces or edges (e.g., dashed lines) that are formed by the centers 212 (e.g., filled smaller dots in FIG. 2B) of edges, faces, and elements of the FEM mesh.

Figure 3A:
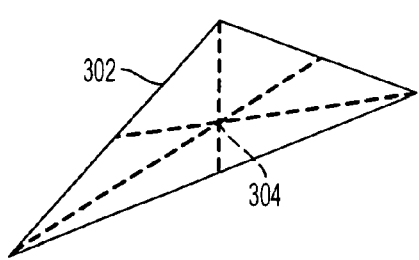
FIGS. 3A-3B show mesh element centers computed by the median and Delaunay methods, respectively, according to one or more embodiments of the disclosed subject matter.
Figure 3B:
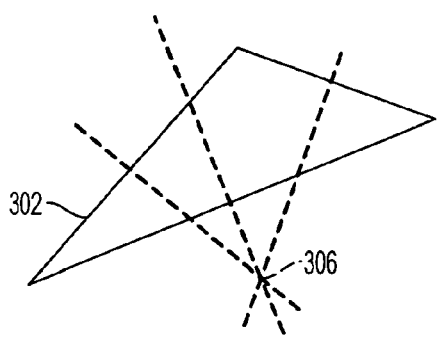

The FVM mesh can be obtained from an FEM mesh by using, for example, the "median" method or the "Delaunay" method. Both methods require knowledge of the center of each triangular element 204 in the FEM mesh and the centers of all its edges and faces (i.e., dots 212). However, each method has a specific way of defining the "center" of these geometries. In the median dual method, as shown in FIG. 3A, the centroid 304 of the edge, face, or element 302 is treated as its center point. In contrast, for the Delaunay dual method, as shown in FIG. 3B, the center of the circumsphere of the edge, face or element 302 is treated as the centerpoint 306.

The median dual method guarantees that the center of each FEM element is inside the simplex element, while this may not always be the case with the Delaunay method. Moreover, the Delaunay dual method has extra requirements on the geometry of the simplex elements. When these requirements are not met, the computed center of the simplex element may be outside the element itself, which can result in a poorly structured FVM mesh. FIG. 3B shows an example of a triangular element whose Delaunay center is located outside the element itself. Although embodiments described herein employ the median dual method, contemplated alternative embodiments can employ the Delaunay dual method or any other method.

Finite Volume FD-SPN Approximation

Described below is the FD-SP$_3$ model and the derivation of its finite volume formulation, according to one or more embodiments of the disclosed subject matter. Formulas for the finite volume form of other orders of the SPN models (i.e., N=1, 5, 7, etc.) can be derived by following similar procedures as described below, and thus are not discussed in detail herein. In addition, the derivation below is directed to FVM approximation to the FD-SP$_3$ (RD) model. Derivation of the FVM approximation for the FD-SP$_3$ (CD) model can follow the same framework, and thus are not discussed in detail herein. The FD-SP$_3$ (RD) and FD-SP$_3$ (CD) models are reproduced in Eqns. 8.1-8.2 and Eqns. 8.3-8.4, respectively, below.

$$-\nabla \cdot \frac{1}{3\mu_{a1}} \nabla \varphi_1 + \left(\mu_a + \frac{i\omega}{v}\right)\varphi_1 = Q + \frac{2}{3}\left(\mu_a + \frac{i\omega}{v}\right)\varphi_2 \qquad (8.1)$$

$$-\nabla \cdot \frac{1}{7\mu_{a3}} \nabla \varphi_2 + \left(\frac{4}{9}\mu_a + \frac{5}{9}\mu_{a2} + \frac{1}{3}\frac{i\omega}{v}\right)\varphi_2 = -\frac{2}{3}Q + \frac{2}{3}\mu_a\varphi_1 \qquad (8.2)$$

$$-\nabla \cdot \frac{1}{3\bar{\mu}_{a1}} \nabla \varphi_1 + \left(\mu_a + \frac{i\omega}{v}\right)\varphi_1 = Q + \frac{2}{3}\left(\mu_a + \frac{i\omega}{v}\right)\varphi_2 \qquad (8.3)$$

$$-\nabla \cdot \frac{1}{7\bar{\mu}_{a3}} \nabla \varphi_2 + \left(\frac{4}{9}\mu_a + \frac{5}{9}\bar{\mu}_{a2} + \frac{i\omega}{v}\right)\varphi_2 = -\frac{2}{3}Q + \frac{2}{3}\left(\mu_a + \frac{i\omega}{v}\right)\varphi_1 \qquad (8.4)$$

The composite moments $\phi_1 = \phi_1(r, w)$ and $\phi_2 = \phi_2(r, w)$ are functions of space and modulation frequency. The corresponding set of boundary equations for the FD-SP$_3$ (RD) and FD-SP$_3$ (CD) models are given by (8.5-8.6) and (8.7-8.8), respectively.

$$\left(\frac{1}{2} + A_1\right)\varphi_1 + \left(\frac{1+B_1}{3\mu_{a1}}\right)(\hat{n} \cdot \nabla \varphi_1) = \qquad (8.5)$$
$$\left(\frac{1}{8} + C_1\right)\varphi_2 + \left(\frac{D_1}{\mu_{a3}}\right)(\hat{n} \cdot \nabla \varphi_2) + \int_{\Omega \cdot \hat{n} < 0} S(\Omega) 2|\Omega \cdot \hat{n}| d\Omega,$$

$$\left(\frac{7}{24} + A_2\right)\varphi_2 + \left(\frac{1+B_2}{7\mu_{a3}}\right)(\hat{n} \cdot \nabla \varphi_2) = \qquad (8.6)$$
$$\left(\frac{1}{8} + C_2\right)\varphi_1 + \left(\frac{D_2}{\mu_{a1}}\right)(\hat{n} \cdot \nabla \varphi_1) + \int_{\Omega \cdot \hat{n} < 0} S(\Omega)(5|\Omega \cdot \hat{n}|^3 - 3|\Omega \cdot \hat{n}|) d\Omega.$$

-continued $$\left(\frac{1}{2}+A_1\right)\varphi_1+\left(\frac{1+B_1}{3\bar{\mu}_{a1}}\right)(\hat{n}\cdot\nabla\varphi_1)= \quad (8.7)$$
$$\left(\frac{1}{8}+C_1\right)\varphi_2+\left(\frac{D_1}{\bar{\mu}_{a3}}\right)(\hat{n}\cdot\nabla\varphi_2)+\int_{\Omega\cdot\hat{n}<0}S(\Omega)2|\Omega\cdot\hat{n}|d\Omega,$$

$$\left(\frac{7}{24}+A_2\right)\varphi_2+\left(\frac{1+B_2}{7\bar{\mu}_{a3}}\right)(\hat{n}\cdot\nabla\varphi_2)= \quad (8.8)$$
$$\left(\frac{1}{8}+C_2\right)\varphi_1+\left(\frac{D_2}{\bar{\mu}_{a1}}\right)(\hat{n}\cdot\nabla\varphi_1)+\int_{\Omega\cdot\hat{n}<0}S(\Omega)(5|\Omega\cdot\hat{n}|^3-3|\Omega\cdot\hat{n}|)d\Omega.$$

The definitions of the partial current, $J^+(r, w)$, at the boundary of the object for the FD-SP$_3$(RD) and FD-SP$_3$ (CD) models are given by Eqn. 8.9 and Eqn. 8.10, respectively.

$$J^+(r,\omega)\left(\frac{1}{4}+J_0\right)\left(\varphi_1-\frac{2}{3}\varphi_2\right)- \quad (8.9)$$
$$\left(\frac{0.5+J_1}{3\bar{\mu}_{a1}}\right)(\hat{n}\cdot\nabla\varphi_1)+\left(\frac{5}{16}+J_2\right)\left(\frac{1}{3}\varphi_2\right)-\left(\frac{J_3}{7\bar{\mu}_{a3}}\right)(\hat{n}\cdot\nabla\varphi_2).$$

$$J^+(r,\omega)\left(\frac{1}{4}+J_0\right)\left(\varphi_1-\frac{2}{3}\varphi_2\right)- \quad (8.10)$$
$$\left(\frac{0.5+J_1}{3\bar{\mu}_{a1}}\right)(\hat{n}\cdot\nabla\varphi_1)+\left(\frac{5}{16}+J_2\right)\left(\frac{1}{3}\varphi_2\right)-\left(\frac{J_3}{7\bar{\mu}_{a3}}\right)(\hat{n}\cdot\nabla\varphi_2).$$

The only difference between the FD-SP$_3$(RD) and FD-SP$_3$ (CD) models is the definition of the nth order absorption coefficient. The nth order absorption coefficients for the FD-SP$_3$(RD) model (i.e., Eqns. 8.1-8.2, 8.5-8.6 and 8.9) are given by $\mu_{an}=\mu_a+(1-g^n)\mu_s$. For the FD-SP$_3$(CD) model (i.e., Eqns. 8.3-8.4, 8.7-8.8, and 8.10) the coefficients are given by $$\bar{\mu}_{an}=\mu_a+(1-g^n)\mu_s+\frac{i\omega}{v}.$$

The fluence, $\phi_n$, is computed from the individual composite moments of the SPN model and is given by:

$$\phi_0=\varphi_1-\frac{2}{3}\varphi_2, \quad (8.11)$$

$$\phi_2=\frac{1}{3}\varphi_2. \quad (8.12)$$

Re-writing of the FD-SP$_3$ System

Described below is the derivation of the finite volume formulation of the FD-SP$_3$ (RD) model. As noted above, the derivation of the finite volume formulation of the FD-SP$_3$ (CD) model would be similar and thus is not discussed in detail. Moreover, for simplicity, the FD-SP$_3$ (RD) model is referred to as simply the "SP3" in this section. Thus, the SP3 equations (i.e., Eqns. 8.1-8.2 and 8.5-8.6) can be rewritten as follows:

$$-\nabla\cdot\mathcal{D}_1\nabla\varphi_1+\left(\mu_a+\frac{i\omega}{v}\right)\varphi_1=Q+\frac{2}{3}\left(\mu_a+\frac{i\omega}{v}\right)\varphi_2, \quad (8.13)$$

$$-\nabla\cdot\mathcal{D}_2\nabla\varphi_2+\left(\frac{4}{9}\mu_a+\frac{5}{9}\mu_{a2}+\frac{1}{3}\frac{i\omega}{v}\right)\varphi_2=-\frac{2}{3}Q+\frac{2}{3}\mu_a\varphi_1, \quad (8.14)$$

with the following set of boundary equations:

$$\alpha_1\phi_1+\mathcal{D}_1\beta_1(\hat{n}\cdot\nabla\phi_1)=\gamma_1\phi_2+7\mathcal{D}_2\delta_1(\hat{n}\cdot\nabla\phi_2)+S_1, \quad (8.15)$$

$$\alpha_2\phi_2+\mathcal{D}_2\beta_2(\hat{n}\cdot\nabla\phi_2)=\gamma_2\phi_1+3\mathcal{D}_1\delta_2(\hat{n}\cdot\nabla\phi_1)+S_2. \quad (8.16)$$

The corresponding formula for the partial current can be given by:

$$J^+=\left(\frac{1}{4}+J_0\right)\left(\varphi_1-\frac{2}{3}\varphi_2\right)- \quad (8.17)$$
$$\mathcal{D}_1(0.5+J_1)(\hat{n}\cdot\nabla\varphi_1)+\left(\frac{5}{16}+J_2\right)\left(\frac{1}{3}\varphi_2\right)-\mathcal{D}_2(J_3)(\hat{n}\cdot\nabla\varphi_2).$$

Coefficients that appear in Eqns. 8.1-8.17 are defined and summarized in Tables 1-3 herein.

Finite Volume Derivation of FD-SP$_3$ System

Eqns. 8.13-8.14 can be integrated and Stoke's theorem applied to convert the volume integral (defined within a finite volume element of total volume $\Delta V$) into a surface integral along the surfaces S of the volume element, such that:

$$-\int_S \mathcal{D}_1(\nabla\varphi_1\cdot\hat{n})dA+\left(\mu_a+\frac{i\omega}{v}\right)\varphi_1\Delta V=Q\Delta V+\frac{2}{3}\left(\mu_a+\frac{i\omega}{v}\right)\varphi_2\Delta V, \quad (8.18)$$

$$-\int_S \mathcal{D}_2(\nabla\varphi_2\cdot\hat{n})dA+\left(\frac{4}{9}\mu_a+\frac{5}{9}\mu_{a2}+\frac{1}{3}\frac{i\omega}{v}\right)\varphi_2\Delta V= \quad (8.19)$$
$$-\frac{2}{3}Q\Delta V+\frac{2}{3}\mu_a\varphi_1\Delta V.$$

The surface integrals in Eqns. 8.18-8.19 can be computed using numerical quadrature rules, for example, exploiting the fact that each volume element has a finite number of surfaces (typically less than 12 surfaces). The directional derivative (boundary flux) terms ($\nabla\phi_1\cdot\hat{n}$ and $\nabla\phi_2\cdot\hat{n}$) can be simplified by using the same properties of the finite volume element. For example, the direction derivate can be written in discretized form as follows:

$$\nabla\varphi_1\cdot\hat{n}\approx\frac{[\varphi_1]_i-[\varphi_1]_m}{dr_i}, \quad (8.20)$$

$$\nabla\varphi_2\cdot\hat{n}\approx\frac{[\varphi_2]_i-[\varphi_2]_m}{dr_i}. \quad (8.21)$$

TABLE 1

Definition of Variables

| Variable | Description | Units |
|---|---|---|
| FVM | Finite volume method | |
| FEM | Finite element method | |
| FDM | Finite differences method | |
| O | Imaging object | |
| V | Computational domain (i.e., discretization of O) | |
| M | Total number of discrete mesh elements in V | |
| m | Discrete mesh element, s.t. V = {m:m = 1 ... M} | |
| $S_B$ | Number of boundary surfaces of the mth FV element | |
| $S_I$ | Number of internal surfaces of the mth FV element | |
| $S_T$ | Total number of finite volume surfaces in V | |
| N | Order of SP$_N$ model | |

TABLE 1-continued

Definition of Variables

| Variable | Description | Units |
|---|---|---|
| $\mu_a$ | Absorption coefficient | $cm^{-1}$ |
| $\mu_s$ | Scattering coefficient | $cm^{-1}$ |
| $\mu'_s$ | Reduced scattering coefficient | $cm^{-1}$ |
| $\mu_{an}$ | nth order absorption coefficient | $cm^{-1}$ |
| g | Anisotropy factor | |
| $\varphi_n$ | nth order composite moment of the $SP_N$ model | $W\,cm^{-2}$ |
| $\Phi_n$ | nth order Legendre moments of the radiance | $W\,cm^{-2}$ |
| $\hat{n}$ | Normal vector pouting outwards at outer surface of O | |
| $\Omega$ | Angular direction | |
| r | Spatial position | |
| $\upsilon$ | Speed of light in tissue | $cm\,s^{-1}$ |
| $\omega$ | Modulation angular frequency ($2\pi f$) | $s^{-1}$ |
| Q | Interior source | $W\,cm^{-3}$ |
| S | Boundary source | $W\,cm^{-2}sr^{-1}$ |
| $J^+$ | Partial current | $W\,cm^{-2}$ |
| $J_n$ | Coefficients of the partial current | |
| i | Complex unit ($\sqrt{-1}$) | |

Consider an individual finite volume element m∈V with $S_I$ internal surfaces and $S_B$ boundary surfaces. By definition, element m shares each of the surfaces $S_I$ with a single neighboring finite volume element. Then, let i denote the ith neighbor of m, such that i=1 . . . $S_I$. Then, the finite volume version (i.e., discrete formulae) of Eqns. 8.13-8.14 are given by:

$$-\sum_{i=1}^{S_I} \mathcal{D}_1 \frac{[\varphi_1]_i - [\varphi_1]_m}{dr_i} dA_i + \left(\mu_a + \frac{i\omega}{\upsilon}\right)[\varphi_1]_m \Delta V = \quad (8.22)$$

$$[Q]_m \Delta V + \frac{2}{3}\left(\mu_a + \frac{i\omega}{\upsilon}\right)[\varphi_2]_m \Delta V,$$

$$-\sum_{i=1}^{S_I} \mathcal{D}_2 \frac{[\varphi_2]_i - [\varphi_2]_m}{dr_i} dA_i + \left(\frac{4}{9}\mu_a + \frac{5}{9}\mu_{a2} + \frac{1}{3}\frac{i\omega}{\upsilon}\right)[\varphi_2]_m \Delta V = \quad (8.23)$$

$$-\frac{2}{3}[Q]_m \Delta V + \frac{2}{3}\mu_a[\varphi_1]_m \Delta V.$$

TABLE 2

Boundary and current coefficients for the $SP_3$ model $$\mathcal{D}_1 = \frac{1}{3\mu_{a1}}$$

$$\mathcal{D}_2 = \frac{1}{7\mu_{a3}}$$

$$\alpha_1 = \frac{1}{2} + A_1$$

$$\alpha_2 = \frac{7}{24} + A_2$$

$$\beta_1 = 1 + B_1$$
$$\beta_2 = 1 + B_2$$
$$\gamma_1 = \frac{1}{8} + C_1$$
$$\gamma_2 = \frac{1}{8} + C_2$$
$$\delta_1 = D_1$$
$$\delta_2 = D_2$$

TABLE 2-continued

Boundary and current coefficients for the $SP_3$ model $$S_1 = \int_{\Omega \cdot \hat{n} < 0} S(\Omega) 2|\Omega \cdot \hat{n}| d\Omega$$

$$S_2 = \int_{\Omega \cdot \hat{n} < 0} S(\Omega)(5|\Omega \cdot \hat{n}|^3 - 3|\Omega \cdot \hat{n}|) d\Omega$$

$$\xi_{11} = \frac{\alpha_1 \beta_2 - 7\delta_1 \gamma_2}{\beta_1 \beta_2 - 21\delta_1 \delta_2}$$

$$\xi_{12} = \frac{7\delta_1 \alpha_2 - \gamma_1 \beta_2}{\beta_1 \beta_2 - 21\delta_1 \delta_2}$$

$$\xi_{13} = \frac{\beta_2}{\beta_1 \beta_2 - 21\delta_1 \delta_2}$$

$$\xi_{14} = \frac{7\delta_1}{\beta_1 \beta_2 - 21\delta_1 \delta_2}$$

$$\xi_{21} = \frac{3\delta_2 \xi_{11} - \gamma_2}{\beta_2}$$

$$\xi_{22} = \frac{3\delta_2 \xi_{12} + \alpha_2}{\beta_2}$$

$$\xi_{23} = \frac{3\delta_2 \xi_{13}}{\beta_2}$$

$$\xi_{24} = \frac{3\delta_2 \xi_{14} + 1}{\beta_2}$$

$$\phi_0 = \varphi_1 - \frac{2}{3}\varphi_2$$

$$\phi_1 = \frac{1}{3}\varphi_2$$

TABLE 3

Definition of variables for the linear problem of the $SP_3$ model

| Variable | Description | Dimensions |
|---|---|---|
| A | Forward model | $\mathbb{C}^{2M \times 2M}$ |
| b | Source vector | $\mathbb{C}^{2M}$ |
| x | Solution vector (i.e., composite moments of $SP_N$ model) | $\mathbb{C}^{2M}$ |
| Q | Projection operator; maps forward solution to detector readings | $\mathbb{C}^{P \times M}$ |
| p | Number of source/detector pairs | |
| $\hat{\mu}_a$ | Rescaled absorption coefficient | |
| $\hat{\mu}_{s_a}$ | Rescaled scattering coefficient | |
| $la$ | Linear coefficient of the linear transformation of $\mu_a$ | |
| $l_s$ | Linear coefficient of the linear transformation of $\mu_s$ | |
| $c_a$ | Constant coefficient of the linear transformation of $\mu_a$ | |
| $c_s$ | Constant coefficient of the linear transformation of $\mu_s$ | |

Finite Volume Derivation of the Boundary Equations

Solving boundary equations Eqns. 8.15-8.16 for $(\hat{n} \cdot \nabla \phi_1)$ and $(\hat{n} \cdot \nabla \phi_2)$ yields:

$$(\hat{n} \cdot \nabla \varphi_1) = \frac{1}{\mathcal{D}_1}(-\xi_{11}\varphi_1 - \xi_{12}\varphi_2 + \xi_{13}S_1 + \xi_{14}S_2), \quad (8.24)$$

-continued $$(\hat{n}\cdot\nabla\varphi_2) = \frac{1}{D_2}(-\xi_{21}\varphi_1 - \xi_{22}\varphi_2 + \xi_{23}S_1 + \xi_{24}S_2). \quad (8.25)$$

Definitions of the coefficients $\xi$ are summarized in Table 2. Eqns. 8.24-8.25 can be used on Eqns. 8.18-8.19 to solve for the following system of discretized boundary equations.

$$\sum_{i=1}^{S_B}\xi_{11}[\varphi_1]_m dA_i + \sum_{i=1}^{S_B}\xi_{12}[\varphi_2]_m dA_i + \quad (8.26)$$

$$\left(\mu_a + \frac{i\omega}{\upsilon}\right)[\varphi_1]_m \Delta V - \frac{2}{3}\left(\mu_a + \frac{i\omega}{\upsilon}\right)[\varphi_2]_m \Delta V =$$

$$[Q]_m \Delta V + \sum_{i=1}^{S_B}\xi_{13}[S_1]_p dA_i + \sum_{i=1}^{S_B}\xi_{14}[S_4]_p dA_i$$

$$\sum_{i=1}^{S_B}\xi_{21}[\varphi_1]_m dA_i + \sum_{i=1}^{S_B}\xi_{22}[\varphi_2]_m dA_i + \quad (8.27)$$

$$\left(\frac{4}{9}\mu_a + \frac{5}{9}\mu_{a2} + \frac{i\omega}{\upsilon}\right)\varphi_2 \Delta V - \frac{2}{3}\mu_a[\varphi_1]_m \Delta V =$$

$$-\frac{2}{3}[Q]_m \Delta V + \sum_{i=1}^{S_B}\xi_{23}[S_1]_p dA_i + \sum_{i=1}^{S_B}\xi_{24}[S_2]_p dA_i$$

Partial Current Operator

The partial current, $J^+$, can be discretized by using Eqns. 8.24-8.25 on Eqn. 8.17. This operation results in the following discretized partial current operator that acts on the fluence moments $\phi_n$ and boundary sources $S_n$:

$$J^+ = \nu_0\phi_1 + \nu_1\phi_2 + \nu_2 S_1 + \nu_3 S_2 \quad (8.28)$$

The coefficients, $\nu_n$, in Eqn. 8.28 are given by:

$$\nu_0 = \left[\frac{1}{4} + J_0 + \left(\frac{1}{2} + J_1\right)\xi_{11} + J_3\xi_{21}\right] \quad (8.29)$$

$$\nu_1 = \left[-\frac{3}{48} - \frac{2}{3}J_0 + \frac{1}{3}J_2 + \left(\frac{1}{2} + J_1\right)\xi_{12} + J_3\xi_{22}\right]$$

$$\nu_2 = -\left[\left(\frac{1}{2} + J_1\right)\xi_{13} + J_3\xi_{23}\right]$$

$$\nu_3 = -\left[\left(\frac{1}{2} + J_1\right)\xi_{14} + J_3\xi_{24}\right]$$

As there is only one single equation to be solved on each individual finite volume element, Eqns. 8.22, 8.23, 8.26, and 8.27 can be combined to yield the following comprehensive $SP_3$ equations, which are valid for all individual finite volume elements with $S_I$ internal surfaces and $S_B$ boundary surfaces:

$$\sum_{i=1}^{S_B}\xi_{11}[\varphi_1]_m dA_i + \sum_{i=1}^{S_B}\xi_{12}[\varphi_2]_m dA_i - \sum_{i=1}^{S_I}D_2\frac{[\varphi_2]_i - [\varphi_2]_m}{dr_i}dA_i +$$

$$\left(\mu_a + \frac{i\omega}{\upsilon}\right)[\varphi_1]_m \Delta V - \frac{2}{3}\left(\mu_a + \frac{i\omega}{\upsilon}\right)[\varphi_2]_m \Delta V =$$

$$[Q]_m \Delta V + \sum_{i=1}^{S_B}\xi_{13}[S_1]_p dA_i + \sum_{i=1}^{S_B}\xi_{14}[S_2]_p dA_i,$$

$$\sum_{i=1}^{S_B}\xi_{21}[\varphi_1]_m dA_i + \sum_{i=1}^{S_B}\xi_{22}[\varphi_2]_m dA_i - \sum_{i=1}^{S_I}D_2\frac{[\varphi_2]_i - [\varphi_2]_m}{dr_i}dA_i +$$

-continued $$\left(\frac{4}{9}\mu_a + \frac{5}{9}\mu_{a2} + \frac{i\omega}{\upsilon}\right)\varphi_2 \Delta V - \frac{2}{3}\mu_a[\varphi_1]_m \Delta V =$$

$$-\frac{2}{3}[Q]_m \Delta V + \sum_{i=1}^{S_B}\xi_{23}[S_1]_p dA_i + \sum_{i=1}^{S_B}\xi_{24}[S_2]_p dA_i$$

Furthermore, the partial current can be simplified by noting that $S_1$ and $S_2$, as they appear in Eqn. 8.28, can be set to zero, since $S_1$ and $S_2$ generally vanish when considering only outward-pointing discrete ordinates on the surface of the object under investigation. The formula for partial current thus becomes:

$$[J^+]_m = \nu_0[\phi_1]_m + \nu_1[\phi_2]_m.$$

Forward Model

The FD-$SP_3$ model given by Eqns. 8.13-8.14 is described in the FVM formulation by Eqns. 8.22, 8.23, 8.26 and 8.27. These equations can be used to solve for the composite moments of the fluence, $\phi_1$ and $\phi_2$. The fluence or Legendre moments of the radiance, $\phi_n$, can be computed from $\phi_n$. In DOT, the quantity of interest is the partial current, $J^+(r, \omega)$, which is a measure of the energy that exits the medium at surface point r and is measured by detectors. This partial current can be computed by applying Eqn. 8.28 to $\phi_n$.

The system of equations (e.g., Eqns. 8.22, 8.23, 8.26, and 8.27) can be converted into an algebraic problem that is completely independent of the underlying physical problem (i.e., the computational mesh). The forward problem for the $SP_3$ model can be formulated into a system of algebraic equations of the form:

$$Ax = b, \quad (8.30)$$

where A is the "forward model" (i.e., the FV-FD-SPN model), x is the "forward solution" (i.e., the composite moments of the FV-FD-SPN model), and b denotes the source terms for the forward problem. Such a formulation is compact and can allow for the application of algebraic techniques for solving for x and differentiating the entire expression with respect to x.

Matrix A is a square matrix of size M×M for $SP_1$ and 2M×2M for $SP_3$, where M is the number of distinct mesh nodes in the numerical grid that discretizes the imaging volume O. The elements of A are given by the left hand side terms of Eqns. 8.22, 8.23, 8.26, and 8.27 that do not contain S (boundary source) or Q (internal source). The contributions from associated boundary and internal source terms are stored in b, a vector of length M for $SP_1$ and 2M for SP3. The elements of b are given by the terms in Eqns. 8.22, 8.23, 8.26, and 8.27 that contain S and Q.

The forward solution, x, is a vector of length M for $SP_1$ and 2M for $SP_3$. Specifically, x=$\phi_1$ for $SP_1$ and x=$[\phi_1^T \phi_2^T]^T$ for $SP_3$. The algebraic system given by Eqn. 8.30 allows for the solution of $\phi_1$ and $\phi_2$ to be obtained simultaneously. The conjugate transpose of the complex vectors $\phi_1$ and $\phi_2$ are denoted by T.

For clarity and for improved computational performance, the final discretized form of the $SP_3$ model defined by Eqns. 8.22, 8.23, 8.26, and 8.27 can be rewritten. The absorption and scattering coefficients are inherently in significantly different scales ($\mu_s \gg \mu_a$), which can lead to slow convergence during the reconstruction process. This issue can be overcome by defining scaled absorption ($\hat{\mu}_a$) and scattering ($\hat{\mu}_s$) coefficients as:

$$\hat{\mu}_a = l_a\mu_a + c_a,$$

$$\hat{\mu}_s = l_s\mu_s + c_s,$$

where $l_a$, $c_a$, $l_s$, and $c_s$ are computed from predefined minimum and maximum allowed values for $\mu_a$ and $\mu_s$. For example, $\mu_a \epsilon [0.0, 1.0]$ cm$^{-1}$ and $\mu_s \epsilon [0.0, 200.0]$ cm$^{-1}$ (assuming the anisotropic $g \approx 0.9$). These upper and lower bounds can be used for rescaling purposes only and are not necessarily constraints on the admissible values of the variables.

The nth order diffusion operator ($\mathcal{D}_n$) appearing in Eqns. 8.22-8.23 are defined at the face of the finite volume element and can be replaced with corresponding nodal values (i.e., the value at the center of the finite volume element). This can be achieved by replacing the nth order diffusion coefficients ($\mathcal{D}_1$ and $\mathcal{D}_2$) with the average of these coefficients between node m and its neighboring element i, as follows:

$$\mathcal{D}_1 = \frac{[\mathcal{D}_1]_m + [\mathcal{D}_1]_i}{2},$$

$$\mathcal{D}_2 = \frac{[\mathcal{D}_2]_m + [\mathcal{D}_2]_i}{2}.$$

Thus, the final version of the SP$_3$ model can be obtained by expanding the $\mathcal{D}_1$ and $\mathcal{D}_2$ terms, then expanding all $\mu_{an}$ terms, and then replacing $\mu_a$ and $\mu_s$ with $\hat{\mu}_a$ and $\hat{\mu}_s$ throughout. This leads to the following expanded expressions for $\mathcal{D}_1$ and $\mathcal{D}_2$:

$$\mathcal{D}_1 = \frac{1}{2}\left[\frac{1}{3\left(\frac{[\hat{\mu}_a]_m - c_a}{l_a} + (1-g)\frac{[\hat{\mu}_s]_m - c_s}{l_s}\right)} + \frac{1}{3\left(\frac{[\hat{\mu}_a]_i - c_a}{l_a} + (1-g)\frac{[\hat{\mu}_s]_i - c_s}{l_s}\right)}\right], \quad (8.31)$$

$$\mathcal{D}_2 = \frac{1}{2}\left[\frac{1}{7\left(\frac{[\hat{\mu}_a]_m - c_a}{l_a} + (1-g^3)\frac{[\hat{\mu}_s]_m - c_s}{l_s}\right)} + \frac{1}{7\left(\frac{[\hat{\mu}_a]_i - c_a}{l_a} + (1-g^3)\frac{[\hat{\mu}_s]_i - c_s}{l_s}\right)}\right]. \quad (8.32)$$

Matrix A is a symmetric sparse matrix, with up to $2S_T + 4M$ non-zero elements for the SP$_3$ system, where $S_T$ is the total number of finite volume surfaces in a mesh that has M mesh nodes. The elements of the forward model A can be summarized as a contributions from Eqns. 8.22, 8.23, 8.26, and 8.27. The composite moments are shown in the formulation of A and b. However, it should be noted that the composite moments do not occur in either of these variables. Instead, the elements of the matrix A can be determined as follows:

I. Elements of matrix A—from Eqn. 8.22:
(a) Elements stored in (row m, column m)

$$[\varphi_1]_m\left(\frac{[\hat{\mu}_a]_m - c_a}{l_a}[\Delta V]_p + \frac{i\omega}{\upsilon}[\Delta V]_p + \sum_{i=1}^{S_I} \mathcal{D}_1 \frac{dA_i}{dr_i}\right)$$

(b) Elements stored in (row m, column i)

$$[\varphi_1]_i\left(-\mathcal{D}_1 \frac{dA_i}{dr_i}\right)$$

(For each interior surface $i=1 \ldots S_I$)

(c) Elements stored in (row m, column m+M)

$$[\varphi_2]_m\left(-\frac{2}{3}\frac{[\hat{\mu}_a]_m - c_a}{l_a}[\Delta V]_p - \frac{2}{3}\frac{i\omega}{\upsilon}[\Delta V]_p\right)$$

II. Elements of matrix A (for each boundary surface $i = 1 \ldots S_B$)—from Eqn. 8.26:
(a) Elements stored in (row m, column m)

$$[\varphi_1]_m\left(\frac{[\hat{\mu}_a]_m - c_a}{l_a}[\Delta V]_p + \frac{i\omega}{\upsilon}[\Delta V]_p + \sum_{i=1}^{S_B} \xi_{11} dA_i\right)$$

(b) Elements stored in (row m, column m+M)

$$[\varphi_2]_m\left(-\frac{2}{3}\frac{[\hat{\mu}_a]_m - c_a}{l_a}[\Delta V]_p - \frac{2}{3}\frac{i\omega}{\upsilon}[\Delta V]_p + \sum_{i=1}^{S_B} \xi_{12} dA_i\right)$$

III. Elements of vector b—from Eqns. 8.22, 8.26:
(a) Interior Eq. (row m)

$$[Q]_m [\Delta V]_p$$

(b) Boundary Eq. (row m)

$$[Q]_m [\Delta V]_p + (\xi_{13}[S_1]_p + \xi_{14}[S_2]_p)\sum_{i=1}^{S_B} dA_i$$

(For each boundary surface $i=1 \ldots S_B$)

The contributions from Eqns. 8.23 and 8.27 are given by:
I. Elements of matrix A—from Eqn. 8.23:
(a) Elements stored in (row m+M, column m)

$$[\varphi_1]_m\left(-\frac{2}{3}\frac{[\hat{\mu}_a]_m - c_a}{l_a}[\Delta V]_p\right)$$

(b) Elements stored in (row m+M, column m+M)

$$[\varphi_2]_m\left(\frac{[\hat{\mu}_a]_m - c_a}{l_a}[\Delta V]_p + (1-g^2)\frac{5}{9}\frac{[\hat{\mu}_s]_m - c_s}{l_s}[\Delta V]_p + \frac{1}{3}\frac{i\omega}{\upsilon}[\Delta V]_p + \sum_{i=1}^{S_I} \mathcal{D}_2 \frac{dA_i}{dr_i}\right)$$

(c) Elements stored in (row m+M, column i+M)

$$[\varphi_2]_i\left(-\mathcal{D}_2 \frac{dA_i}{dr_i}\right)$$

(for each interior surface $i=1 \ldots S_I$)

II. Elements of matrix A (for each boundary surface $i = 1 \ldots S_B$)—from Eqn. 8.27:
(a) Elements stored in (row m+M, column m)

$$[\varphi_1]_m \left( -\frac{2}{3} \frac{[\hat{\mu}_a]_m - c_a}{l_a} [\Delta V]_p + \sum_{i=1}^{S_B} \xi_{21} dA_i \right)$$

(b) Elements stored in (row m+M, column m+M)

$$[\varphi_2]_m \left( \frac{[\hat{\mu}_a]_m - c_a}{l_a} [\Delta V]_p + (1 - g^2) \frac{5}{9} \frac{[\hat{\mu}_s]_m - c_s}{l_s} [\Delta V]_p + \frac{1}{3} \frac{i\omega}{v} [\Delta V]_p + \sum_{i=1}^{S_B} \xi_{22} dA_i \right)$$

III. Elements of vector b—from Eqns. 8.23, 8.27:
(a) Interior Eq. (row m+M)

$$-\frac{2}{3} [Q]_m [\Delta V]_p$$

(b) Boundary Eq. (row m+M)

$$-\frac{2}{3} [Q]_m [\Delta V]_p + (\xi_{23} [S_1]_p + \xi_{24} [S_2]_p) \sum_{i=1}^{M} dA_i$$

(For each boundary surface $i = 1 \ldots S_B$)
Partial Current

The partial current, $J^+(r, \omega)$, can be computed as:

$$J^+(r,\omega) = Q [x^T b^T]^T, \quad (8.33)$$

Where Q is a projection operator that transforms the composite moments $\phi_n$ and source terms $Q(r)$ and $S(r, \Omega)$ into partial current measurements. For the SP3 model, the projection operator Q can be given by:

$$Q = [Q_0 Q_1 Q_2 Q_3]$$

Matrix Q can be derived from Eqns. 8.28-8.29 and has dimensions p×4M, where p is the total number of source-detector pairs. Matrices $Q_n \in \mathbb{R}^{p \times M}$ can have the following structure:

$$Q_n = \begin{bmatrix} v_n & 0 & \ldots & 0 & 0 \\ 0 & v_n & \ldots & 0 & 0 \\ \vdots & \vdots & \ddots & \vdots & \vdots \\ 0 & 0 & \ldots & v_n & 0 \\ 0 & 0 & \ldots & 0 & v_n \end{bmatrix}.$$

Each $v_n$ term can be computed for each mesh node that maps to a detector. Further simplifications to the partial current operator can be obtained as a result of the simplification to Eqn. 8.28, which results in setting b to zero (i.e., b=0) in Eqn. 8.33.

Numerical Solver for the Forward Model

The system of linear equations resulting from the FV-FD-SPN model of Eqn. 8.30 can be solved with a (restarted) generalized minimal residual method (GMRES), which is a Krylov subspace iterative method allowing for efficient solving of systems of linear equations. GMRES can properly handle the forward model, where the coefficient matrix A is complex-valued and symmetric. The GMRES algorithm, in a simplified text format, is shown below in Table 4.

TABLE 4

Algorithm 1-GMRES algorithm

Compute $r_0 = b - Ax_0$, $\beta := \|r_0\|_2$, and $v_1 := r_0/\beta$
for $j = 1, 2, \ldots, m$ do
   Compute $w_j := Av_j$
   for $i = 1, \ldots, j$ do
     $h_{ij} := (w_j, v_i)$
     $w_j := w_j - h_{ij} v_i$
   end for
   $h_{j+1,j} = \|w_j\|_2$.
   if $h_{j+1,j} = 0$ then
     Set $m := j$ and go to last line
   end if
   $v_{j+1} = w_j/h_{j+1,j}$.
end for
Define the $(m + 1) \times m$ Hessenberg matrix $\overline{H}_m = \{h_{ij}\}_{1 \leq i \leq m+1, 1 \leq j \leq m}$.
Compute $y_m$ the minimizer of $\|\beta e_1 - \overline{H}_m y\|_2$ and $x_m = x_0 + V_m y_m$.

The solution to the linear system of Eqn. 8.30 is given by $x_m$ in the GMRES algorithm. The coefficient matrix A, and vectors x and y are complex-valued. As a result, the Hessenberg matrix ($\overline{H}$), the associated vectors (r, v, $\omega$), and the coefficient h are all complex-valued.

The derivation of the FVM algorithm for the alternate version of the FD-SPN model (i.e., the FD-SPN (CD) model in Eqns. 8.3, 8.4, 8.7, 8.8, and 8.10), follows the same logic presented for FD-SPN (RD). The only differences are the locations throughout the equations where the imaginary terms, $$\frac{i\omega}{v},$$

and its preceding weights occur.

Numerical Phantoms

The fluence ($\phi$) and partial current ($J^+$) measurements obtained with the FV-FD-SPN model can be compared to solutions obtained with a benchmark algorithm based on the ERT model using a dense set of discrete ordinates ($S_{12}$). To differentiate between solutions from the SPN (RD) (i.e., the model has strictly real-valued diffusion coefficients) and SPN (CD) (i.e., the model has complex-valued diffusion coefficients) models, the following nomenclature can be used: solutions computed with SPN (RD) are labeled "SPN (RD)" and solutions computed with SPN (CD) are labeled "SPN (CD)."

For numerical simulations, a two-dimensional circular phantom is used. The circular phantom has a diameter of 2.0 cm whose origin is at the center of the disk (x=0.0 cm, y=0.0 cm). The performances of the SPN models are analyzed by varying the optical properties of the medium. Four specific sets of optical properties are considered, which together provide insight into the appropriateness of the various SPN models in the extremely diffuse regime and in the non-diffuse regime.

Figure 4C:
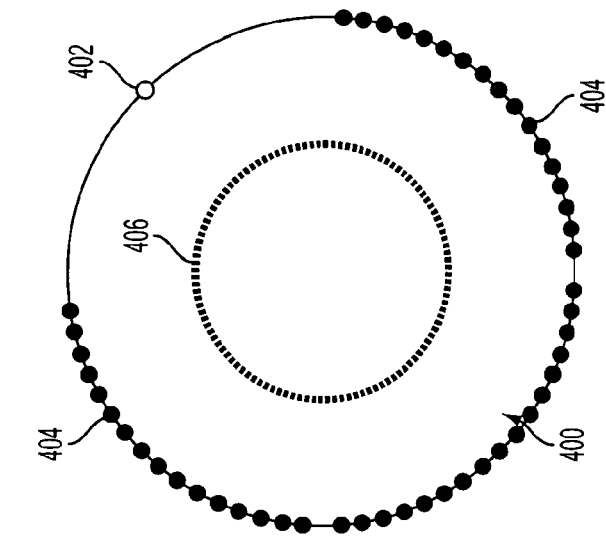
FIGS. 4A-4C show FEM mesh elements, FVM mesh elements, and locations of a source and detectors, respectively, for a disk-shaped object, according to one or more embodiments of the disclosed subject matter.
Figure 4B:
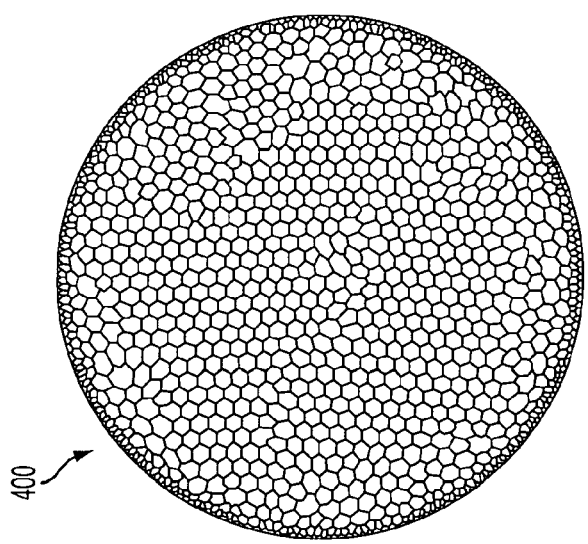
Figure 4A:
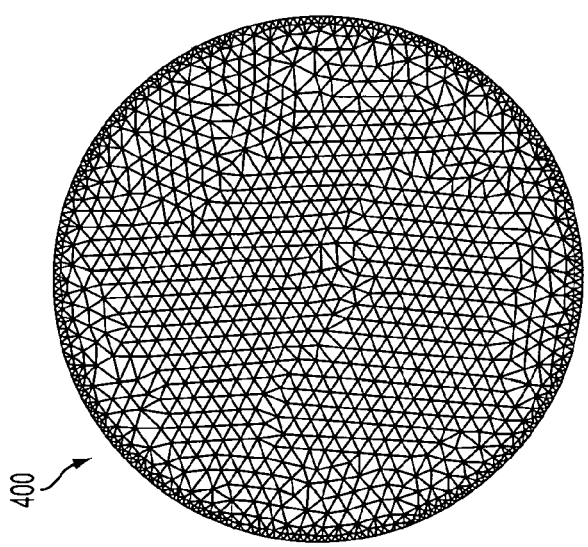

The phantom, which can be a disk 400, can be discretized by a dense numerical grid, which may ensure that the numerical error from the ERT algorithm is minimal or at least reduced. For example, the FEM mesh can have 37,247 mesh nodes and 73,236 triangular elements, resulting in an FVM mesh with 37,247 volume elements and 220,964 surfaces. FIGS. 4A-4B show examples of the discretization of disk 400 (e.g., 2.0 cm diameter) into triangular elements for the FEM mesh (FIG. 4A) and into finite-volume elements for the FVM mesh (FIG. 4B). It is noted that the mesh is not drawn to scale or is shown at a substantially reduced density to allow for ease of viewing. In the example of FIGS. 4A-4B, the FEM mesh has 1,309 FEM nodes (i.e., 2,360 triangles), while the FVM mesh contains 1,309 finite volume elements with 6,028 surfaces. The computation time required to generate the FVM mesh from the FEM mesh is minimal (e.g., on the order of 0.011 s in the example presented) and thus can generally be ignored.

There is a source 402 on the boundary of disk 400. For example, source 402 can be positioned at a position of x=0.7071 cm and y=0.7071 cm. The source 402 can have a power of $S(\omega)=1.0$ W cm$^{-2}$ sr$^{-1}$. Detectors 404 (only a portion of which have been labeled in FIG. 4C), can be distributed evenly around the phantom boundary at points away from the source 402. For example, there can be 50 detectors. Fewer or additional sources and/or detectors and different arrangements of sources and detectors are also possible according to one or more contemplated embodiments.

The partial current, $J^+(r)$, can be computed at each of the detectors. The fluence, $\phi(r)$, can be computed on all 37,247 FVM elements. To analyze the differences between the fluence computed with the SPN models and the benchmark solution, a cross-section of interest (represented by inner circle 406) is defined within the phantom, which includes all mesh points 0.5±0.01 cm from the center of the phantom. The cross-section of interest can be chosen, for example, because it crosses all inclusions and therefore allows for the analysis of fluence within those objects of interest.

The background optical properties of the four phantoms are summarized in Table 5. The specific location of the inclusions and their optical properties are shown in FIGS. 5A-D. The first through fourth phantoms thus correspond to the optical properties shown in FIGS. 5A-5D, respectively.

The first phantom (FIG. 5A) is homogeneous with low absorption ($\mu_a=0.001$ cm$^{-1}$) and high scattering ($\mu_s=400$ cm$^{-1}$, g=0.95). This medium simulates highly diffuse tissue where the diffusion equation is known to be an accurate model of light propagation. The remaining three phantoms are inhomogeneous distributions of optical properties with either highly absorbing inclusions (e.g., phantom number two, FIG. 5B), low scattering inclusions (e.g., phantom number three, FIG. 5C), or a combination of these inclusions (e.g., phantom number four, FIG. 5d). Each of the inclusions are disks with 0.25 cm diameter. Phantoms number two, three, and four are designed to test the accuracy of the SPN equations in the transport regime, where the diffusion equation can be a poor approximation to the ERT.

The relative error, $J_e^+(r)$, between the benchmark partial current, $J_{ERT}^+(r)$, and the partial current computed with the SP$_1$ and SP$_3$ models, $J_{SP1}^+(r)$ and $J_{SP3}^+(r)$, can be computed at each mesh node i using the following formula:

$$J_e^+(r)_i = 100 \times \frac{J_{SPN}^+(r)_i - J_{ERT}^+(r)_i}{J_{ERT}^+(r)_i} \qquad (8.34)$$

The average relative error of the partial current, $\tilde{J}_e^+(r)$, is also reported as a measure of overall error. The relative error, $\phi_e(r)$, between the benchmark fluence, $\phi^{ERT}(r)$, and the 0th order moment of the radiance (i.e., the fluence) computed with the SP$_1$ and SP$_3$ models, $\phi^{SP1}(r)$ and $\phi^{SP3}(r)$, can be computed at each mesh node i using Eqn. 8.35. A second parameter that quantifies the error between the SPN and ERT solutions is the average error between the solutions at each mesh point, denoted $\tilde{\phi}_e(r)$, and is given by Eqn. 8.36. The finite volume $\Delta V$ (or finite area in the case of two-dimensional problems) of each FVM element can be used as a weight factor in the Riemann sum.

$$\phi_e(r)_i = 100 \times \frac{\phi^{SPN}(r)_i - \phi_i^{ERT}(r)}{\phi^{ERT}(r)_i} \qquad (8.35)$$

$$\tilde{\phi}_e(r) = \frac{100}{V} \times \sum_{i=1}^{N} \left( \frac{\phi^{SPN}(r)_i - \phi_i^{ERT}(r)}{\phi^{ERT}(r)_i} \right) \Delta V_i \qquad (8.36)$$

Here, V represents the total computational volume (or total area in two-dimensional problems). Error measures equivalent to Eqns. 8.35-8.36 between the fluence computed with the SPN and ERT along the internal cross-section 406, as shown in FIG. 4C, are denoted as, $\phi_e^*(r)_i$ and $\tilde{\phi}_e^*(r)$, respectively. The restarted GMRES algorithm is used to solve the forward problem in all cases. In these examples, the GMRES algorithm is set to restart after 30 iterations with no limit on the number of total iterations. The convergence criteria can be set to, for example, $1\times10^{12}$.

With the SP$_3$ model, the photon fluence ($\phi_0$) throughout the medium is obtained by a linear combination of the first two composite moments, $\phi_1$ and $\phi_2$ $$\left( \phi_0 = \varphi_1 - \frac{2}{3}\varphi_2 \right).$$

The individual moments are presented for all simulations with the SP$_3$ model for detailed analysis.

Numerical Study—Phantom 1: Homogenous Media

Results from simulations on the homogeneous phantom with highly diffuse properties (FIG. 5A) are discussed

TABLE 5

Background properties of numerical phantoms
(modulation frequency is from the relation ($\omega = 2\pi f$))

| Phantom | Optical Property Characteristics | $\mu_a$ (cm$^{-1}$) | $\mu_s$ (cm$^{-1}$) | g | $n_m$ | $\omega$ (MHz) |
|---|---|---|---|---|---|---|
| 1 | Homogeneous | 0.001 | 400.0 | 0.95 | 1.0 | 600 |
| 2 | Absorbing inclusions | 0.1 | 100.0 | 0.95 | 1.0 | 600 |
| 3 | Scattering inclusions | 0.1 | 100.0 | 0.95 | 1.0 | 600 |
| 4 | Absorbing and scattering inclusions | 0.1 | 200.0 | 0.95 | 1.0 | 600 | below. All three light propagation models return fluence distributions that are qualitatively similar, verifying that all models converge to similar solutions in highly diffuse media. Images of the amplitude and the phase of the fluence computed with the SPN models and the ERT model are presented in FIGS. 6-7. Maps of the relative error between the SPN solutions and the benchmark ERT solution are also presented in these figures. In particular, FIG. 6A-6E show the amplitude in log scale of the fluence computed with the $SP_1$ (CD), the $SP_1$ (RD), the $SP_3$ (CD), the $SP_3$ (RD), and the ERT ($S_{12}$) models, respectively. FIGS. 6F-6I show the percent error at each node of FIGS. 6A-6D relative to the ERT ($S_{12}$) benchmark of FIG. 6E. Similarly, FIGS. 7A-E show the phase of the fluence computed with the $SP_1$ (CD), the $SP_1$ (RD), the $SP_3$ (CD), the $SP_3$ (RD), and the ERT ($S_{12}$) models, respectively, and FIGS. 7F-7I show the percent error at each node of FIGS. 7A-7D relative to the ERT ($S_{12}$) benchmark of FIG. 7E. The average errors of the fluence and the partial current are summarized in Table 6.

The relative error of the amplitude of the fluence, as illustrated in FIGS. 6F-6I, shows agreement between all models. The average relative error between the SPN solutions and the benchmark solution is between 9.90% and 10.51%. At the individual mesh node level, the error is in the range of ±20.0%; however, the error at mesh nodes near the source can reach much higher values and has been artificially capped at ±20.0% in order to properly display the error across the rest of the phantom. Thus, all SPN models are incapable of accurately modeling the "transport" behavior of photons near the source. However, because the media is highly diffuse, transport photons become diffuse after only a short distance, which is the reason why the error in the SPN solutions is lower (generally bounded by ±20.0%) across the rest of the medium.

Similar observations can be made from analysis of the phase of the fluence (FIGS. 7A-7I). This suggests that there is agreement between all solutions. The average relative error between the phase of the fluence ranges from 9.32% to 10.04%. While there is significant error at mesh nodes within close proximity to the source, the error at nodes a short distance from the node is significantly lower.

Figure 8:
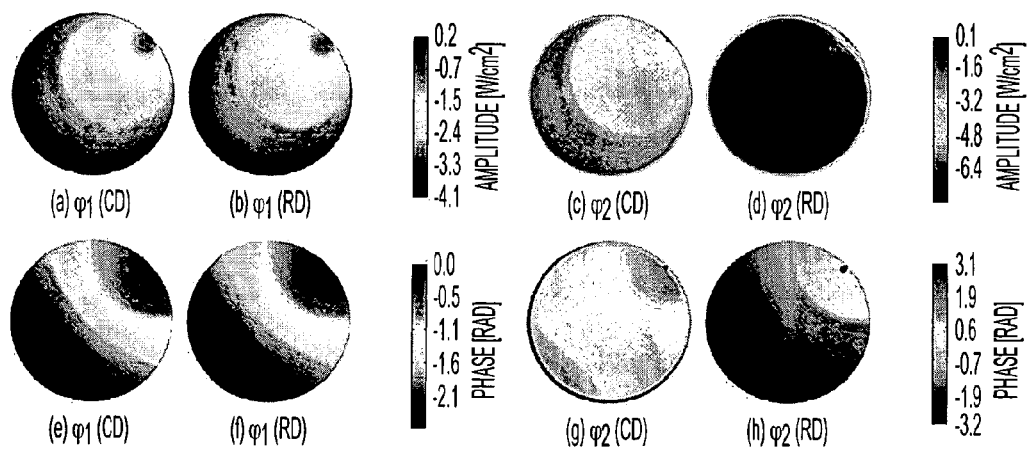
FIGS. 8A-8H show the amplitude and phase of the composite moments computed using different $SP_3$ models for the first phantom of FIG. 5A, according to one or more embodiments of the disclosed subject matter.

The individual components of the fluence computed with the $SP_3$ model (i.e., the first two composite moments $\phi_1$ and $\phi_2$) are presented in FIGS. 8A-8H. In particular, FIGS. 8A-8B represent the amplitude of the composite moment $\phi_1$ computed with the $SP_3$ (CD) and $SP_3$ (RD) models, respectively. FIGS. 8C-8D represent the amplitude of the composite moment $\phi_2$ computed with the $SP_3$ (CD) and $SP_3$ (RD) models, respectively. FIGS. 8E-8F represent the phase of the composite moment $\phi_1$ computed with the $SP_3$ (CD) and $SP_3$ (RD) models, respectively. FIGS. 8G-8H represent the phase of the composite moment $\phi_2$ computed with the $SP_3$ (CD) and $SP_3$ (RD) models, respectively.

The amplitude and the phase distributions of $\phi_1$ are similar for both CD and RD methods, although the $SP_3$ (CD) model exhibits marginally lower overall relative error in amplitude (9.96%) than the $SP_3$ (RD) model (10.31%). However, there are significant differences between the amplitude and phase distributions of $\phi_2$. The CD model produces a $\phi_2$ with significantly larger amplitude, suggesting that the CD model "corrects" more than the RD model. This may not actually result in improved solutions. For example, the $SP_3$ (CD) model exhibits higher overall relative error in phase (10.04%) than the $SP_3$ (RD) model (9.64%).

Figure 9:
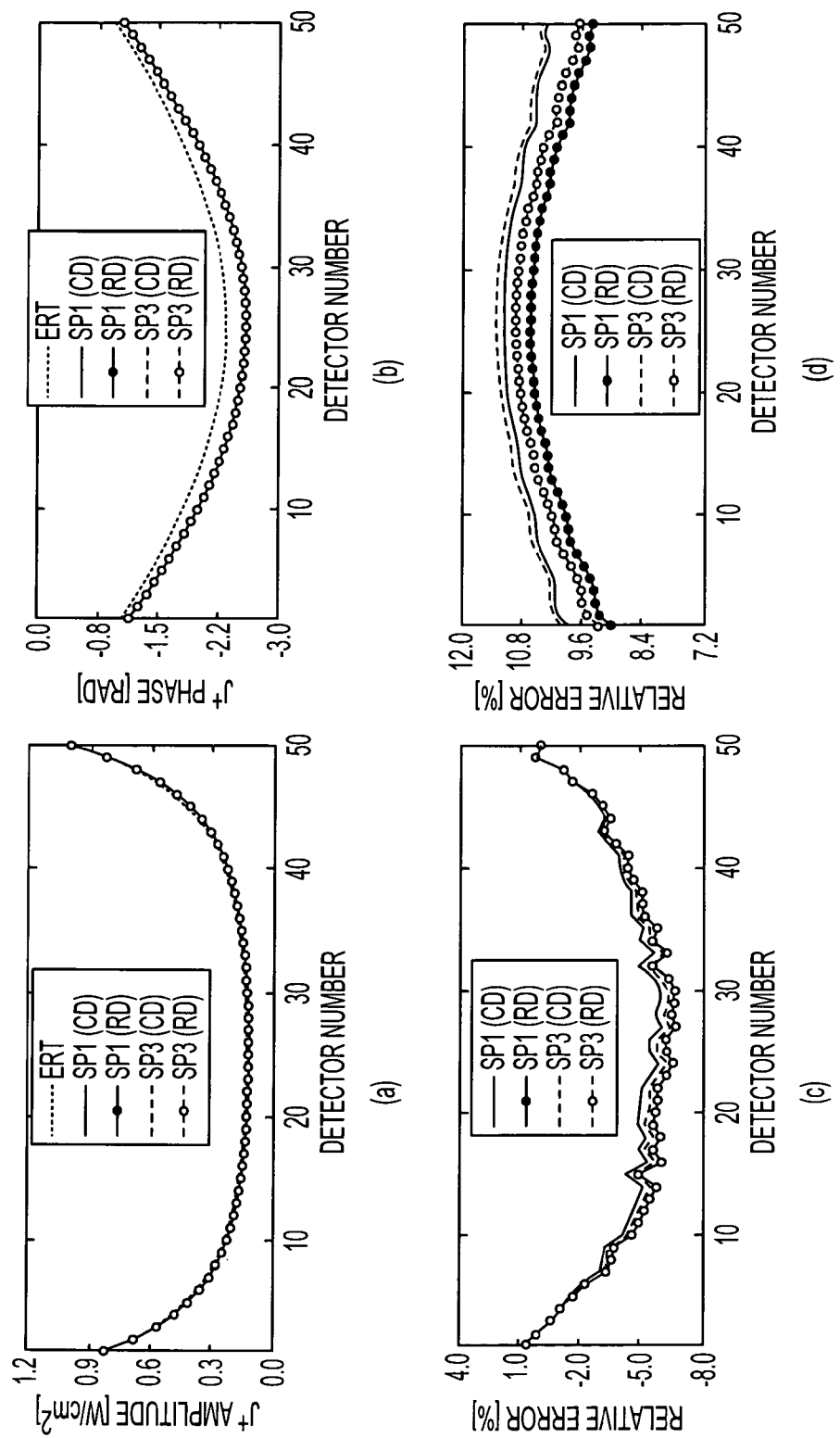
FIGS. 9A-9D are graphs of the amplitude and phase of the partial current and corresponding error for the first phantom of FIG. 5A, according to one or more embodiments of the disclosed subject matter.
Figure 10:
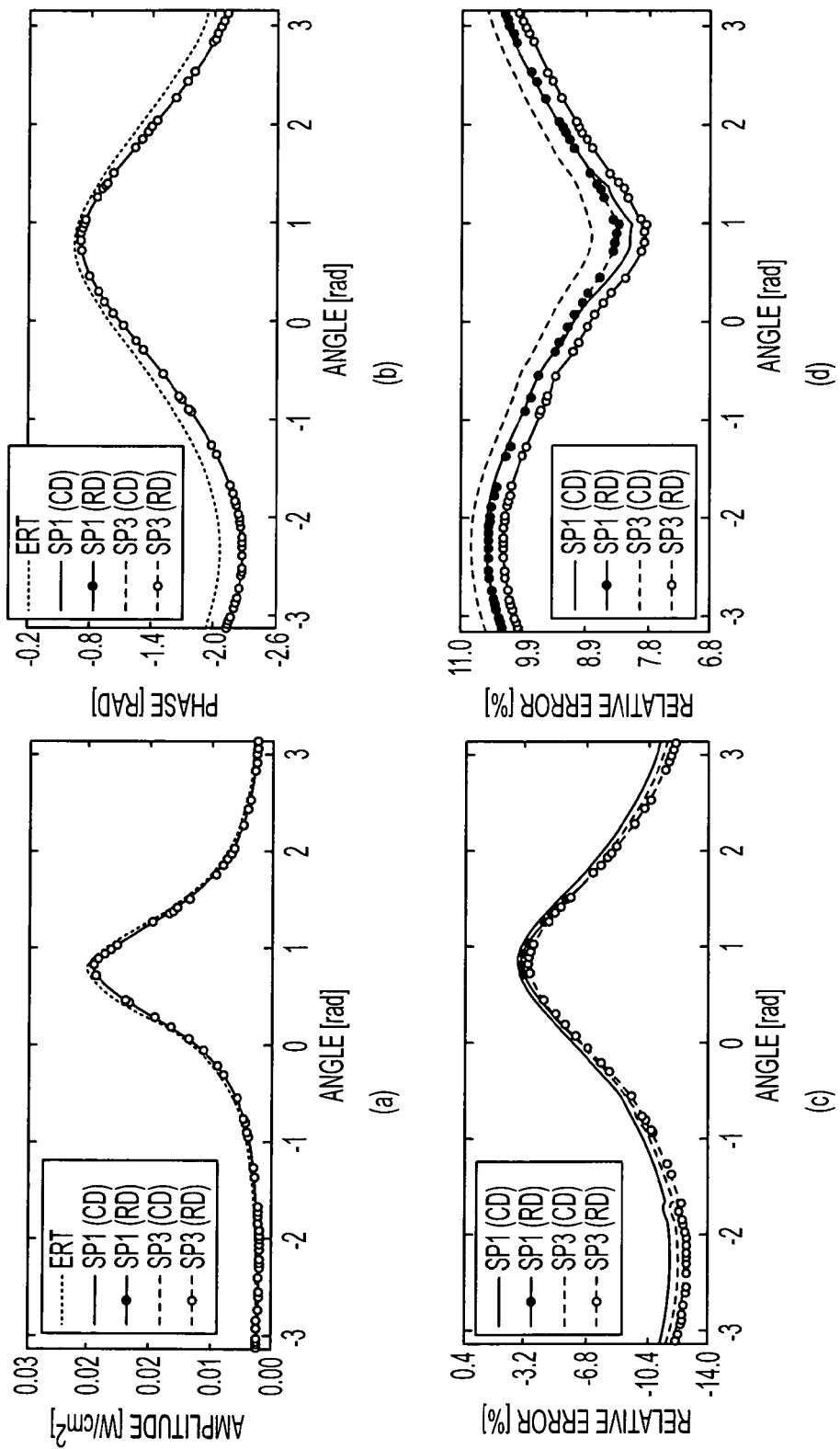
FIGS. 10A-10D are graphs of the amplitude and phase of the fluence at mesh nodes within the internal cross-section and the corresponding error for the first phantom of FIG. 5A, according to one or more embodiments of the disclosed subject matter.

FIGS. 9A-9B show plots of amplitude and phase of the partial current, $J^+(r)$, respectively, versus detector number. FIGS. 9C-9D show the error of the amplitude and phase of FIGS. 9A-9B with respect to the benchmark ERT ($S_{12}$) solution, respectively. FIGS. 10A-10B show the amplitude and phase of the fluence at mesh nodes within the internal cross-section versus angle. FIGS. 10C-10D show the error of the amplitude and phase of FIGS. 10A-10B with respect to the benchmark ERT ($S_{12}$) solution.

The partial current at the boundary can be approximated to similar accuracies by all SPN models, as shown in FIGS. 9A-9D. The average error of the amplitude of the partial current ranges from 3.85% to 4.35%. The average error between the phase of the partial current is larger, ranging from 10.09% to 10.85%. The fluence within the internal cross-section of interest also supports the observation that all SPN models exhibit similar performance in the diffuse phantom, as shown in FIGS. 10A-10D. The errors in the amplitude of the fluence from all SPN models are similar, with the average error $\tilde{\phi}_e(r)$ ranging from 8.89% to 9.68%, while the average error in the phase of the fluence ranges from 9.47% to 10.09%.

Table 7 below summarizes computation time and computing resources information for obtaining the fluence with respect to phantom using each of the models. In particular, Table 7 makes the benefits of the SPN model over the ERT model readily apparent. Relative to the computational time required to obtain the fluence with the $SP_1$ model, the $SP_3$ takes 2.06 times longer, while the ERT (S12) solution requires 184.5 times more computation time. Such results are consistent with expectations, since the $SP_3$ model results in a system of linear equations twice as large as the $SP_1$ system of equations. Analysis of the performance of the SPN models in a diffuse media reveals that they all perform similarly well in approximating the ERT.

TABLE 6

Average relative error of the fluence, $\tilde{\phi}_e(r)$, and partial current, $\tilde{J}_e^+(r)$, for phantom 1

| Model | $\tilde{\phi}_e(r)$ [%] (Amplitude) | $\tilde{\phi}_e(r)$ [%] (Phase) | $\tilde{\phi}_e(r)$ [%] (Amplitude) | $\tilde{\phi}_e(r)$ [%] (Phase) | $\tilde{J}_e^+(r)$ [%] (Amplitude) | $\tilde{J}_e^+(r)$ [%] (Phase) |
|---|---|---|---|---|---|---|
| $SP_1$ (CD) | 9.90 | 9.65 | 8.89 | 9.76 | 3.85 | 10.72 |
| $SP_1$ (RD) | 10.51 | 9.32 | 9.55 | 9.47 | 4.29 | 10.09 |
| $SP_3$ (CD) | 9.96 | 10.04 | 9.30 | 10.09 | 4.10 | 10.85 |
| $SP_3$ (RD) | 10.31 | 9.64 | 9.68 | 9.77 | 4.35 | 10.36 |

TABLE 7

Computation Time and Computing Resources for Phantom 1

| Model | Time (sec) | RAM (MB) |
|---|---|---|
| $SP_1$ (RD) | 53.5 | 172.6 |
| $SP_1$ (CD) | 76.6 | 194.3 |
| $SP_3$ (RD) | 115.9 | 313.1 |
| $SP_3$ (CD) | 150.3 | 359.4 |
| ERT ($S_{12}$) | 1,188.0 | 6,140.0 |

Numerical Study—Phantom 2: Absorbing Inclusions

Figure 5:
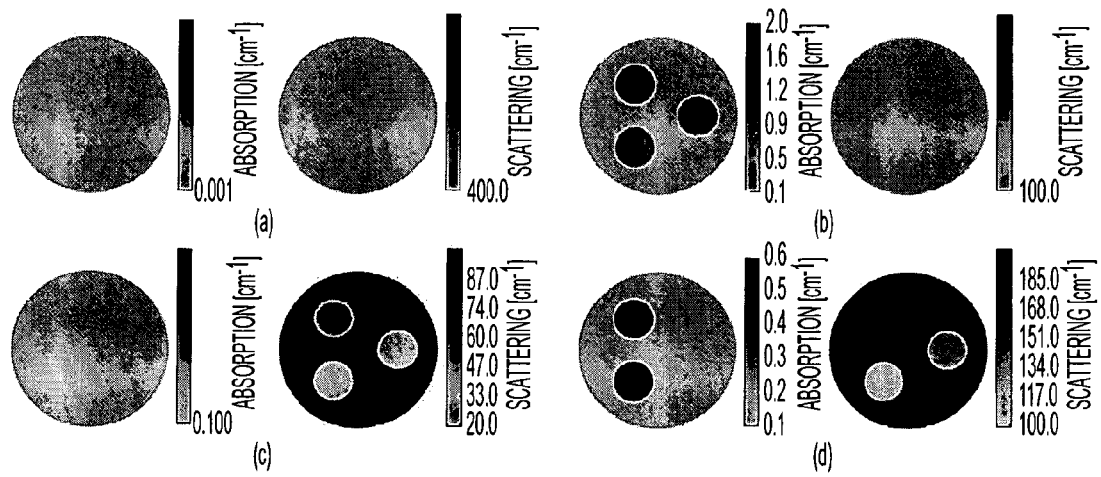
FIGS. 5A-5D show absorption and scattering features of four different phantoms, according to one or more embodiments of the disclosed subject matter.
Figure 6:
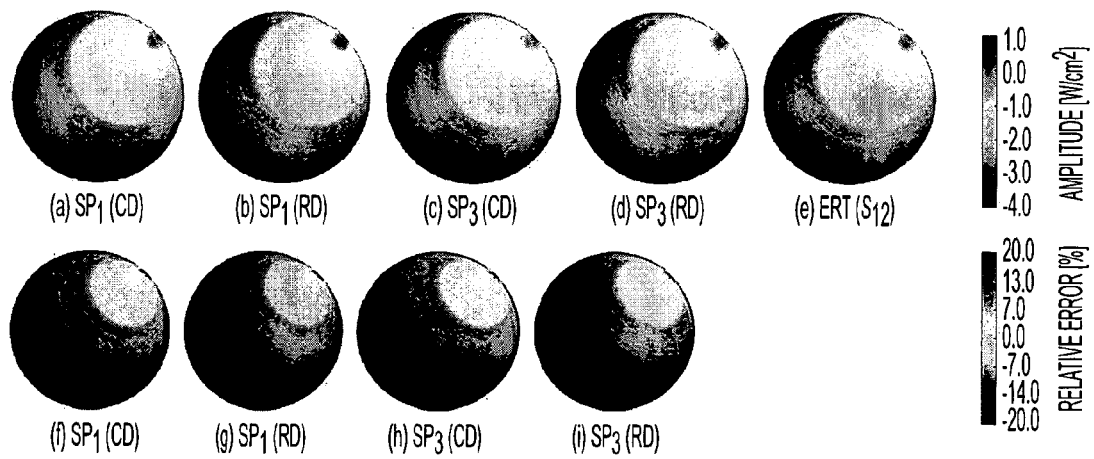
FIGS. 6A-6I show amplitude of the fluence computed using various models and corresponding error for the first phantom of FIG. 5A, according to one or more embodiments of the disclosed subject matter.
Figure 7:
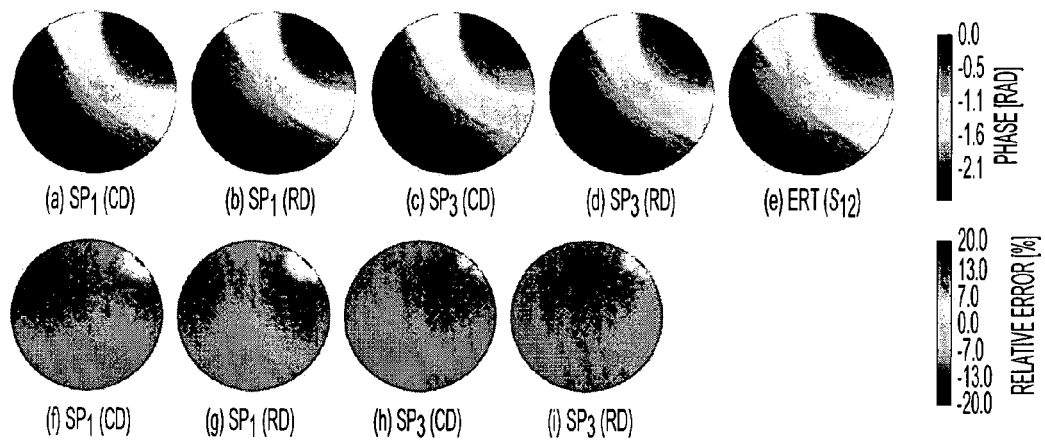
FIGS. 7A-7I show phase of the fluence computed using various models and corresponding error for the first phantom of FIG. 5A, according to one or more embodiments of the disclosed subject matter.

Results from simulations on the phantom that includes highly absorbing inclusions, as shown in FIG. 5B, are discussed below. There are three objects in the medium: two objects with $\mu_a=1.0$ cm$^{-1}$ and one object with $\mu_a=2.0$ cm$^{-1}$.

Figure 11:
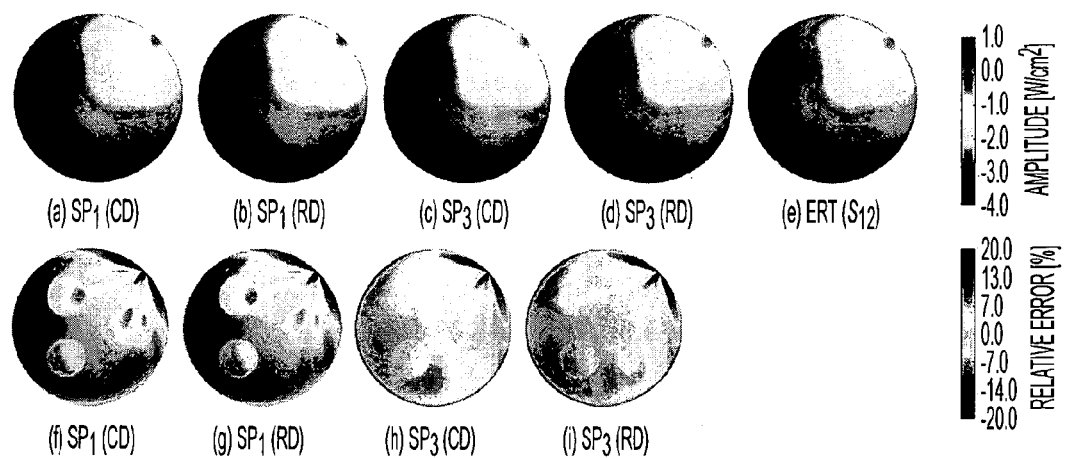
FIGS. 11A-11I show amplitude of the fluence computed using various models and corresponding error for the second phantom of FIG. 5B, according to one or more embodiments of the disclosed subject matter.
Figure 12:
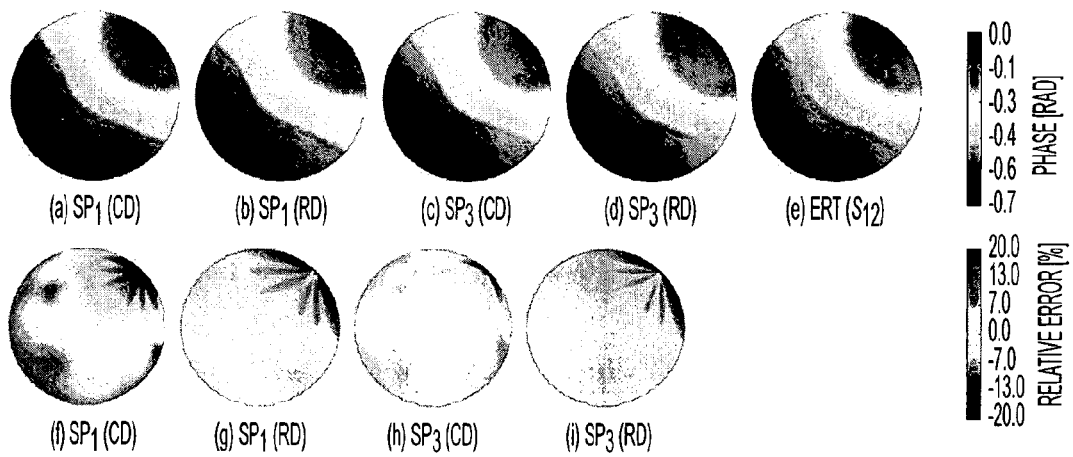
FIGS. 12A-12I show phase of the fluence computed using various models and corresponding error for the second phantom of FIG. 5B, according to one or more embodiments of the disclosed subject matter.

Images of the amplitude and the phase of the fluence computed with the SPN models and the ERT model are presented in FIGS. 11-12. Maps of the relative error between the SPN solutions and the benchmark ERT solution are also presented in these figures. In particular, FIG. 11A-11E show the amplitude of the fluence computed with the $SP_1$ (CD), the $SP_1$ (RD), the $SP_3$ (CD), the $SP_3$ (RD), and the ERT ($S_{12}$) models, respectively. FIGS. 11F-11I show the percent error at each node of FIGS. 11A-11D relative to the ERT ($S_{12}$) benchmark of FIG. 11E. Similarly, FIGS. 12A-12E show the phase of the fluence computed with the $SP_1$ (CD), the $SP_1$ (RD), the $SP_3$ (CD), the $SP_3$ (RD), and the ERT ($S_{12}$) models, respectively, and FIGS. 12F-12I show the percent error at each node of FIGS. 12A-12D relative to the ERT ($S_{12}$) benchmark of FIG. 12E. The average relative errors are summarized in Table 8.

Figure 13:
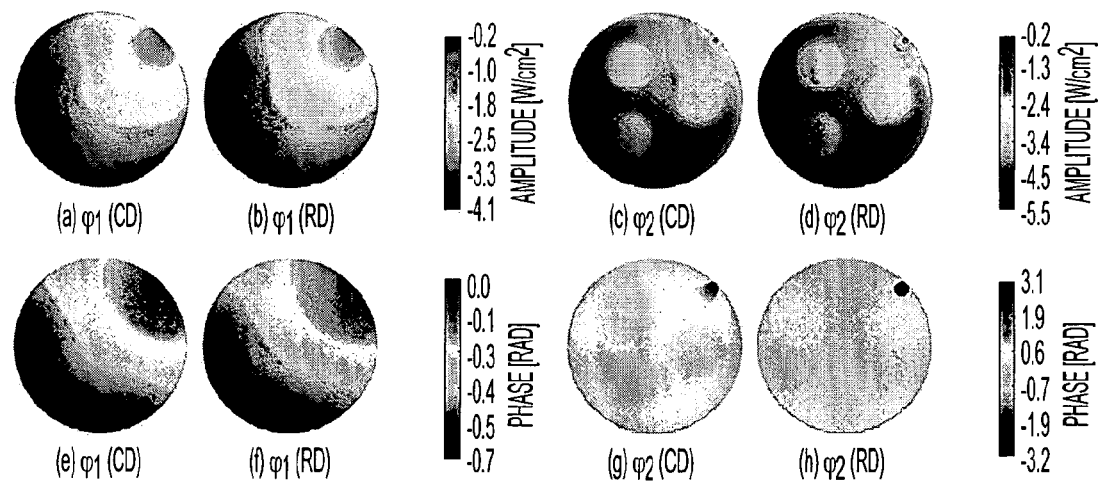
FIGS. 13A-13H show the amplitude and phase of the composite moments computed using different $SP_3$ models for the second phantom of FIG. 5B, according to one or more embodiments of the disclosed subject matter.

The individual composite moments (i.e., $\phi_1$ and $\phi_2$) of the $SP_3$ models are shown in FIGS. 13A-H. In particular, FIGS. 13A-13B represent the amplitude of the composite moment $\phi_1$ computed with the $SP_3$ (CD) and $SP_3$ (RD) models, respectively. FIGS. 13C-13D represent the amplitude of the composite moment $\phi_2$ computed with the $SP_3$ (CD) and $SP_3$ (RD) models, respectively. FIGS. 13E-13F represent the phase of the composite moment $\phi_1$ computed with the $SP_3$ (CD) and $SP_3$ (RD) models, respectively. FIGS. 13G-13H represent the phase of the composite moment $\phi_2$ computed with the $SP_3$ (CD) and $SP_3$ (RD) models, respectively.

Figure 14:
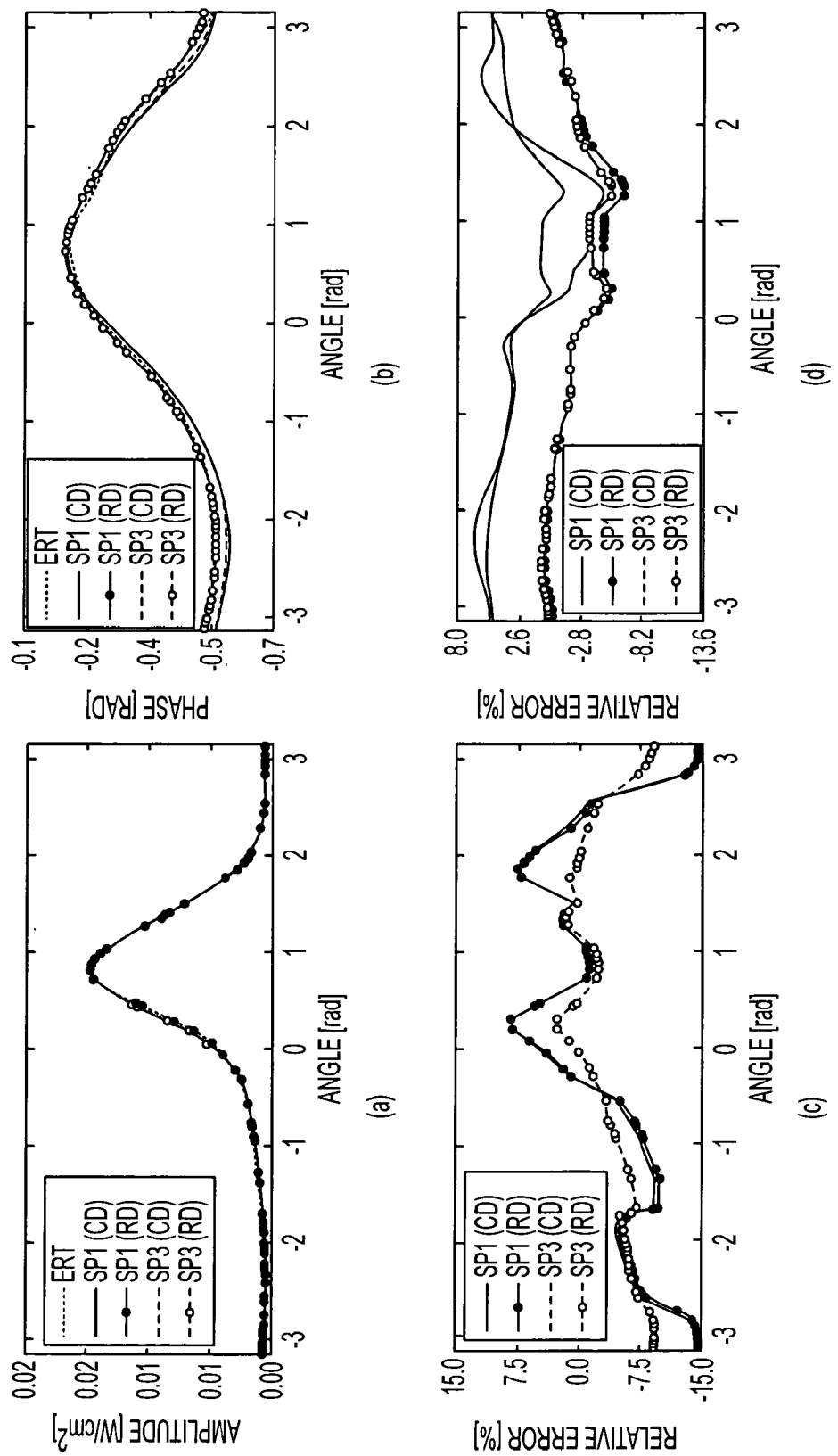
FIGS. 14A-14D are graphs of the amplitude and phase of the fluence at mesh nodes within the internal cross-section and the corresponding error for the second phantom of FIG. 5B, according to one or more embodiments of the disclosed subject matter.
Figure 15:
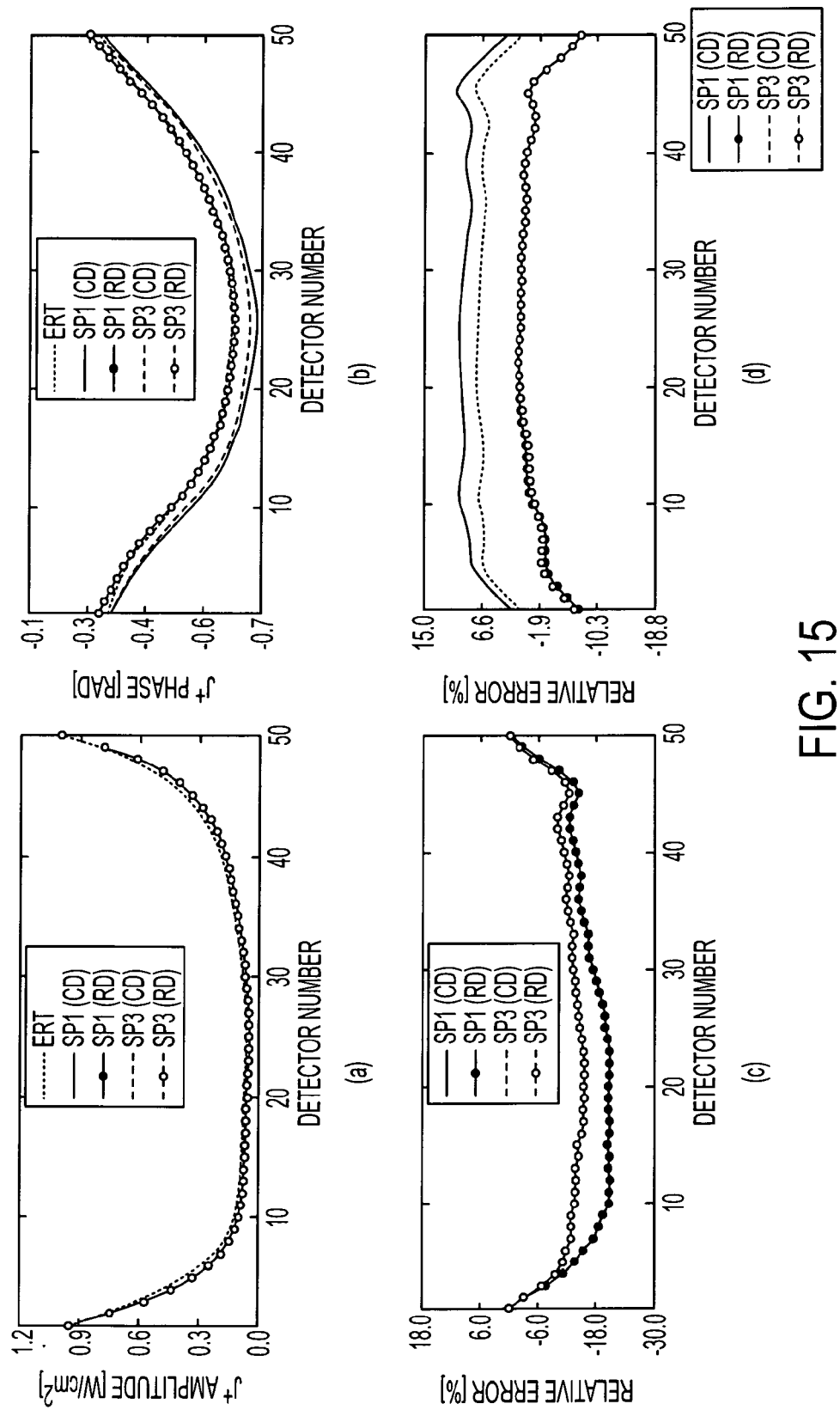
FIGS. 15A-15D are graphs of the amplitude and phase of the partial current and corresponding error for the second phantom of FIG. 5B, according to one or more embodiments of the disclosed subject matter.

FIGS. 14A-14B show the amplitude and phase of the fluence at mesh nodes within the internal cross-section versus angle. FIGS. 14C-14D show the error of the amplitude and phase of FIGS. 14A-14B with respect to the benchmark ERT ($S_{12}$) solution. FIGS. 15A-15B show the amplitude and phase of the partial current, $J^+(r)$, respectively, versus detector number. FIGS. 15C-15D show the error of the amplitude and phase of the partial current, $J_e^+(r)$ with respect to the benchmark ERT ($S_{12}$) solution, respectively.

The fluence and the relative error of the fluence (FIG. 11) show that the $SP_3$ models are significantly better than the $SP_1$ models at approximating the benchmark solution. In general, all SPN solutions exhibit large positive errors near the source (overestimation of the fluence) and negative errors far from the source (underestimation of the fluence). While both models exhibit large errors near the source, the area within which large errors occur is larger in the $SP_1$ solutions than in the $SP_3$ solutions. Similarly, the $SP_3$ solutions are more accurate approximations to the benchmark than the $SP_1$ solutions at locations far from the boundary.

Furthermore, it is clear that the $SP_3$ models are able to more accurately approximate the benchmark solution in the region of the highly absorbing inclusions, as indicated by the presence of pronounced areas of error in the $SP_1$ solutions at the location of the inclusions. The error profiles of the $SP_3$ solutions in these same regions are less pronounced, indicating that the $SP_3$ equations model light propagation in highly absorbing media more accurately than the $SP_1$ equations. Both $SP_3$ models (i.e., CD and RD) produce more accurate solutions than the two $SP_1$ models (i.e., CD and RD). Additionally, both $SP_3$ models (CD and RD) exhibit similar overall relative error in the amplitude (5.26% and 5.47%, respectively), but differ significantly in the error of the phase.

Analysis of the phase of the fluence reinforces the observation that the $SP_3$ models are better approximations to the ERT solution than the $SP_1$ models, as illustrated, for example, in FIGS. 12A-12I. All models produce phase distributions that significantly underestimate the phase near the source and moderately overestimate it far from the source. However, the area around the source within which the $SP_3$ models underestimate the source is significantly smaller than the area in which the $SP_1$ models severely understate the phase. This suggests that the "transport" regime, within which the phase accumulation of photon propagation can only be modeled by the ERT, is smaller for the $SP_3$ models than the $SP_1$ models. The pronounced areas of error that appear in the amplitude of the fluence at the location of the highly absorbing inclusions are not present in the relative error of the phase.

The average relative error of the phase of the $SP_3$ (RD) solution (2.54%) is significantly smaller than the average relative error of the phase of the $SP_3$ (CD) solution (4.27%). This observation is in contrast to the pattern observed in the amplitude of the phase, where the differences between the $SP_3$ (RD) and $SP_3$ (CD) solutions are minimal (5.47% and 5.26%, respectively). The $SP_1$ (RD) model achieves a lower average relative error of the phase (2.93%) than the $SP_3$

TABLE 8

Average relative error of the fluence, $\tilde{\phi}_e(r)$, and partial current, $\tilde{J}_e^+(r)$, for phantom 2

| Model | $\tilde{\phi}_e(r)$ [%] (Amplitude) | $\tilde{\phi}_e(r)$ [%] (Phase) | $\tilde{\phi}_e(r)$ [%] (Amplitude) | $\tilde{\phi}_e(r)$ [%] (Phase) | $\tilde{J}_e^+(r)$ [%] (Amplitude) | $\tilde{J}_e^+(r)$ [%] (Phase) |
|---|---|---|---|---|---|---|
| $SP_1$ (CD) | 8.14 | 5.44 | 4.09 | 3.15 | 15.21 | 8.68 |
| $SP_1$ (RD) | 8.51 | 2.93 | 4.62 | 1.77 | 15.53 | 1.61 |
| $SP_3$ (CD) | 5.26 | 4.27 | 3.89 | 3.46 | 11.64 | 6.27 |
| $SP_3$ (RD) | 5.47 | 2.54 | 4.15 | 1.43 | 11.82 | 1.51 |

(CD) model (4.27%), which suggests that the $SP_1$ (RD) model may be more accurate than the $SP_1$ (CD) and $SP_3$ (CD) models in modeling phase accumulation. However, the SPN (RD) solutions have a marginally bigger area of large error near the boundary when compared to the SPN (CD) solutions.

With respect to the composite moments of the radiance produced by the $SP_3$ models, as illustrated in FIGS. 13A-13H, the amplitude and the phase of the first composite moment ($\phi_1$) are similar for both CD and RD models, but there are small perturbations of the solution in the region of the inclusions. The amplitude of the second moment ($\phi_2$) is higher in the exact locations of the highly absorbing inclusions, making it exceptionally clear where the inclusions are located, as reflected in FIGS. 13C-13D. This information may be exploited to improve the image reconstruction process. For example, this knowledge may be used to dynamically increase mesh density in the areas with prominent "correction" terms (i.e., as observed in $\phi_2$).

There are also differences observed between the CD and RD models in the phase of $\phi_2$, as the location of the absorbing inclusions are visible in $\phi_2$ (CD) but not in $\phi_2$ (RD), as illustrated in FIGS. 13G-13H. The value of $\phi_2$ (CD) near the source is much larger than the values at the same locations of $\phi_2$ (RD). This strong "correction" near the boundary may be responsible for improved accuracy in the phase of the fluence computed with the $SP_3$ (CD) model at mesh nodes near the source. However, the strong "correction" in the interior of the $\phi_2$ (CD) solution may also be the reason why mesh nodes far from the source see an increase in error in the phase of the fluence computed with the $SP_3$ (CD) model. Thus, while $\phi_2$ (CD) correction terms result in a reduction of the error in the phase of the fluence near the boundary, they may also be responsible for the increase in error in the phase of the fluence far from the boundary.

Referring to FIGS. 14A-14D, when comparing the fluence along the internal cross-section, it is apparent that both $SP_3$ (CD and RD) models are better approximations to the amplitude of the benchmark solution than the $SP_1$ models, with insignificant differences between the RD and CD models. In the case of the phase of the fluence, however, the $SP_1$ (RD) and $SP_3$ (RD) models are a better approximation than either the $SP_1$ (CD) or $SP_3$ (CD) models. Similarly, comparing the partial current at the boundary as shown in FIGS. 15A-15D yields the conclusion that the $SP_3$ models (CD and RD) predict the amplitude of $J^+(r)$ more accurately that the $SP_1$ models. However, the $SP_1$ (RD) and $SP_3$ (RD) models are better at approximating the phase of $J^+(r)$ than the $SP_1$ (CD) and $SP_3$ (CD) models.

As summarized in Table 9 below, the SPN models enjoy a clear advantage in terms of computation time and memory requirements as compared to the ERT model. The computation time required to obtain the fluence using the SPN (RD) models is significantly lower than the time required by the SPN (CD) models (approximately 40% lower). The increase in computation time (and memory requirements) for SPN (CD) is expected as all entries of the forward model operator A are complex-valued, while only the main diagonal and some off-diagonal elements are complex-valued in the RD system.

Overall, the $SP_3$ (RD) model may perform better than the other SPN models. Furthermore, the $SP_1$ (RD) model may be more accurate than the $SP_1$ (CD) and $SP_3$ (CD) model on approximating the phase of the benchmark fluence and partial current values, at least with respect to samples having similar properties as Phantom 2.

TABLE 9

Computation Time and Computing Resources for Phantom 2

| Model | Time (sec) | RAM (MB) |
|---|---|---|
| $SP_1$ (RD) | 30.9 | 172.6 |
| $SP_1$ (CD) | 49.1 | 194.3 |
| $SP_3$ (RD) | 63.2 | 313.1 |
| $SP_3$ (CD) | 100.1 | 359.4 |
| ERT ($S_{12}$) | 4,819.3 | 6,140.0 |

Numerical Study—Phantom 3: Scattering Inclusions

Results from simulations on the phantom with areas of low scattering values, as shown in FIG. 5C, are discussed below. There are three objects in the medium: two objects with $\mu_s=20.0$ cm$^{-1}$ and one object with $\mu_s=60.0$ cm$^{-1}$.

Figure 16:
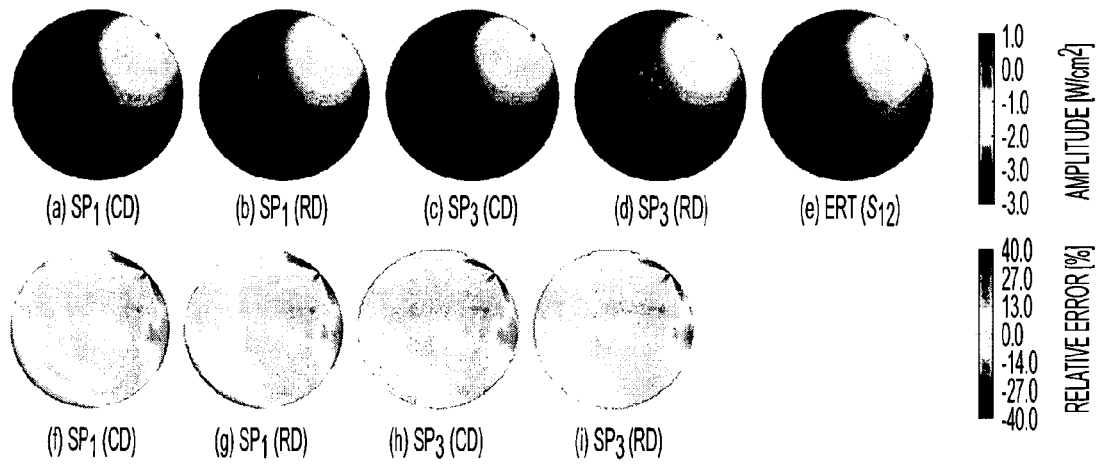
FIGS. 16A-16I show amplitude of the fluence computed using various models and corresponding error for the third phantom of FIG. 5C, according to one or more embodiments of the disclosed subject matter.
Figure 17:
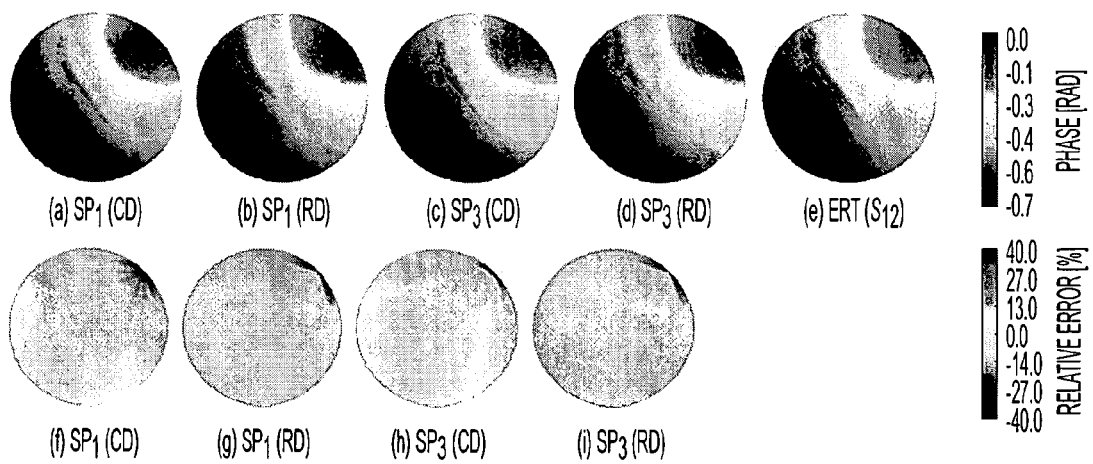
FIGS. 17A-17I show phase of the fluence computed using various models and corresponding error for the third phantom of FIG. 5C, according to one or more embodiments of the disclosed subject matter.

Images of the amplitude and the phase of the fluence computed with the SPN models and the ERT model are presented in FIGS. 16-17. Maps of the relative error between the SPN solutions and the benchmark ERT solution are also presented in these figures. In particular, FIG. 16A-16E show the amplitude of the fluence computed with the $SP_1$ (CD), the $SP_1$ (RD), the $SP_3$ (CD), the $SP_3$ (RD), and the ERT ($S_{12}$) models, respectively. FIGS. 16F-16I show the percent error at each node of FIGS. 16A-16D relative to the ERT ($S_{12}$) benchmark of FIG. 16E. Similarly, FIGS. 17A-17E show the phase of the fluence computed with the $SP_1$ (CD), the $SP_1$ (RD), the $SP_3$ (CD), the $SP_3$ (RD), and the ERT ($S_{12}$) models, respectively, and FIGS. 17F-17I show the percent error at each node of FIGS. 17A-17D relative to the ERT ($S_{12}$) benchmark of FIG. 17E. The average relative errors are summarized in Table 10.

Figure 18:
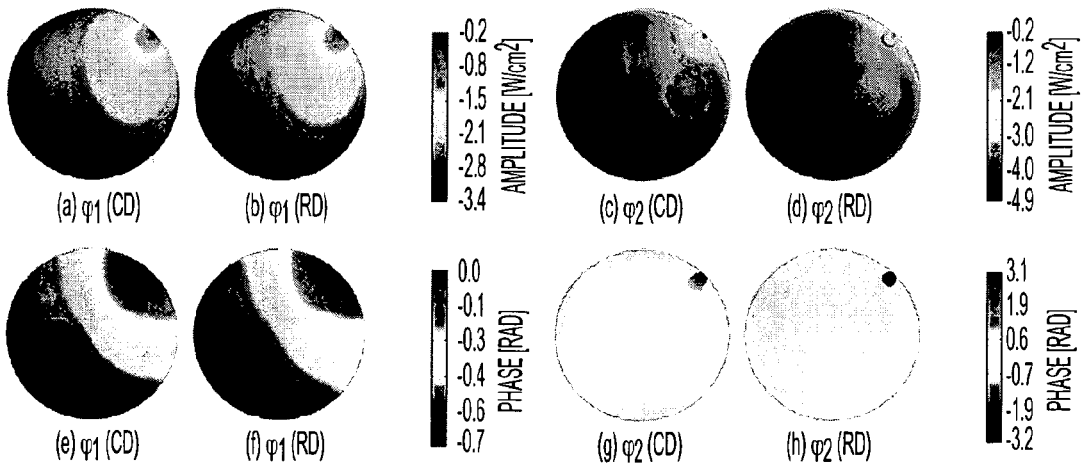
FIGS. 18A-18H show the amplitude and phase of the composite moments computed using different $SP_3$ models for the third phantom of FIG. 5C, according to one or more embodiments of the disclosed subject matter.

The individual composite moments (i.e., $\phi_1$ and $\phi_2$) of the $SP_3$ models are shown in FIGS. 18A-H. In particular, FIGS. 18A-18B represent the amplitude of the composite moment $\phi_1$ computed with the $SP_3$ (CD) and $SP_3$ (RD) models, respectively. FIGS. 18C-18D represent the amplitude of the composite moment $\phi_2$ computed with the $SP_3$ (CD) and $SP_3$ (RD) models, respectively. FIGS. 18E-18F represent the phase of the composite moment $\phi_1$ computed with the $SP_3$ (CD) and $SP_3$ (RD) models, respectively. FIGS. 18G-18H represent the phase of the composite moment $\phi_2$ computed with the $SP_3$ (CD) and $SP_3$ (RD) models, respectively.

Figure 19:
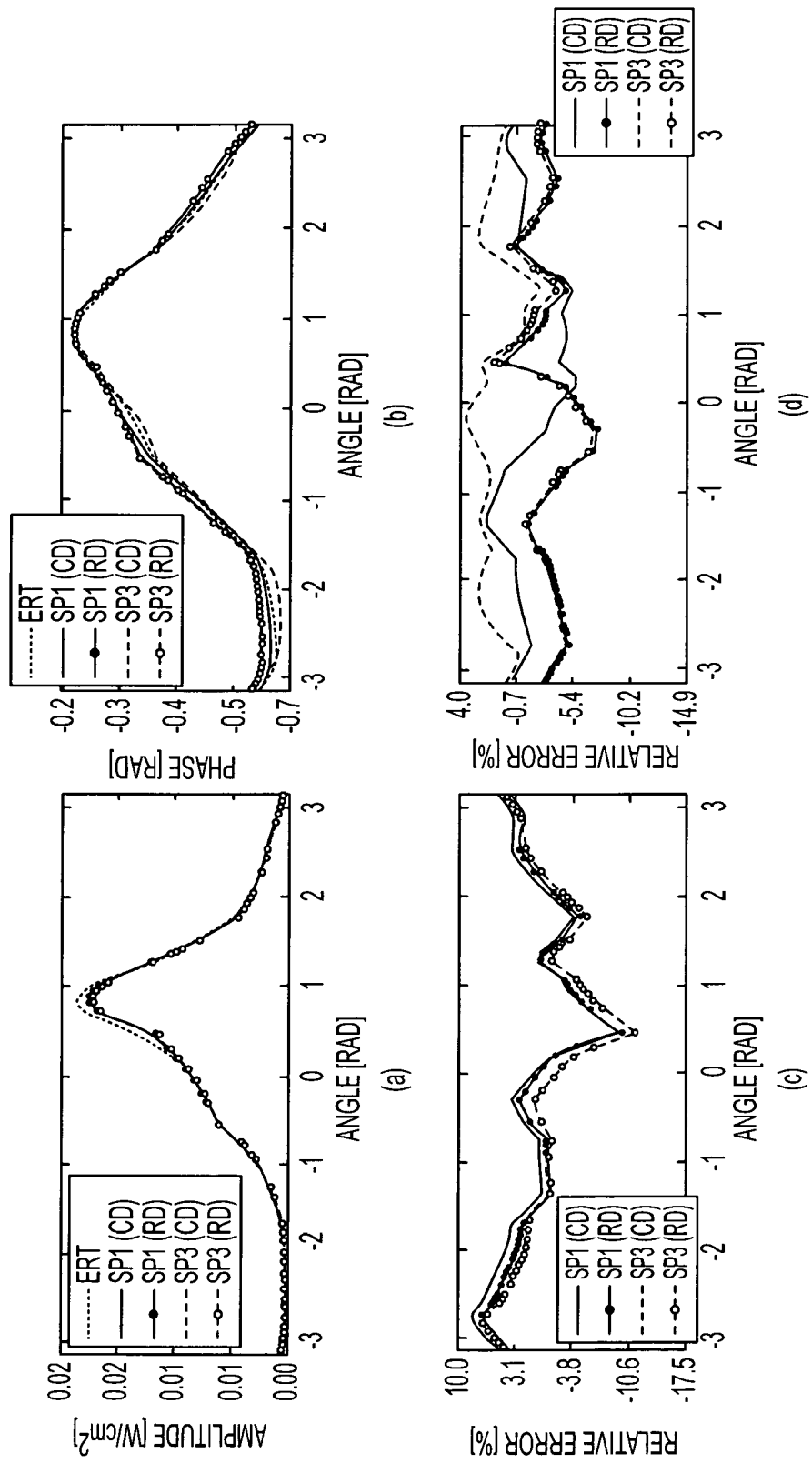
FIGS. 19A-19D are graphs of the amplitude and phase of the fluence at mesh nodes within the internal cross-section and the corresponding error for the third phantom of FIG. 5C, according to one or more embodiments of the disclosed subject matter.
Figure 20:
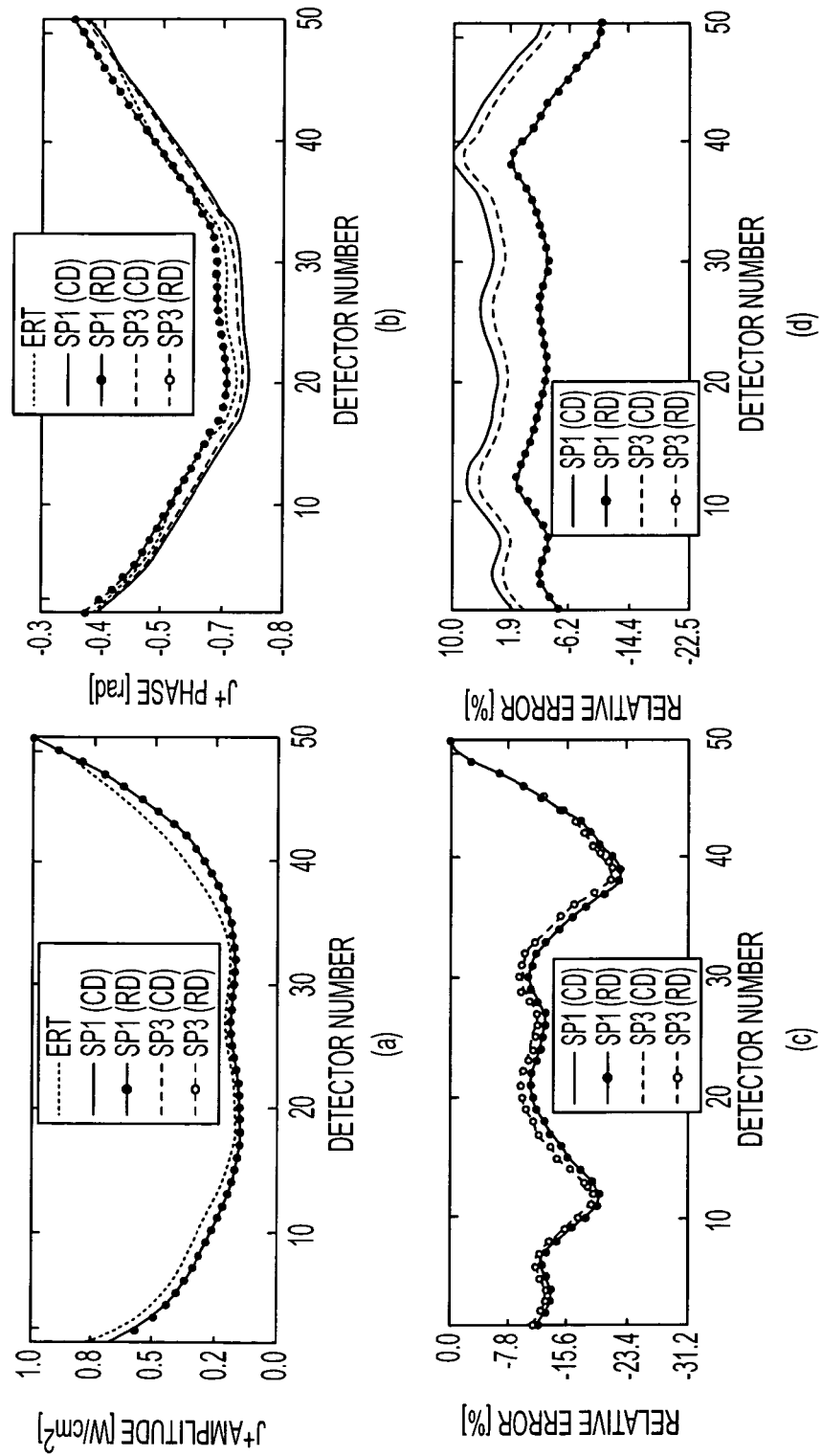
FIGS. 20A-20D are graphs of the amplitude and phase of the partial current and corresponding error for the third phantom of FIG. 5C, according to one or more embodiments of the disclosed subject matter.

FIGS. 19A-19B show the amplitude and phase of the fluence at mesh nodes within the internal cross-section versus angle. FIGS. 19C-19D show the error of the amplitude and phase of FIGS. 19A-19B with respect to the benchmark ERT ($S_{12}$) solution. FIGS. 20A-20B show the amplitude and phase of the partial current, $J^+(r)$, respectively, versus detector number. FIGS. 20C-20D show the error of the amplitude and phase of the partial current, $J_e^+(r)$ with respect to the benchmark ERT ($S_{12}$) solution, respectively.

TABLE 10

Average relative error of the fluence, $\tilde{\phi}_e(r)$, and partial current, $\tilde{J}_e^+(r)$, for phantom 3

| Model | $\tilde{\phi}_e(r)$ [%] (Amplitude) | $\tilde{\phi}_e(r)$ [%] (Phase) | $\tilde{\phi}_e(r)$ [%] (Amplitude) | $\tilde{\phi}_e(r)$ [%] (Phase) | $\tilde{J}_e^+(r)$ [%] (Amplitude) | $\tilde{J}_e^+(r)$ [%] (Phase) |
|---|---|---|---|---|---|---|
| SP$_1$ (CD) | 5.45 | 3.56 | 2.07 | 1.65 | 13.27 | 5.00 |
| SP$_1$ (RD) | 4.99 | 4.28 | 1.10 | 3.54 | 13.79 | 3.09 |
| SP$_3$ (CD) | 4.87 | 2.67 | 0.67 | 1.09 | 12.56 | 3.74 |
| SP$_3$ (RD) | 4.69 | 3.94 | 0.27 | 3.20 | 12.88 | 3.04 |

With respect to phantom 3, the SP$_3$ models perform better than the SP$_1$ models. The error in the amplitude of the fluence obtained with both SP$_3$ models is similar (4.87% and 4.69%, respectively). However, the SP$_3$ (CD) models yield solutions with lower relative error in the phase of the fluence (2.67%) compared to the SP$_3$ (RD) model (3.94%). All SPN solutions have large errors in the amplitude and the phase of the fluence near the source. The amplitude of the fluence is generally overestimated near the source, as shown, for example, in FIGS. 16A-16I, while the phase is underestimated at these same locations, as shown, for example, in FIGS. 17A-17I. Compared to the SP$_3$ solutions, the amplitude of the SP$_1$ solutions exhibit large positive errors across a larger area near the source. In addition, the amplitude of the SP$_1$ solutions are overestimated at the boundary directly opposite the source.

The amplitude and phase of the first moment $\phi_1$ is similar between the SP$_3$ (CD) and SP$_3$ (RD) models. However, there are significant differences between the phase profiles of $\phi_2$. The fluence along the internal cross-section of interest and the partial current, as illustrated in FIGS. 19A-19D and FIGS. 20A-20D, respectively, support these observations. The scattering inclusions are identifiable in the images of the amplitude of $\phi_2$ (see FIGS. 18C-18D). Yet, the scattering inclusions are not identifiable in the images of the phase of $\phi_2$ (see FIGS. 18G-18H). The contrast at the site of the scattering inclusions is lower than the contrast at the site of the absorbing inclusions considered in the second phantom, particularly in the amplitude images of FIGS. 13C-D.

At least for phantom 3, the SP$_3$ models outperform the SP$_1$ models. The SP$_3$ (RD) model is better than the SP$_3$ (CD) model at approximating the phase of the fluence and partial current. However, the SP$_3$ (CD) model is better at approximating the amplitude of the benchmark solutions. Moreover, the computation times required to obtain the fluence using the SPN (RD) models are approximately 70% lower than the time required by the SPN (CD) models (Table 8.10). Table 11 below summarizes computation time and memory requirements of the SPN and ERT models for phantom 3. The increase in computation time (and memory requirements) associated with solving the SPN (CD) equations is larger than what is observed when only highly absorbing inclusions are considered.

TABLE 11

Computation Time and Computing Resources for Phantom 3

| Model | Time (sec) | RAM (MB) |
|---|---|---|
| SP$_1$ (RD) | 99.6 | 176.6 |
| SP$_1$ (CD) | 333.2 | 194.3 |
| SP$_3$ (RD) | 205.8 | 313.1 |
| SP$_3$ (CD) | 684.6 | 359.4 |
| ERT (S$_{12}$) | 7,816.4 | 6,140.0 |

Numerical Study—Phantom 4: Absorbing and Scattering Inclusions

Results from simulations on the fourth phantom, which contains absorbing and void-like inclusions, as shown in FIG. 5D, are discussed below. There are four objects in the medium: two objects with $\mu_a=0.6$ cm$^{-1}$ and two objects with $\mu_s=100.0$ cm$^{-1}$.

Figure 21:
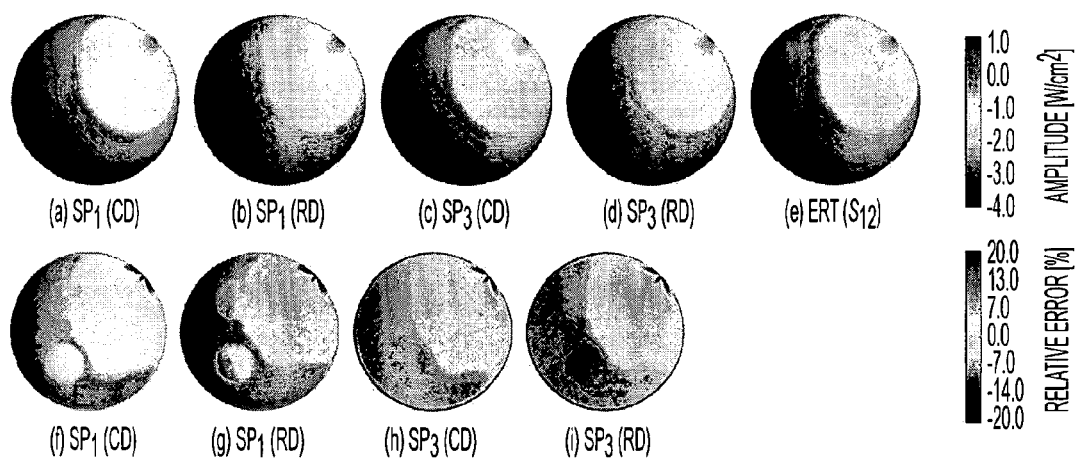
FIGS. 21A-21I show amplitude of the fluence computed using various models and corresponding error for the fourth phantom of FIG. 5D, according to one or more embodiments of the disclosed subject matter.
Figure 22:
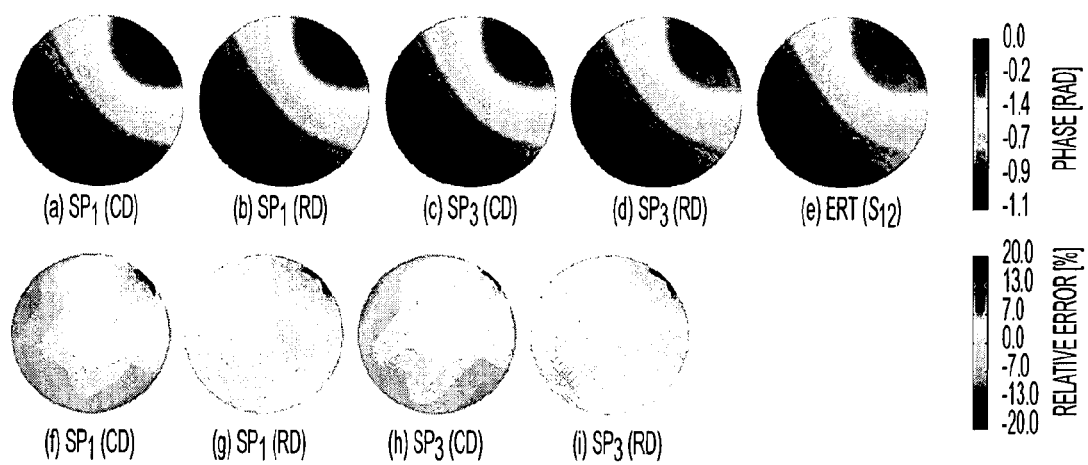
FIGS. 22A-22I show phase of the fluence computed using various models and corresponding error for the fourth phantom of FIG. 5D, according to one or more embodiments of the disclosed subject matter.

Images of the amplitude and the phase of the fluence computed with the SPN models and the ERT model are presented in FIGS. 21-22. Maps of the relative error between the SPN solutions and the benchmark ERT solution are also presented in these figures. In particular, FIG. 21A-21E show the amplitude of the fluence computed with the SP$_1$ (CD), the SP$_1$ (RD), the SP$_3$ (CD), the SP$_3$ (RD), and the ERT (S$_{12}$) models, respectively. FIGS. 21F-21I show the percent error at each node of FIGS. 21A-21D relative to the ERT (S$_{12}$) benchmark of FIG. 21E. Similarly, FIGS. 22A-22E show the phase of the fluence computed with the SP$_1$ (CD), the SP$_1$ (RD), the SP$_3$ (CD), the SP$_3$ (RD), and the ERT (S$_{12}$) models, respectively, and FIGS. 22F-22I show the percent error at each node of FIGS. 22A-22D relative to the ERT (S$_{12}$) benchmark of FIG. 22E. The average relative errors are summarized in Table 12.

Figure 23:
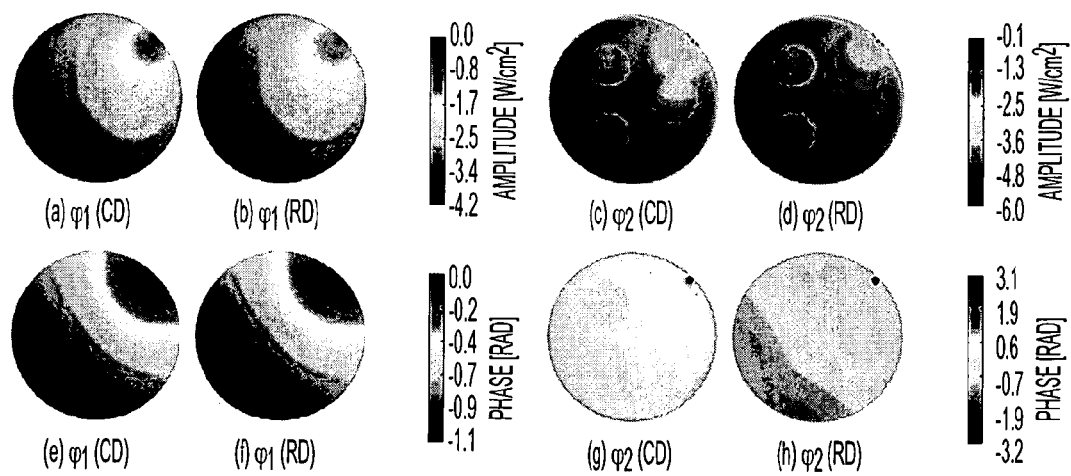
FIGS. 23A-23H show the amplitude and phase of the composite moments computed using different $SP_3$ models for the fourth phantom of FIG. 5D, according to one or more embodiments of the disclosed subject matter.

The individual composite moments (i.e., $\phi_1$ and $\phi_2$) of the SP$_3$ models are shown in FIGS. 23A-H. In particular, FIGS. 23A-23B represent the amplitude of the composite moment $\phi_1$ computed with the SP$_3$ (CD) and SP$_3$ (RD) models, respectively. FIGS. 23C-23D represent the amplitude of the composite moment $\phi_2$ computed with the SP$_3$ (CD) and SP$_3$ (RD) models, respectively. FIGS. 23E-23F represent the phase of the composite moment $\phi_1$ computed with the SP$_3$ (CD) and SP$_3$ (RD) models, respectively. FIGS. 23G-23H represent the phase of the composite moment $\phi_2$ computed with the SP$_3$ (CD) and SP$_3$ (RD) models, respectively.

Figure 24:
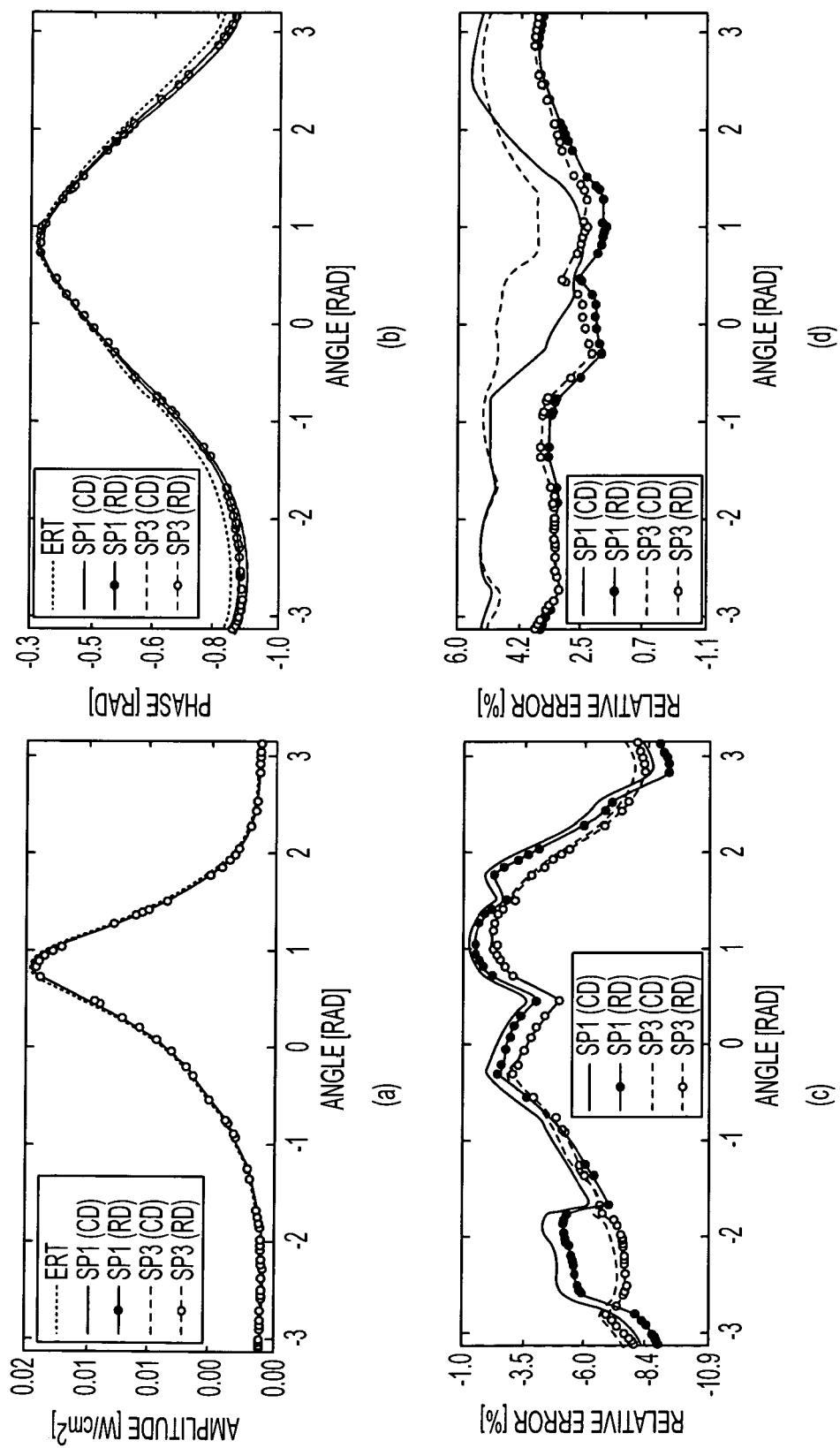
FIGS. 24A-24D are graphs of the amplitude and phase of the fluence at mesh nodes within the internal cross-section and the corresponding error for the fourth phantom of FIG. 5D, according to one or more embodiments of the disclosed subject matter.
Figure 25:
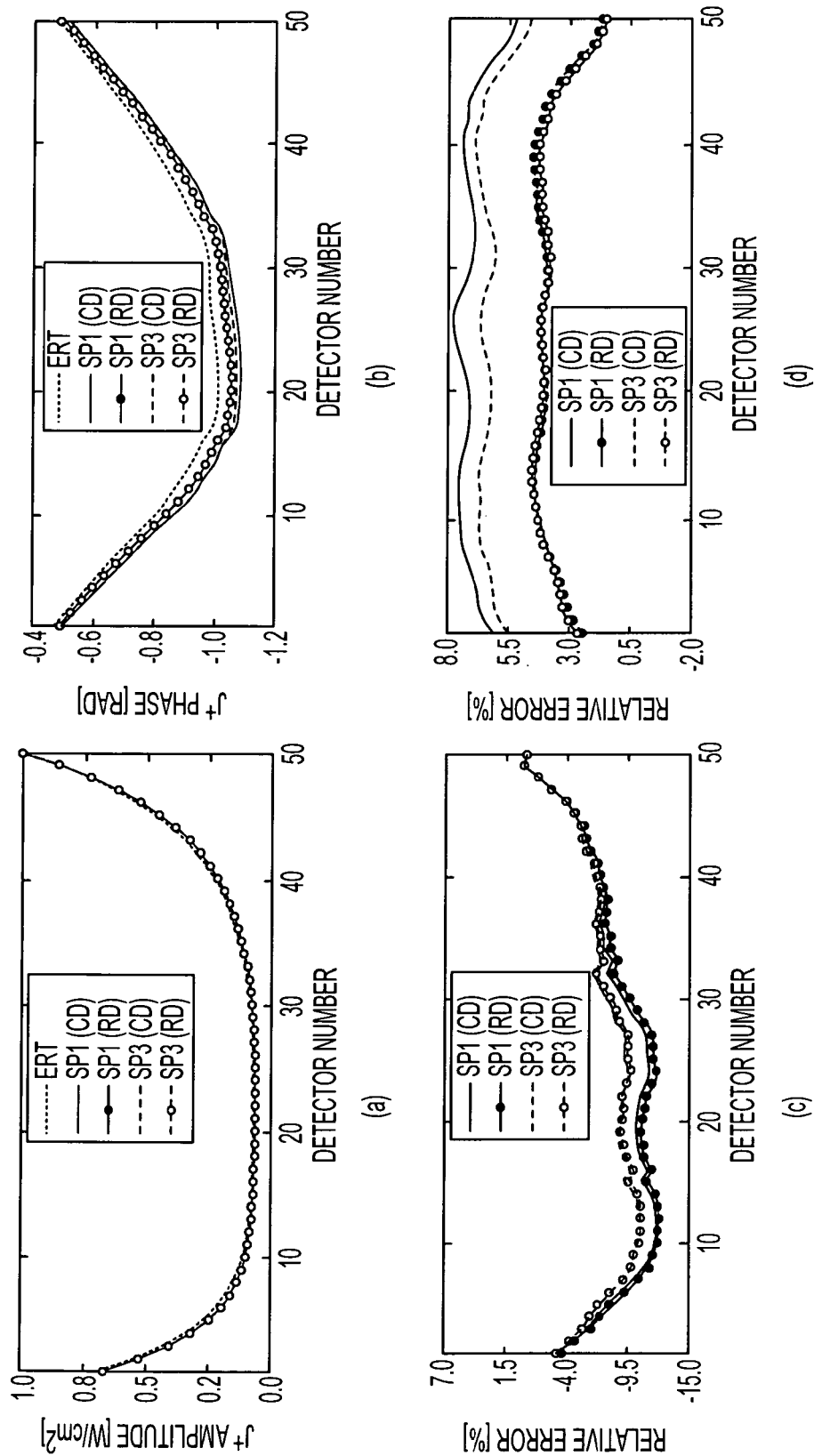
FIGS. 25A-25D are graphs of the amplitude and phase of the partial current and corresponding error for the fourth phantom of FIG. 5D, according to one or more embodiments of the disclosed subject matter.

FIGS. 24A-24B show the amplitude and phase of the fluence at mesh nodes within the internal cross-section versus angle. FIGS. 24C-24D show the error of the amplitude and phase of FIGS. 19A-19B with respect to the benchmark ERT (S$_{12}$) solution. FIGS. 25A-25B show the amplitude and phase of the partial current, J$^+$(r), respectively, versus detector number. FIGS. 25C-25D show the error of the amplitude and phase of the partial current, J$_e^+$(r) with respect to the benchmark ERT (S$_{12}$) solution, respectively.

TABLE 12

Average relative error of the fluence, $\tilde{\phi}_e(r)$, and partial current, $\tilde{J}_e^+(r)$, for phantom 4

| Model | $\tilde{\phi}_e(r)$ [%] (Amplitude) | $\tilde{\phi}_e(r)$ [%] (Phase) | $\tilde{\phi}_e(r)$ [%] (Amplitude) | $\tilde{\phi}_e(r)$ [%] (Phase) | $\tilde{J}_e^+(r)$ [%] (Amplitude) | $\tilde{J}_e^+(r)$ [%] (Phase) |
|---|---|---|---|---|---|---|
| SP$_1$ (CD) | 5.84 | 4.89 | 5.10 | 4.60 | 7.88 | 7.06 |
| SP$_1$ (RD) | 6.38 | 3.13 | 5.18 | 3.01 | 8.21 | 3.76 |
| SP$_3$ (CD) | 5.72 | 5.02 | 5.53 | 4.95 | 6.80 | 6.29 |
| SP$_3$ (RD) | 6.01 | 3.28 | 5.83 | 3.22 | 7.01 | 3.67 |

For at least phantom 4, all of the SPN models approximate the amplitude of the ERT solution with similar accuracy. The SPN (CD) models are marginally more accurate than the SPN (RD) models, as illustrated, for example, in FIGS. 21A-21I. However, the SPN (RD) models perform significantly better than the SPN (CD) models in approximating the phase of the benchmark solution, as illustrated, for example, in FIGS. 22A-22I. The same trends are evident in the amplitude and the phase of the fluence along the internal cross-section of interest, as illustrated in FIGS. 24A-24D, and in the amplitude and the phase of the partial current, as illustrated in FIGS. 25A-25C. The SP$_3$ models approximate the benchmark partial current more accurately than their corresponding SP$_1$ models. However, the SP$_3$ (CD) model yields the most accurate amplitude of the partial current, while the SP$_3$ (RD) model best approximates the phase of the partial current.

The location of the absorbing objects are clearly visible in the phase of $\phi_2$, as illustrated, for example, in FIGS. 23A-23(H). Thus, while scattering and absorbing inclusions are undifferentiated in the amplitude of $\phi_2$, the phase of $\phi_2$ clearly differentiates between the absorption and the scattering coefficients values in the inclusions. The amplitude and the phase of the first moment $\phi_1$ are similar for both CD and RD models, with the appearance of small perturbations of the solution in the region of the inclusions.

The SPN (RD) models require less computation time compared to the SPN (CD) models. Table 13 below summarizes computation time and memory requirements of the SPN and ERT models for phantom 4. Furthermore, the SPN (RD) models require less RAM than the SPN (CD) models during the execution of the algorithm. The benefit of using any of the SPN models is clear when considering the computation time and the memory requirements associated with using the ERT S$_{12}$ model.

TABLE 13

Computation Time and Computing Resources for Phantom 4

| Model | Time (sec) | RAM (MB) |
|---|---|---|
| SP$_1$ (RD) | 44.5 | 176.6 |
| SP$_1$ (CD) | 70.7 | 194.3 |
| SP$_3$ (RD) | 113.1 | 313.1 |
| SP$_3$ (CD) | 155.1 | 359.4 |
| ERT (S$_{12}$) | 6,715.4 | 6,140.0 |

When considering the simulation results for all of the phantoms, overall the SP$_3$ model is better at approximating the non-diffuse properties of light propagation throughout the entire phantom as compared to the SP$_1$, and in particular at distances near the source. The SP$_3$ solution can better approximate the "transport" behavior of photons at short distances from the source. The first composite moment $\phi_1$ is a close approximation to the final fluence value, but to account for "transport" properties, $\phi_1$ is "corrected" by $\phi_2$, particularly near the source. It is this correction that can lead to improved solutions by using the SP$_3$ model. However, embodiments of the disclosed subject matter are not limited to the use of the SP$_3$ model over the SP$_1$ model. Rather, various values of N in the SPN model can be used according to one or more contemplated embodiments.

The differences between the two SPN models (CD and RD) can be illustrated with respect to the phase of the fluence. The SPN (RD) models can more accurately approximate the phase of the fluence and the phase of the partial current than the SPN (CD) models. In contrast, the SPN (CD) models only marginally outperform the SPN (RD) models in approximating the amplitudes of the fluence and the partial current. Thus, the SPN (RD) model can be used over the SPN (CD) model since both models can approximate the amplitude to similar degrees of accuracy, but the SPN (RD) model is substantially better at approximating the phase values of the fluence and the partial current. In addition, the SPN (RD) model requires lower computation times compared to the SPN (CD) model, the SP$_3$ (RD) model is significantly better at approximating the benchmark solutions than the SP$_1$ (RD) model. However, embodiments of the disclosed subject matter are not limited to the use of the SPN (RD) model over the SPN (CD) model. Rather, the SPN (CD) may be used over the SPN (RD) model or used in conjunction with the SPN (RD) model for certain applications, according to one or more contemplated embodiments. For illustrative purposes, the SPN (RD) model, referred to simply as the SPN model below, is discussed with respect to an algorithm for performing reconstructions of absorption and scattering coefficients.

Finite Volume SPN Model: Inverse Problem

The image reconstruction step in DOT refers to the process of solving an inverse problem to "reconstruct" unknown tissue properties from the data, such as photon counts measured with CCD cameras or optical fibers connected to photodiodes. Tissue properties of interest typically include $\mu'_a$ and $\mu_s$, but more generally, may include any variable that appears in the forward model. The variable or variables to reconstruct are denoted simply as $\mu$. Due to the inability to directly invert the forward model, the reconstruction step can be a large-scale optimization process, where the goal is to find the optical properties that minimize an objective function that measures the error between simulated detector readings generated with the forward model and the experimentally measured data.

In other words, given the understanding of the light probing the tissue (O), the value and distribution of $\mu$ inside the medium that leads to the experimentally measured data M can be determined. Assuming a forward model F($\mu$) that mathematically describes the way in which light propagates through tissue and can produce "simulated" detector measurements P, analogous to M, then an objective function $f(\mu)$ can be constructed that quantifies how well P, produced by $F(\mu)$, compares to M. Then, the goal is to find the value of $\mu$ that minimizes $f(\mu)$, which, in turn, also minimizes the mismatch between P and M.

The objective function can be the least-squares cost function, which minimizes the residual sum of the squared error and is given by:

$$f(\mu, u) = \frac{1}{2}(M - P)^T \overline{(M - P)}. \quad (9.1)$$

Here $\overline{(\cdot)}$ represents the complex conjugate of $(\cdot)$ and P is the projection of the solution u of the forward problem (i.e., the fluence or the radiance intensity) onto the detectors, such that:

$$P = Qu. \quad (9.2)$$

Q is a projection operator that maps the solution to the forward problem u onto boundary detectors as above. P is the partial current at the boundary, $J^+(r, \omega)$, where r denotes spatial position and $\omega$ is the modulation frequency of the source. The optimization problem to find the value of $\mu$ that minimizes Eqn. 9.1 can be written in its most general form as the following PDE-constrained quadratic problem:

$$\min f(\mu, u) = \frac{1}{2}(M - Qu)^T \overline{(M - Qu)}, \quad (9.3)$$
$$\text{subject to } c(\mu, u) = A(\mu) - b = 0.$$

The operator matrix A and vector b represent the discretized version of the FD-SPN model. The problem in Eqn. 9.3 is referred to as an "equality-constrained" optimization problem because it requires an accurate solution of the forward problem, i.e., $A(\mu)u-b$.

Either an "unconstrained" optimization method or a partial-differential equation constrained (PDE-constrained) optimization method can be employed to solve Eqn. 9.3 The principal difference between the two methods lies in how dependencies between $\mu$ and u are treated. The PDE-constrained method can yield significant improvements in computational efficiency compared to the unconstrained method; however, this gain comes at a cost of increased algorithm complexity that may cause challenges in implementation.

With either method, the goal is to solve a quadratic problem, which involves the computation of the first and second order derivatives of the objective function, e.g., Eqn. 9.1, with respect to all independent variables (i.e., $\mu$ for the unconstrained method or u and $\mu$ for the PDE-constrained method). Indeed, in the unconstrained formulation, the forward variable is a function of the inverse variable such that $u(\mu)$, whereas in the PDE-constrained formulation, both u and $\mu$ are independent variables. This procedure can be time consuming and impractical for optimization problems of even moderate size, but numerical techniques for solving these types of quadratic problems can be employed in order to obtain the inverse solutions in an efficient manner. In particular, the challenges associated with computing the gradient of the objective function can be overcome by making use of the adjoint equation to the forward problem, which allows calculation of the gradient at the computational cost of solving one forward problem.

The challenges of computing the Hessian matrix, H, can be addressed through the use of the limited-memory Broyden-Fletcher-Goldfarb-Shanno (L-BFGS) algorithm. L-BFGS is a type of quasi-Newton optimization algorithm that addresses the computational burden associated with computing H of $f(\mu)$ by using an approximate Hessian matrix B that can be explicitly computed more easily. Furthermore, with the L-BFGS algorithm the explicit computation of B can be avoided altogether. Instead, only the product of $B^{-1}$ and its associated vectors need to be stored and updated for the calculation of the descent (or search) direction.

Another key aspect of the disclosed approach for solving the inverse problem with the SPN model is with respect to the simplification of the Hessian matrix in the case of the PDE-constrained algorithm. Additional computational efficiency is gained by implementing a reduced Hessian sequential quadratic programming (rSQP) scheme. The rSQP scheme allows for computationally efficient solutions to the optimization problem by reducing the size of the Hessian matrix needed to be stored and updated. Variables associated with the disclosed reconstruction process are summarized in Table 14 and discussed in more detail below.

Quasi-Newton Methods

Newton's method can be used to compute the roots of an equation. It has a rapid rate of convergence, typically quadratic. Thus, it can converge rapidly once an iterate is sufficiently close to the root of the function. However, application of Newton's method to large scale optimization problems can be prohibitively expensive from a computing stand point. Instead, other methods that exhibit convergence properties similar to Newton's method can be used. IN particular, a quasi-Newton, which is merely an approximation to Newton's method, can be used. The following presents a brief discussion of quasi-Newton methods that serve as a foundation to the optimization algorithms that can be used to solve Eqn. 9.3.

TABLE 14

Definition of Inverse Problem Variables

| | |
|---|---|
| $A \in \mathbb{C}^{m \times m}$ | $SP_N$ forward model operator matrix |
| $Q \in \mathbb{R}^{d \times m}$ | Partial current operator |
| $H \in \mathbb{R}^{n \times n}$ | Hessian matrix |
| $M \in \mathbb{C}^d$ | Experimental measurement vector (d = # of total measurement point |
| $P \in \mathbb{C}^d$ | Predicted measurement vector (d = # of total measurement points) |
| $u \in \mathbb{C}^m$ | $SP_N$ forward solution (i.e. fluence) |
| $b \in \mathbb{C}^m$ | $SP_N$ forward model source vector |
| $\lambda \in \mathbb{C}^m$ | Adjoint/Lagrangian variable |
| $\mu \in \mathbb{R}$ | DOT inverse variable (e.g. $\mu_a$ or $\mu'_s$) |
| $f(x) \in \mathbb{R}$ | Objective function |
| $\nabla f(x) \in \mathbb{R}^n$ | Gradient of objective function |
| $\nabla^2 f(x) \in \mathbb{R}^{n \times n}$ | Hessian of objective function |
| $x \in \mathbb{R}^n$ | General inverse variable |
| $\Delta x \in \mathbb{R}^n$ | Update direction of inverse variable |
| $\alpha \in \mathbb{R}$ | Update step size |
| $\Phi \in \mathbb{R}$ | Merit function |
| $D\Phi \in \mathbb{R}$ | Directional derivative of merit function |

Consider a general objective function that is a function of the general inverse variable x, $f(x)$. The goal of the optimization problem is to find the roots of this function, where the solution achieves an extremum, in particular, the value of x that minimizes $f(x)$. To understand the application of quasi-Newton methods to solving this type of optimization problem, Newton's method is derived for the following optimization problem:

$$\min_{x} g(x), \quad (9.4)$$

where $g: \mathbb{R}^n \to \mathbb{R}$ is a smooth function of x. With an assumption of differentiability, the optimal solution x that minimizes g(x) will satisfy the following condition:

$$\nabla_x g(x) = 0. \quad (9.5)$$

Newton's method can be applied to solve for roots of Eqn. 9.5, which corresponds to the value of x that minimizes Eqn. 9.4. Under Newton's method, for a function g(x) that satisfies $\nabla g(x)=0$, beginning with an initial guess $x^0$, a sequence $x^k$ for k>0 can be built such that it approaches the optimal solution x. The relationship can be stated as follows:

$$x^{k+1} = x^k + (\nabla g(x))^{-1} g(x). \quad (9.6)$$

As used herein, g(x) represents the gradient of the DOT objective function $f(\mu, u)$ in Eqns. 9.1 and 9.3, i.e., $g(x) = \nabla f(x)$. Thus, the iterative formula of Eqn. 9.6 can be written as follows:

$$x^{k+1} = x^k + (\nabla^2 f(x))^{-1} \nabla f(x). \quad (9.7)$$

Focusing on computing the term $(\nabla^2 f(x))^{-1} \nabla f(x)$, the first step is to expand $f$ by a second order Taylor series at $x+\Delta x$:

$$f(x + \Delta x) \approx f(x) + \nabla f(x)^T \Delta x + \frac{1}{2} \Delta x^T \nabla^2 f(x) \Delta x. \quad (9.8)$$

The function $f(x+\Delta x)$ attains a minimum when its gradient with respect to $\Delta x$ vanishes. Thus, differentiating both sides of the expression with respect to $\Delta x$ and equating the results to zero:

$$\frac{\partial}{\partial \Delta x} f(x + \Delta x) \approx \frac{\partial}{\partial \Delta x} \Big( f(x) + \nabla f(x)^T \Delta x + \frac{1}{2} \Delta x^T \nabla^2 f(x) \Delta x \Big), \quad (9.9)$$

yields a standard quadratic equation for the Newton direction or $\Delta x$, $$\nabla^2 f(x) \Delta x = -\nabla f(x). \quad (9.10)$$

In Eqn. 9.10, $\nabla f$ and $\nabla^2 f$ can be recognized as the gradient and second-order derivative or Hessian, respectively. Thus, given the gradient and Hessian of the objective function, this expression gives a formula for computing $\Delta x$:

$$\Delta x = -[\nabla^2 f(x)]^{-1} \nabla f(x). \quad (9.11)$$

Optimization algorithms that use the Newton direction can have a fast convergence rate, typically quadratic. However, the computational demands of directly calculating $\nabla^2 f(x)$ or its inverse can be challenging. As a result, it may be advantageous to employ an alternative to the Newton method for large scale optimization problems. For example, quasi-Newton algorithms, which approximate the product term, $[\nabla^2 f(x)]^{-1} \nabla f(x)$, can offer reduced computational demand and provide superlinear convergence properties. For example, L-BFGS and the symmetric-rank-one (SR1) algorithms, which are efficient quasi-Newton algorithms, can be used.

Given Eqn. 9.11 for computing the Newton direction $\Delta x$, the unknown variable x can be updated iteratively with quasi-Newton algorithms, such as the L-BFGS and SR1. More generally, the iterative formula is stated as follows:

$$x^{k+1} = x^k + \alpha^k \Delta x^k. \quad (9.12)$$

This process involves the computation of the Newton direction $\Delta x^k$ and the step length $\alpha^k$. The inclusion of $\alpha^k$ is to ensure that the change along the Newton direction results in a lower objective function value compared to the current iteration. The process of finding the Newton direction and the corresponding step length affect the convergence speed and the accuracy of the solution. The initial guess vector may be homogeneous or inhomogeneous, the choice reflecting a priori information on the distribution of optical properties inside the medium. For example, in a homogeneous initial guess the optical properties may be set to $\mu_a=0.3$ cm$^{-1}$ and $\mu'_s=10.0$ cm$^{-1}$. Given the initial guess $\mu^0$, the optimization algorithm seeks to find sequential approximations $\{\mu^k\}_0^\infty$ that continuously, or semi-continuously (i.e., with few exceptions), decrease the objective function (or a secondary measure termed the "merit" function).

Unconstrained Optimization

In the unconstrained formulation of the inverse problem in DOT, u is treated as dependent variables of an independent variable $\mu$. The objective function that minimizes the sum of squared errors is therefore written as:

$$\min_{\mu} f(\mu) = \frac{1}{2} [M - Qu(\mu)]^T \overline{[M - Qu(\mu)]}. \quad (9.13)$$

The forward model can be written as:

$$A(\mu) u(\mu) = b. \quad (9.14)$$

Alternatively, the objective function can be expressed as:

$$\min_{\mu} f(\mu) = \frac{1}{2} [M - Q(A^{-1}(\mu) b)]^T \overline{[M - Q(A^{-1}(\mu) b)]}. \quad (9.15)$$

Because the original constraint $A(\mu)u-b=0$ no longer appears in the minimization problem, the objective function is referred to as "unconstrained." Thus, any value can be selected for the inverse variable $\mu$ that minimizes the objective function. Additional constraints on the acceptable values of $\mu$ can be enforced, such as $\mu \geq 0$. Although specific constraints are not explicitly discussed below, embodiments of the disclosed subject matter can include specific constraints. The procedure detailed herein can be easily extended to circumstances where constraints on $\mu$ exist.

Gradient of Objective Function

The gradient of the objective function, i.e., $[\nabla_\mu f(\mu)]$ is used by the LBFGS algorithm to compute the Newton direction $\Delta \mu$, as is apparent from Eqn. 9.11. Directly differentiating Eqn. 9.13 with respect to $\mu$, $$\nabla_\mu f(\mu, u) = \frac{\partial f(\mu, u)}{\partial u} \frac{\partial u(\mu)}{\partial \mu} = \frac{\partial u}{\partial \mu} \frac{\partial f}{\partial u}, \quad (9.16)$$

yields the gradient. The second term on the right hand side of Eqn. 9.16, the derivative of the objective function with respect to the forward solution u, can be obtained by differentiating Eqn. 9.1 with respect to u, $$\frac{\partial f(\mu, u)}{\partial u} = Q^T \overline{(Qu - M)}. \quad (9.17)$$

The first term on the right hand side of Eqn. 9.16, the derivative of the forward variable with respect to the inverse variable μ, can be obtained by differentiating Eqn. 9.14 with respect to u and solving for the appropriate term, resulting in $$\frac{\partial u(\mu)}{\partial \mu} = -\frac{\partial Au}{\partial \mu}(A^T)^{-1} \quad (9.18)$$

Using the results from Eqns. 9.17-9.18 on Eqn. 9.16 yields the formula for computing the gradient of the objective function, $$\nabla_\mu f(\mu, u) = -\frac{\partial Au}{\partial \mu}(A^T)^{-1}[Q^T\overline{(Qu-M)}]. \quad (9.19)$$

Given the value of the inverse variable $\mu^k$ at inverse iteration k, the forward model ($A^k$), and its partial derivative with respect to μ are updated using $\mu^k$. The $\mu^k$ term is computed using the latest forward model, $A^k$. The terms Q and b do not vary across iterations. Thus, all terms in Eqn. 9.19 are well defined. The term, $$(A^T)^{-1}[Q^T\overline{(Qu-M)}] = \lambda \quad (9.20)$$

is part of a linear problem that can be rewritten as:

$$A^T\lambda = Q^T\overline{(Qu-M)}. \quad (9.21)$$

This is the adjoint equation to the forward model, where the adjoint variable λ has been introduced. This linear system can be solved for λ and the solution in Eqn. 9.19 used. Then, to obtain the gradient of the objective function [$\nabla_\mu f(\mu, u)$] it only remains to compute the term $$\frac{\partial Au}{\partial \mu}.$$

The adjoint equation technique can allow for highly efficient computing of the gradient of the objective, as the cost associated with computing the gradient is on the same order of magnitude as the cost of solving a forward problem. Using the adjoint variable, the gradient of the objective function can be rewritten into a version that can be used in the L-BFGS algorithm, $$\nabla_\mu f(\mu, u) = -\left(u^T \frac{\partial A}{\partial \mu}\lambda\right)_{Re}. \quad (9.22)$$

Merit Function

The merit function for the unconstrained problem is simply the objective function itself, i.e., Eqn. 9.15:

$$\phi_\eta^k(u^k, \mu^k) = \frac{1}{2}(Qu^k - M)^T\overline{(Qu^k - M)}. \quad (9.23)$$

The line search routine employs the computation of the directional derivative of $\phi_\eta^k(u^k, \mu^k)$ along the descent direction $\Delta p = \Delta u$, which is given by $$D\phi_\eta^k(\mu^k) = \left(u^{k^T}\frac{\partial A^k}{\partial \mu}\lambda^k\right)_{Re}^T \Delta\mu^k. \quad (9.24)$$

This term is the inner product of the gradient of the objective function and the descent direction.

Unconstrained Algorithm

The final form of the unconstrained algorithm is presented as Algorithm 2 in Table 15. A subroutine for computing the step size $\alpha^k$ is presented as Algorithm 3 in Table 16. The algorithm exits when the objective function reaches a tolerance ϵ, for example, when $\epsilon = 1.0 \times 10^{-5}$, or when a maximum allowed number of inverse iterations K is reached. The tolerance of the GMRES solver can vary throughout the algorithm and is denoted by τ.

The reconstruction algorithm can solve the forward and adjoint problems using the restarted GMRES algorithm with high degrees of tolerance within the outer loop, for example, up to $1.0 \times 10^{-12}$. Such steps can obtain accurate approximations to the gradient of the objective function, $\nabla_\mu^k f(\mu^k, u^k)$, which is an integral part of the L-BFGS algorithm that updates the Newton direction, $\Delta\mu^k$. This step can be repeated until a satisfactory $\alpha^k$ is found in order to allow sufficient decrease in the merit function over the previous inverse iteration. The repetition of forward and adjoint problem solving within each inverse iteration is one of the reasons for the extensive computation time associated with the unconstrained reconstruction technique. A PDE-constrained optimization approach, as described below, can address this issue and result in improved computation times.

TABLE 15

Algorithm 2 - Unconstrained optimization for DOT with the FD-FV-SPN model

INVERSE ← true
k ← 0
$\mu^k$ ← Set initial guess (e.g. $\mu_a$ and $\mu_s$)
$H^k$ ← I Set the initial value of the Hessian matrix to the identity matrix
$A^k$ ← A($\mu^k$)
$u^k$ ← $A^{k-1}$b (using GMRES, τ = 1.0 × 10$^{-12}$)
while INVERSE do $\lambda^k \leftarrow \left(A^{k^T}\right)^{-1} Q^T\overline{(Qu^k - M)}$(using GMRES, τ = 1.0 × 10$^{-12}$)

$\nabla_\mu^k f(\mu^k, u^k) \leftarrow -\left(u^{k^T}\frac{\partial A^k}{\partial \mu}\lambda^k\right)_{Re}$ $\Delta\mu^k$ ← − $(H_c^k)^{-1} \nabla_\mu^k f(\mu^k, u^k)$ (using L-BFGS)
Line search: Compute $\alpha^k$ (see Algorithm 3)
$\mu^{k+1}$ ← $\mu^k + \alpha^k\Delta\mu$
$A^{k+1}$ ← A($\mu^{k+1}$)
$u^{k+1}$ ← $(A^{k+1})^{-1}$ b (using GMRES, τ = 1.0 × 10$^{-12}$)
$l^{k+1}$ ← f($\mu^{k+1}$, $u^{k+1}$)
if ($l^{k+1}$ < ϵ or k >= K) then
    INVERSE ← false
else
    k ← k + 1
end if
end while

TABLE 16

Algorithm 3 - Line search subroutine for unconstrained optimization

Compute ϕ(0) using (9.23)
Compute Dϕ(0) using (9.24)
LINESEARCH ← true

TABLE 16-continued

Algorithm 3 - Line search subroutine for unconstrained optimization

```
i ← 0
α_i ← 1
while LINESEARCH do
    μ_{i+1} ← μ_i + α_i Δμ^k
    A_{i+1} ← A(μ_{i+1})
    u_{i+1} ← (A_{i+1})^{-1} b (using GMRES, τ = 1.0 × 10^{-12})
    Compute φ(α_i) using (9.23)
    if ( φ(α_i) ≥ φ(0) + cα_i Dφ(0) or i >= i_{max} ) then
        α^k ← α_i
        LINESEARCH ← false
    else
```
$$\alpha_{i+1} = \alpha_i \cdot \max\left(\min\left(0.9, \frac{D\phi(0)\alpha_i}{\phi(0) + \alpha_i D\phi(0) - \phi(\alpha_i)}\right), 0.1\right)$$
```
        i ← i + 1
    end if
end while
```

PDE-Constrained Optimization

The key difference between "unconstrained" and PDE-constrained optimization approaches is that the forward and inverse variables are treated as independent variables in the latter technique. This assumption allows simultaneous solutions to the DOT problem with respect to both the forward and inverse variables, $\mu$ and $u$, respectively. As noted above, the unconstrained problem computes the forward solution, $u$, after each inverse iteration (i.e., after every update to $\mu$). This process can be very time consuming because the forward problem is desired to be solved very accurately (i.e., to a GMRES tolerance of approximately $1.0 \times 10^{-12}$). In contrast, the PDE-constrained algorithm does not require that the forward problem be computed to such degree of accuracy. Instead, the value of $u$ is iteratively updated in parallel to the update of $\mu$. This results in significant reduction in computation time.

To realize additional significant acceleration of the PDE-constrained optimization process, simplifications can be made to the Hessian matrix of the quadratic problem that results from the DOT objective function. This is referred to as a reduced-Hessian or reduced sequential quadratic programming (rSQP) approach. The SQP approach itself is particularly effective at solving large-scale non-linear optimization, but the rSQP method improves on the SQP method by reducing the effective size of the Hessian matrix that needs to be computed (or approximated). Significant gains in computation time and resources can thus be realized. The above-noted techniques can be applied to solving the DOT problem with the FD-FV-SPN model, and is described in more detail.

Since $\mu$ and $u$ can be treated as independent variables, Eqn. 9.3 can be reformulated. In particular, using the Lagrange multiplier $\lambda$, the objective function can be written, subject to the forward problem, as $$\min_{\mu, u, \lambda} \mathcal{L}(\mu, u, \lambda) = |\frac{1}{2}(Qu - M)^T \overline{(Qu - M)} + \lambda^T (A(\mu)u - b). \quad (9.25)$$

This is a PDE-constrained problem which can be simultaneously solved for the forward and inverse solutions. For convenience, the problem can be written as:

$$\min_x \mathcal{L}(x) = f^I + \lambda^T f^F, \quad (9.26)$$

where $f^I$ denotes the inverse error and $f^F$ denotes the error contribution from the forward model. The Lagrangian variable, $\lambda$, is a measure of the ratio between the inverse and forward errors. The goal of the optimization problem is to find the optimal values of $\mu$, $u$ and $\lambda$ that minimize $L(x)$, where for notational purposes, the total unknown variable $x$ can be defined as:

$$x = \begin{bmatrix} \mu \\ u \\ \lambda \end{bmatrix}. \quad (9.27)$$

Then, applying techniques similar to those described above to Eqn. 9.26, yields a standard quadratic equation for $\Delta x$ as a function of the gradient ($\nabla L$) and second-order derivative or Hessian ($\nabla^2 L$), as shown in Eqn. 9.28:

TABLE 17

Definition of PDE-constrained optimization terms $$f^I = \frac{1}{2}(Qu - M)^T \overline{(Qu - M)}$$

$$f^F = Au - b$$
$$f_\mu^I = 0$$
$$f_{\mu\mu}^I = 0$$
$$f_u^I = Q^T \overline{(Qu - M)}$$
$$f_{uu}^I = Q^T Q$$
$$f_{u\mu}^I = 0$$
$$f_{\mu u}^I = 0$$

$$f_\mu^F = u^T \frac{\partial A}{\partial \mu}$$

$$f_{\mu\mu}^F = u^T \frac{\partial^2 A}{\partial \mu^2}$$

$$f_u^F = A^T$$
$$f_{uu}^F = 0$$

$$f_{\mu u}^F = \frac{\partial A|}{\partial \mu}$$

$$f_{u\mu}^F = \frac{\partial A}{\partial \mu}$$

$$f_\lambda^I = 0$$
$$f_{\lambda\lambda}^I = 0$$
$$f_{u\lambda}^I = 0$$
$$f_{\lambda\mu}^I = 0$$
$$f_{u\lambda}^I = 0$$
$$f_{\lambda u}^I = 0$$

$$W = \begin{bmatrix} f_{\mu\mu}^{FT} & f_{\mu u}^F{}^T \\ \lambda^T f_{u\mu}^F & \lambda^T f_{uu}^I \end{bmatrix}$$

$$F = [f_\mu^F \ f_u^F]$$

$$C = \begin{bmatrix} f_\mu^I \\ f_u^I \end{bmatrix}$$

$$\Delta_p = \begin{bmatrix} \Delta\mu \\ \Delta u \end{bmatrix}$$

$$\hat{Z}^k = -\left(f_u^{F^k}\right)^{-1} f^{F^k}$$

TABLE 17-continued

Definition of PDE-constrained optimization terms $$\hat{Y}^k = -\left(f_u^{Fk}\right)^{-1} f_\mu^{Fk}$$

$$\nabla^2 L(x)\Delta x = -\nabla L(x). \qquad (9.28)$$

Because this is an "all-in-one" updating scheme, finding $\Delta x$ implies the Newton directions of the inverse variable ($\Delta \mu$), the forward variable ($\Delta u$), and the Langrange multiplier ($\Delta \lambda$) are determined. Described below is a practical method for computing $\nabla L$ and $\nabla^2 L$ so that $\Delta x$ can be obtained.

Formulae for the gradient and Hessian can be derived by directly differentiating the objective function of Eqn. 9.26. Minimizing solutions can be obtained at points where the first order Karush-Kuhn-Tucker (KKT) conditions are met. That is, at points where the derivative of the functional L(x) with respect to x (i.e. its arguments $\mu$, u, and $\lambda$) vanishes or $$\nabla_x L(x) = 0. \qquad (9.29)$$

An expression for the gradient of the Lagrangian function can be obtained by differentiating the inverse $f^I$ and forward $f^F$ error functions with respect to the x:

$$\nabla \mathcal{L}(x) = \begin{bmatrix} \nabla_\mu \mathcal{L}(x) \\ \nabla_u \mathcal{L}(x) \\ \nabla_\lambda \mathcal{L}(x) \end{bmatrix} = \begin{bmatrix} f_\mu^I + f_\mu^{F^T}\lambda \\ f_u^I + f_u^{F^T}\lambda \\ f_\lambda^I + f^F \end{bmatrix} \qquad (9.30)$$

The expression $\nabla_\mu L(x)$ is the derivative of the forward operator with respect to the inverse variable $\mu$ (i.e., the sensitivity equation of the Lagrangian), while the term $\nabla_u L(x)$ can be recognized as the adjoint equation to the forward problem. The expression for $\nabla_\lambda L(x)$ is equivalent to the residual of the discretized SPN forward model.

An expression for the Hessian matrix can be obtained from the second order derivatives of the Lagrangian with respect to the forward, inverse, and Lagrange variables:

$$\nabla^2 \mathcal{L}(x) = \begin{bmatrix} f_{\mu\mu}^I + f_{\mu\mu}^{F^T}\lambda & f_{\mu u}^I + f_{\mu u}^{F^T}\lambda & f_{\mu\lambda}^I + f_\mu^{F^T} \\ f_{u\mu}^I + \lambda^T f_{u\mu}^F & f_{uu}^I + \lambda^T f_{uu}^F & f_{u\lambda}^I + f_u^{F^T} \\ f_{\lambda\mu}^I + f_\mu^{F^T} & f_{\lambda u}^I + f_u^{F^T} & f_{\lambda\lambda}^I \end{bmatrix} \qquad (9.31)$$

Because u, $\mu$, and $\lambda$ can be treated as independent variables, the first and second order derivatives of the forward and inverse error functions as summarized in Table 17 can be easily computed. Using the definitions in Table 17, Eqns. 9.30-9.31 can be simplified to the following equations:

$$\nabla \mathcal{L}(\mu) = \begin{bmatrix} f_\mu^{F^T}\lambda \\ f_u^I + f_u^{F^T}\lambda \\ f^F \end{bmatrix} \qquad (9.32)$$

$$\nabla^2 \mathcal{L}(\mu) = \begin{bmatrix} f_{\mu\mu}^{F^T}\lambda & f_{\mu u}^{F^T}\lambda & f_\mu^{F^T} \\ \lambda^T f_{u\mu}^F & \lambda^T f_{uu}^I & f_u^{F^T} \\ f_\mu^{F^T} & f_u^{F^T} & 0 \end{bmatrix} \qquad (9.33)$$

Eqn. 9.28 can then be rewritten with the expanded gradient and Hessian terms defined by Eqns. 9.32-9.33, where variables F and C can be introduced to denote the partial derivatives of the forward and inverse error functions, respectively (defined in Table 17):

$$\begin{bmatrix} W & F^T \\ F & 0 \end{bmatrix} \begin{bmatrix} \Delta p \\ \Delta \lambda \end{bmatrix} = -\begin{bmatrix} C + F^T\lambda \\ f \end{bmatrix} \qquad (9.34)$$

At this point, there are equations to compute the gradient of the objective function with respect to all unknown variables, so that the quadratic system can be solved using a quasi-Newton algorithm, such as L-BFGS. However, solving for the optimal solution at this point can be difficult because of the burden associated with computing and updating the Hessian matrix, which is now larger than the Hessian matrix in the unconstrained problem. To overcome this challenge, various techniques can be used that allow for the use of approximations to the Hessian matrix and that lead to significant reductions in its size and complexity, as described in more detail below.

Reduced Hessian Approach

The system of equations defined by Eqn. 9.34 can be written in quadratic form by considering the solution to the following equivalent system:

$$\underset{\Delta p, \lambda}{\text{minimize}} \mathbb{L}(\Delta p, \lambda) = \left(\frac{1}{2}\Delta p^T W \Delta p + \Delta p^T C\right) + (\lambda^{k+1})^T (F\Delta p + f), \qquad (9.35)$$

where the relationship $\lambda^{k+1} = \lambda^k + \Delta\lambda^k$ is used. The equivalence to the original system can be seen by differentiating $\mathbb{L}(\Delta p, \lambda)$ with respect to $\Delta p$ (Eqn. 9.36) and $\lambda$ (Eqn. 9.37), setting the expressions equal to zero, and then adding the resulting expressions. The resulting system of equations is equivalent to Eqn. 9.34:

$$\frac{\partial}{\partial \Delta p}\mathbb{L} = 0 = W\Delta p + C + F^T\lambda^{k+1} \qquad (9.36)$$

$$\frac{\partial}{\partial \lambda}\mathbb{L} = 0 = F\Delta p + f \qquad (9.37)$$

The inverse and forward variables can then be linearized. Note that the forward (u) and inverse variables ($\mu$) have been separated from the Lagrange variable ($\lambda$), and the $\Delta u$ and $\Delta \mu$ terms have been grouped together into a new variable $\Delta p$, such that:

$$\Delta p^k = Z^k + Y^k \Delta \mu^k. \qquad (9.38)$$

The values of Z and Y can be optimally defined as the following functions of $f^I$ and $f^F$:

$$Z^k = \begin{bmatrix} 0 \\ \hat{Z}^k \end{bmatrix}, \qquad (9.39)$$

$$Y^k = \begin{bmatrix} I \\ \hat{Y}^k \end{bmatrix}.$$

The terms $\hat{Z}^k$ and $\hat{Y}^k$ are defined by Eqns. 9.40-9.41:

$$\hat{Z}^k = -(f_u^k)^{-1} f^k \qquad (9.40)$$

$$\hat{Y}^k = -(f_u^k)^{-1} f_\mu^k \qquad (9.41)$$

Substituting Eqns. 9.38 and 9.39 into Eqn. 9.36 and multiplying both sides by $Y^{kT}$, results in:

$$Y^{kT}W^k Y^k \Delta\mu^k + Y^{kT}W^k Z^k + Y^{kT}F^{kT}\lambda^{k+1} = -Y^{kT}C^k. \quad (9.42)$$

Eqn. 9.42 can be simplified to:

$$H_r^k \Delta\mu^k + d_r^k = -g_r^k. \quad (9.43)$$

The term $H_r^k = Y^{kT}W^k Y^k$ is the "reduced Hessian," $d_r^k = Y^{kT}W^k Z^k$ is the "cross-term," $Y^{kT}F^{kT} = 0$, and the "reduced gradient" is given by:

$$g_r^k = Y^{kT}C^k. \quad (9.44)$$

The updated direction, $\Delta\mu^k$, to the inverse variable, $\mu^k$, can be obtained from Eqn. 9.43, after ignoring the cross term $d_r^k$, as follows:

$$\Delta\mu^k = -(H_r^k)^{-1}(g_r^k). \quad (9.45)$$

The L-BFGS algorithm can be used to compute and directly update the inverse of the reduced Hessian matrix $(H_r^k)^{-1}$ at each inverse iteration k. Solving for $\Delta u$ using the second equation in Eqn. 9.34, where $F^k \Delta p^l = -f^k$ can be rewritten as $f_\mu^k \Delta\mu^k + f_u^k \Delta u^k = -f^k$, and then solved and simplified as follows:

$$\Delta u^k = -(f_u^k)^{-1} f^k - (f_u^k)^{-1} f_\mu^k \Delta\mu, \quad (9.46)$$

$$= \hat{Z}^k - \hat{Y}^k \Delta\mu^k.$$

Eqns. 9.40 and 9.41 were used to simplify Eqn. 9.46. The original quadratic problem, where the Hessian (W) is reduced to $H_f^k$ at the $k^{Th}$ inverse iterations, can be rewritten as follows:

$$\begin{bmatrix} H_r^k & 0 & f_\mu^T \\ 0 & Q^T Q & f_u^T \\ f_\mu & f_u & 0 \end{bmatrix} \begin{bmatrix} \Delta\mu \\ \Delta u \\ \Delta\lambda \end{bmatrix} = \begin{bmatrix} c_\mu + f_\mu^T \lambda \\ c_u + f_u^T \lambda \\ f \end{bmatrix}. \quad (9.47)$$

The updated value of the variable $\lambda^{k+1}$ can be computed using the adjoint equation method. Differentiating the Lagrangian function in Eqn. 9.25 with respect to the forward variable u and setting the derivative to zero results in:

$$0 = -Q^T \overline{(Qu-M)} + A^T \lambda. \quad (9.48)$$

Then, $\lambda^{k+1}$ can be obtained by solving Eqn. 9.49 with a linear solver, such as GMRES.

$$\lambda^{k+1} = -(A(\mu^{k+1})^T)^{-1}[Q^T \overline{(Qu^{k+1}-M)}] \quad (9.49)$$

The update to the Lagrangian variable $\lambda^{k+1}$ can be computed by solving the adjoint problem.

Summary of Formulations

A well-prescribed set of equations can be used for computing the update to each of the three optimization variables. In particular, the forward and inverse variables can be updated along $\Delta u$ and $\Delta\mu$, such that:

$$u^{k+1} = u^k + \alpha^k \Delta u^k \quad (9.50)$$

$$\mu^{k+1} = \mu^k + \alpha^k \Delta\mu^k \quad (9.51)$$

where $\Delta u$ and $\Delta\mu$ are given by Eqns. 9.45 and 9.46, respectively. The update to the Lagrange variable $\lambda$ can be obtained by solving the adjoint problem to the forward model as specified by Eqn. 9.49, which becomes:

$$\lambda^k = -(A(\mu^k)^T)^{-1}[Q^T \overline{(Qu^k-M)}]. \quad (9.52)$$

The adjoint equation, i.e., Eqn. 9.52, can be solved using the restarted GMRES solver, with the right hand side vector inside brackets, [•]. Then, given $\lambda^k$ and by expanding the expression for the reduced gradient from Eqn. 9.44 into Eqn. 9.45, a clear expression for $\Delta\mu$ that is a function of the forward model, forward solution, and the Lagrangian variable can be obtained. The reduced gradient simplifies to:

$$g_r^k = -\left( u^{kT} \frac{\partial A^k}{\partial \mu} \lambda^k \right)_{Re}. \quad (9.53)$$

Given the gradient of the objective function with respect to the inverse variable $\mu$, the update direction $\Delta\mu$ can be given by:

$$\Delta\mu^k = -(H_r^k)^{-1} \left( u^{kT} \frac{\partial A^k}{\partial \mu} \lambda^k \right)_{Re}. \quad (9.54)$$

This vector, the Newton direction, can be computed using the L-BFGS algorithm. The update to the forward variable $\Delta u$ can be simplified by expanding Eqn. 9.46, which results in:

$$\Delta u^k = -(A^k)^{-1} \left[ (A^k u^k - b) + u^{kT} \frac{\partial A^k}{\partial \mu} \Delta\mu^k \right]. \quad (9.55)$$

To obtain the Newton direction (update direction) of the forward variable, $\Delta u^k$, the system of linear equations in Eqn. 9.55 can be solved using the restarted GMRES algorithm, where the right hand side vector is the bracketed term, [•]. The Lagrange variable $\lambda$ (Eqn. 9.52), inverse variable $\mu$ (Eqn. 9.54), and forward variable u (Eqn. 9.55) are all functions of the SPN forward model matrix A and source vector b. The optimization problem and its associated variables are, therefore, all defined.

Merit Function

The merit function is designed to ensure that the error contribution from the inverse and forward variables both decrease. As used herein, the objective function is given by:

$$\phi_\eta^k(u^k, \mu^k) = \frac{1}{2}(Qu^k - M)^T \overline{(Qu^k - M)} + \eta_k \|A^k u^k - b^k\|_1. \quad (9.56)$$

The line search routine uses the computation of the directional derivative of $\phi_\eta^k(u^k, \mu^k)$ along the descent direction $\Delta p = (\Delta u, \Delta\mu)$, which is given by:

$$D\phi_\eta^k(u^k, \mu^k) = \left( u^{kT} \frac{\partial A^k}{\partial \mu} \lambda^k \right)_{Re}^T \Delta\mu^k - \eta_k \|A^k u^k - b\|_1. \quad (9.57)$$

rSQP PDE-constrained Algorithm

A general algorithm for iteratively solving for the optimal values of $\mu$ and u that simultaneously minimizes the error contribution from the inverse and forward models is presented as Algorithm 4 in Table 18. The algorithm can exit when the objective function reaches a particular tolerance $\epsilon$ (for example, $\epsilon=1\times10^{-5}$) or reaches a maximum allowed number of inverse iterations K. The tolerance of the GMRES solver varies throughout the algorithm and is denoted by .

In contrast to the unconstrained reconstruction algorithm, the PDE-constrained algorithm does not require the solution of the forward and the adjoint problems with accurate tolerances. Instead, the forward problem is solved accurately only once, e.g., at the beginning of the inverse algorithm (for example, $\tau=1.0\times10^{-8}$). The adjoint problem can be solved with relaxed tolerances compared to the unconstrained problem. For example, the tolerance can be chosen within a range of $\tau=1.0\times10^{-4}$ and $\tau=1.0\times10^{-6}$, although other values are also possible according to one or more contemplated embodiments. In general, while there is freedom in choosing the value of the tolerance, solving the adjoint problem with tighter tolerance may only lead to marginal increases in accuracy despite a substantial increase in computation time.

The Newton direction for the forward variable, $\Delta u^k$, can be obtained by solving a linear problem with the GRMES algorithm. A relaxed tolerance can be used, for example, within a range of $\tau=1.0\times10^{-2}$ and $\tau=1.0\times10^{-4}$, although other values are also possible according to one or more contemplated embodiments.

TABLE 18

Algorithm 4 - rSQP PDE-constrained optimization for DOT with the FD-FV-SPN model

```
INVERSE ← true
k ← 0
μk ← Set initial guess (e.g. μa and μs)
Ak ← A(μk)
uk ← Compute from AkTuk = b using GMRES (τ = 1.0 × 10−8)
Hk ← I Set the initial value of the Hessian matrix to the identity matrix
while INVERSE do
    λk ← Compute from Akλk = QT (Quk − M) using GMRES (τ = 1.0 × 10−4)
```
$$g_r^k \leftarrow -\left(u^{kT}\frac{\partial}{\partial\mu}A^k\right)^T \lambda^k$$

$$\Delta\mu^k \leftarrow -(H_t^k)^{-1}\left(u^{kT}\frac{\partial}{\partial\mu}A^k\right)^T \lambda^k \text{ using L-BFGS algorithm}$$

$$\Delta u^k \leftarrow -(A^k)^{-1}\left[(Au-b)^k + \left(u^T\frac{\partial}{\partial\mu}A\right)^k \Delta\mu^k\right] \text{ using GMRES solver}(\tau = 1.0\times10^{-2})$$

```
    Line search: Compute αk (see Algorithm 5)
    μk+1 ← μk + αkΔμ
    uk+1 ← uk + αkΔu
    lk+1 ← f(μk+1, uk+1, λk+1)
    if (lk+1 < ε or k >= K) then
        INVERSE ← false
    else
        k ← k + 1
    end if
end while
```

TABLE 19

Algorithm 5 - Line search subroutine for rSQP PDE-constrained algorithm.

```
Compute φ(0) using (9.56)
Clompute Dφ(0) using (9.57)
LINESEARCH ← true
i ← 0
αi ← 1
while LINESEARCH do
    μi+1 ← μi + αiΔμk
    ui+1 ← ui + αiΔuk
    Ai+1 ← A(μi+1)
    Compute φ(αi) using (9.56)
    if ( φ(αi) ≥ φ(0) + cαiφ'(0) or i >= imax) then
        αk ← αi
```

TABLE 19-continued

Algorithm 5 - Line search subroutine for rSQP PDE-constrained algorithm.

```
        LINESEARCH ← false
    else
```
$$\alpha_{i+1} = \alpha_i \cdot \max\left(\min\left(0.9, \frac{D\phi(0)\alpha_i}{\phi(0)+\alpha_i D\phi(0)-\phi(\alpha_i)}\right), 0.1\right)$$
```
        i ← i + 1
    end if
end while
```

An algorithm for the line search process is shown as Algorithm 5 in Table 19. The line search process can be repeated until a satisfactory $\alpha^k$ is found, which can increase the likelihood that a sufficient decrease in the merit function over the previous inverse iteration is obtained. However, the line search routine of the PDE-constrained algorithm does not require solving a linear problem, unlike the line search routine in the unconstrained algorithm. Thus, the PDE-constrained reconstruction algorithm can achieve convergence at reduced computation times as compared to the unconstrained algorithm.

Gradient of Forward Model

The gradient of the forward model matrix A with respect to the inverse variables (i.e., optical properties) appears in the constrained and unconstrained optimization approaches. But in DOT, the two primary optical properties of interest are $\mu_a$ and $\mu_s$. Detailed below is the derivation of formulae for computing the gradient with respect to $\mu_a$ and $\mu_s$. To avoid the direct computation of the partial derivative of A with respect to $\mu_s$ $$\left(\text{i.e., }\frac{\partial A}{\partial \mu_s}\right),$$

the reduced scattering coefficient $\mu'_s=(1-g)\mu_s$ can be used. To further simplify the computation of $\frac{\partial A}{\partial \mu_s}$ the following additional approximation can be made:

$$\mathcal{D} = \frac{1}{3(\mu_a + \mu'_s)} \approx \frac{1}{3\mu'_s} \quad (9.58)$$

Instead of solving for $\mu_s$ or $\mu'_s$, $\mathcal{D}$ (i.e., the diffusion coefficient) can be solved for, from which the scattering coefficient can be recovered. This approximation can work for applications in which the diffusion model is valid, for example, where $\mu_a \ll \mu'_s$.

Rather than making the above noted approximations, A can be differentiated with respect to $\mu_a$ and $\mu_s$ directly. The formulae for computing these terms depends on the order of the SPN model. Algorithms 6 and 7, shown in Tables 20 and 21, present the definitions of the partial derivatives of A with respect to $\mu_s$ and $\mu_a$ for the SP$_3$ model, respectively.

Numerical Phantoms

The performance of the algorithms was evaluated through simulations on a two-dimensional circular phantom and a three-dimensional phantom that resembles a human finger. Absorbing and scattering inclusions were placed inside each phantom and simulated measurement data (M) was generated using the SP$_3$ model on a dense FVM mesh and corrupted with 1.0% Gaussian white noise. For example, the 2-D mesh with which the simulated measurements were computed contains 37,247 nodes (73,236 tetrahedral elements), while the mesh on which the reconstructions are performed has 1,309 nodes (2,360 tetrahedral elements).

TABLE 20

Algorithm 6 - Gradient of SP$_3$ model matrix A with respect to $\mu_s$.

$\nabla_{\mu_s} A \leftarrow 0$
for (i = 0; i < M; i++) do
  $\nabla_{\mu_s} A_{ii} \mathrel{+}= \Delta V_i$
  for (j != 0; j < $S_T$; j++) do
    if ($S_j$ is interior surface) then
      k ← neighbor node number $\beta_1 \leftarrow \beta_1 - \frac{3(1-g)}{2l_s}\left[\frac{dA_j}{dr_j}\right][\mathcal{D}_1]_i^2$ $\beta_2 \leftarrow \beta_2 - \frac{7(1-g^3)}{2l_s}\left[\frac{dA_j}{dr_j}\right][\mathcal{D}_2]_i^2$ $\nabla_{\mu_s} A_{iik} \leftarrow -\frac{3(1-g)}{2l_s}\left[\frac{dA_j}{dr_j}\right][\mathcal{D}_1]_k^2$ $\nabla_{\mu_s} A_{iki} \leftarrow \frac{3(1-g)}{2l_s}\left[\frac{dA_j}{dr_j}\right][\mathcal{D}_1]_i^2$ $\nabla_{\mu_s} A_{ikk} \leftarrow \frac{3(1-g)}{2l_s}\left[\frac{dA_j}{dr_j}\right][\mathcal{D}_1]_k^2$ $\nabla_{\mu_s} A_{i+M,i+M,k} \leftarrow -\frac{7(1-g^3)}{2l_s}\left[\frac{dA_j}{dr_j}\right][\mathcal{D}_2]_k^2$ $\nabla_{\mu_s} A_{i+M,k+M,i} \leftarrow -\frac{7(1-g^3)}{2l_s}\left[\frac{dA_j}{dr_j}\right][\mathcal{D}_2]_i^2$ $\nabla_{\mu_s} A_{i+M,k+M,k} \leftarrow -\frac{7(1-g^3)}{2l_s}\left[\frac{dA_j}{dr_j}\right][\mathcal{D}_2]_k^2$ end if
  end for
  $\nabla_{\mu_s} A_{iii} \leftarrow \beta_1$ TABLE 20-continued Algorithm 6 - Gradient of SP$_3$ model matrix A with respect to $\mu_s$.

$\nabla_{\mu_s} A_{i+M,i+M,i} \leftarrow \frac{5(1-g^2)}{9l_s}[\Delta V]_i + \beta_2$ end for

TABLE 21

Algorithm 7 - Gradient of SP$_3$ model matrix A with respect to $\mu_a$.

$\nabla_{\mu_a} A \leftarrow 0$
for (i = 0; i < M; i++) do
  $\nabla_{\mu_a} A_{ii} \mathrel{+}= \Delta V_i$
  for (j = 0; j < $S_T$; j++) do
    if ($S_j$ is interior surface) then
      k ← neighbor node number $\beta_1 \leftarrow \beta_1 - \frac{3}{2l_a}\left[\frac{dA_j}{dr_j}\right][\mathcal{D}_1]_i^2$ $\beta_2 \leftarrow \beta_2 - \frac{7}{2l_a}\left[\frac{dA_j}{dr_j}\right][\mathcal{D}_2]_i^2$ $\nabla_{\mu_a} A_{iik} \leftarrow -\frac{3}{2l_a}\left[\frac{dA_j}{dr_j}\right][\mathcal{D}_1]_k^2$ $\nabla_{\mu_a} A_{iki} \leftarrow \frac{3}{2l_a}\left[\frac{dA_j}{dr_j}\right][\mathcal{D}_1]_i^2$ $\nabla_{\mu_a} A_{ikk} \leftarrow \frac{3}{2l_a}\left[\frac{dA_j}{dr_j}\right][\mathcal{D}_1]_k^2$ $\nabla_{\mu_a} A_{i+M,i+M,k} \leftarrow -\frac{7}{2l_a}\left[\frac{dA_j}{dr_j}\right][\mathcal{D}_2]_k^2$ $\nabla_{\mu_a} A_{i+M,k+M,i} \leftarrow -\frac{7}{2l_a}\left[\frac{dA_j}{dr_j}\right][\mathcal{D}_2]_i^2$ $\nabla_{\mu_a} A_{i+M,k+M,k} \leftarrow -\frac{7}{2l_a}\left[\frac{dA_j}{dr_j}\right][\mathcal{D}_2]_k^2$ end if
  end for $\nabla_{\mu_a} A_{iii} \leftarrow \frac{[\Delta V]_i}{l_a} + \beta_1$ $\nabla_{\mu_a} A_{i,i+M,i} \leftarrow -\frac{2}{3}\frac{[\Delta V]_i}{l_a}$ $\nabla_{\mu_a} A_{i+M,i,i} \leftarrow -\frac{2}{3}\frac{[\Delta V]_i}{l_a}$ $\nabla_{\mu_a} A_{i+M,i+M,i} \leftarrow \frac{[\Delta V]_i}{l_a} + \beta_2$ end for These two precautions help mitigate the risk of committing an inverse crime during the reconstruction process. Reconstruction of the location and optical properties of the phantom was attempted, beginning with a standard homogeneous initial guess for $\mu_a$ and $\mu'_s$. All simulations on these phantoms were performed with g=0.95, $\omega$=600 MHz, and $n_m$=1.4. These values are chosen to approximate the optical properties encountered in real-world applications. Other values may also be chosen depending on the application.

Figure 26A:
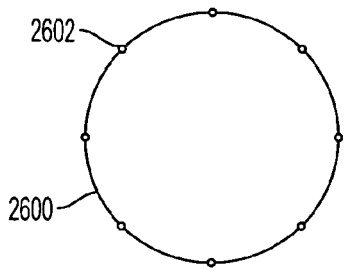
FIG. 26A shows the location of boundary sources for a disk-shaped phantom, according to one or more embodiments of the disclosed subject matter.
Figure 26B:
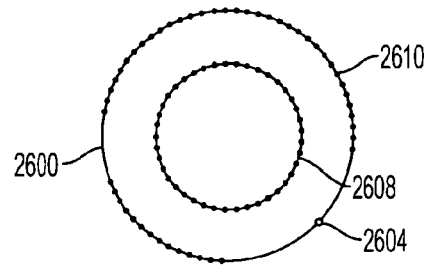
FIG. 26B shows the location of boundary detectors for a single boundary source as well as the placement of an internal cross-section of interest for a disk-shaped phantom, according to one or more embodiments of the disclosed subject matter.
Figure 27:
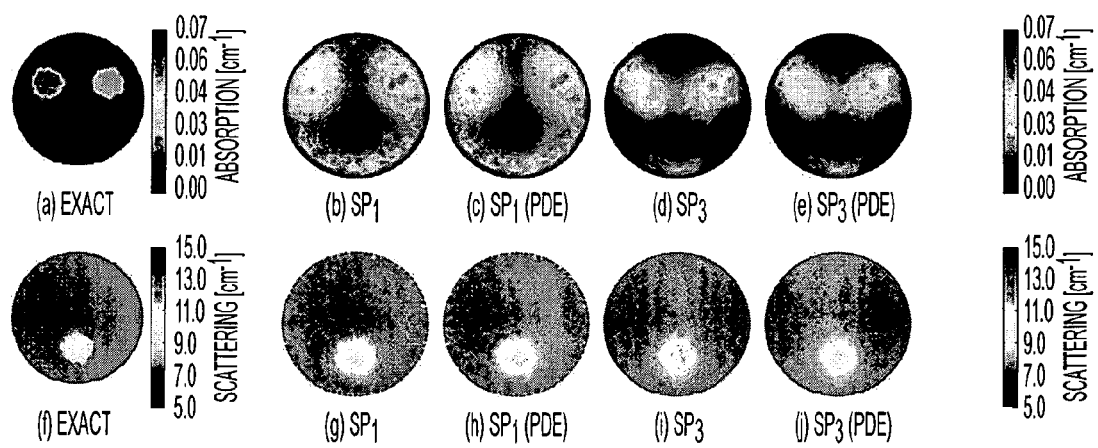
FIGS. 27A-27J show the distribution of exact values and reconstruction images of absorption and scattering coefficients computed using different models for a first disk phantom, according to one or more embodiments of the disclosed subject matter.

The two-dimensional phantom is defined to have eight (8) distinct boundary sources 2602 distributed along the perimeter of a circle 2600 with a diameter of 2 cm, as shown in FIG. 26A. For each source 2604, a total of one-hundred and ten (110) detectors 2610 were defined along the perimeter of the phantom 2600, as shown in FIG. 26B. The detectors 2610 can be at least 0.5 cm away from the respective source 2604. In certain circumstances, it may be convenient to analyze the optical properties along a specific cross-section inside the medium. For example, a circular cross-section 2608 (e.g., 0.5 cm from the center of the phantom) can be defined in the phantom 2600.

Performance Evaluation

The accuracy of each reconstruction can be quantified using the correlation coefficient, which is defined as:

$$r = \frac{\sum_{i=1}^{n}(\phi_i^r - \overline{\phi_i^r})(\phi_i^a - \overline{\phi_i^a})}{\sqrt{\sum_{i=1}^{n}(\phi_i^r - \overline{\phi_i^r})^2}\sqrt{\sum_{i=1}^{n}(\phi_i^a - \overline{\phi_i^a})^2}}, \quad (9.59)$$

where $\phi^a$ is the analytical (i.e., benchmark) solution and $\phi^r$ is the reconstruction image. The mean of each image is denoted by (•) and n refers to the total number of distinct mesh nodes. The analytical solution is known because it is used by the forward model to generate the "measurement" data M. The correlation coefficient r can be between −1 and 1, with r=1.0 corresponding to an exact match between the analytical and reconstruction images.

The computation efficiency can be captured by plotting the value of the inverse error over time for each combination of SPN model and reconstruction algorithm. The algorithm can be set to exit when the inverse error decreases by four orders of magnitude from its original value (i.e., a relative decrease of 1×10$^{-4}$). The accuracy of the reconstruction may be substantially improved by allowing the reconstruction process to continue for a longer amount of time. In this analysis, however, the exit criteria has been set such that the inverse error decreases by four orders of magnitude from its original value (i.e., the final inverse error is 0.01% of the original error).

Disk Phantom: Case 1

With respect to the first phantom, the optical properties thereof are within the diffuse regime, where the diffusion model performs well as a light propagation model. The optical properties of the background medium are $\mu_a$=0.01 cm$^{-1}$ and $\mu'_s$=12.50 cm$^{-1}$. The absorbing inclusions have $\mu_a$=0.05 cm$^{-1}$, while the low scattering inclusion is defined by $\mu'_s$=10.0 cm$^{-1}$. Reconstruction images of $\mu_a$ and $\mu'_s$ are presented in FIGS. 27A-27J. In particular, FIGS. 27A-27E show $\mu_a$ distribution in the two-dimensional phantom based on an exact distribution, SP$_1$ unconstrained reconstruction, SP$_1$ PDE-constrained reconstruction, SP$_3$ unconstrained reconstruction, and SP$_3$ PDE-constrained reconstruction, respectively. FIGS. 27F-27J show $\mu'_s$ distribution in the two-dimensional phantom based on an exact distribution, SP$_1$ unconstrained reconstruction, SP$_1$ PDE-constrained reconstruction, SP$_3$ unconstrained reconstruction, and SP$_3$ PDE-constrained reconstruction, respectively.

As is apparent from FIGS. 27A-27J, reconstructions obtained with the SP$_3$ model are more accurate than the reconstruction obtained with the SP$_1$ model. All SPN models correctly identify the general location of each inclusion. However, reconstructions with the SP$_1$ model have significant boundary artifacts in both $\mu_a$ and $\mu'_s$, and exhibit strong cross talk in $\mu_a$ images.

Figure 28:
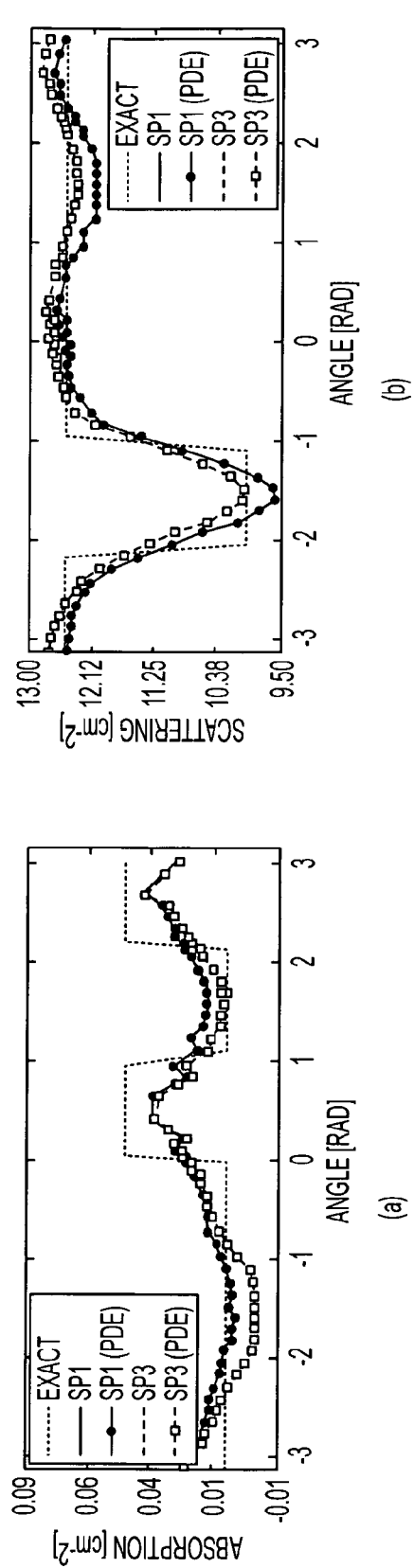
FIGS. 28A-28B are graphs of the values of absorption and scattering coefficients, respectively, along the internal cross-section of the first disk phantom computed using different models, according to one or more embodiments of the disclosed subject matter.

Analysis of the reconstruction values along the internal cross section allows for better understanding of the performance of the SPN models. In particular, FIGS. 28A-28B are plots of absorption and scattering coefficients, respectively, along the internal cross-section 2608 defined in FIG. 26B. As is apparent from FIGS. 28A-28B, both models underestimate $\mu_a$ in the region of the absorbing inclusions and marginally underestimate $\mu_a$ in the region of the $\mu_s$ inclusion.

In the case of $\mu'_s$ reconstructions, the SP$_1$ model underestimates $\mu'_s$ in the location of the scattering inclusion, while the SP$_3$ model accurately predicts the lower bounds of $\mu_s$. The cross-talk between absorption and scattering in the $\mu'_s$ reconstruction is evident in the SP$_1$ reconstruction, where the SP$_1$ model underestimates $\mu'_s$ at the location of the absorbing inclusions. Thus, the SP$_3$ model may be more resistant to cross-talk between $\mu_a$ and $\mu_s$.

The correlation coefficients between the reconstruction and the analytical solutions, as shown in Table 22, verify that the SP$_3$ model generates reconstructions that may be more accurate than reconstructions with the SP$_1$ model in both optical parameters, as is evident from the reconstruction images. With the SP$_3$ model, the $\mu'_s$ reconstruction is more accurate than the $\mu_a$ reconstruction, with correlation coefficients of r=0.85 and r=0.66, respectively. Similar patterns are observed for the SP$_1$ model, although the overall accuracy of the reconstructions are significantly lower than those obtained with the SP$_3$ model. The choice of optimization strategy, whether constrained or unconstrained, does not impact the overall accuracy of the reconstruction solution.

TABLE 22

Correlation coefficient between reconstruction and analytical solutions for the first phantom

|  | SP$_1$ | SP$_1$ (PDE) | SP$_3$ | SP$_3$ (PDE) |
| --- | --- | --- | --- | --- |
| c ($\mu_a$) [%] | 0.51 | 0.51 | 0.66 | 0.66 |
| c ($\mu'_s$) [%] | 0.51 | 0.51 | 0.85 | 0.85 |

Figure 29:
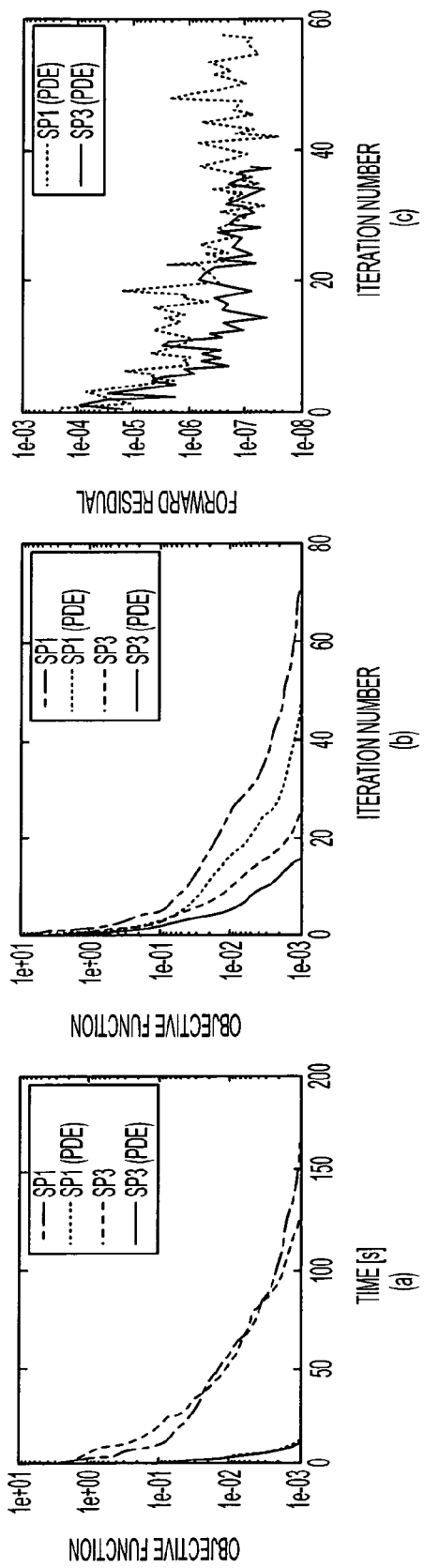
FIGS. 29A-29C are graphs reflecting the performance profile of the different reconstruction models applied to the first disk phantom, according to one or more embodiments of the disclosed subject matter.
Figure 30:
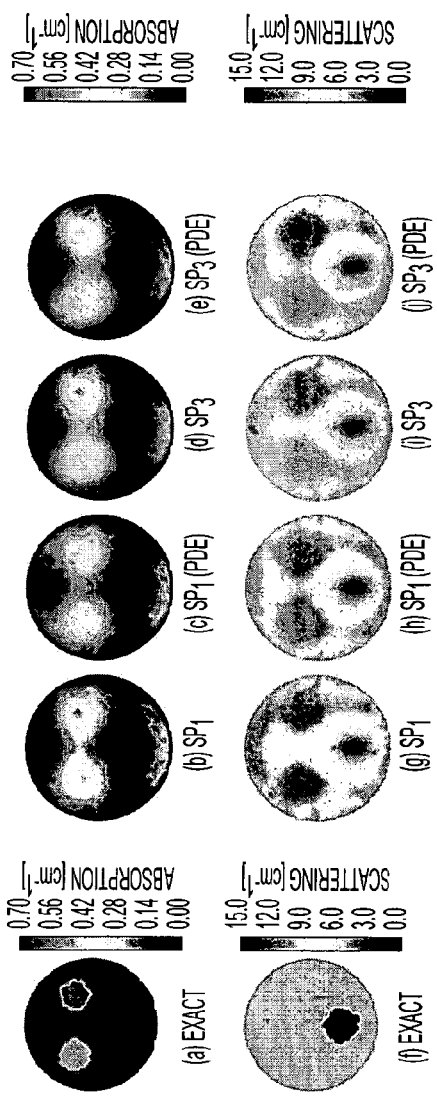
FIGS. 30A-30J show the distribution of exact values and reconstruction images of absorption and scattering coefficients computed using different models for a second disk phantom, according to one or more embodiments of the disclosed subject matter.

The computational advantages of using the PDE-constrained algorithm over the unconstrained algorithm is clear from FIGS. 29A-C, which show the performance profile of the reconstruction algorithms. In particular, the value of the objective function over time is plotted for each of the four reconstruction methods in FIG. 29A and at the conclusion of each inverse iteration in FIG. 29B. FIG. 29C shows the evolution of the forward model residual associated with the PDE-constrained algorithm across each inverse iteration.

In the case of the SP$_1$ model, the PDE-constrained algorithm converges approximately 12.2 times faster than the unconstrained algorithm. In the case of the SP$_3$ model, a speedup factor of 11.75 was achieved with the PDE-constrained algorithm compared to the unconstrained algorithm. The decrease in the inverse error after each inverse iteration is not significantly affected by the type of optimization algorithm, but is affected by the choice of SPN model, as illustrated in FIG. 29B. The SP$_3$ model exhibits a faster decay rate in the inverse error compared to the SP$_1$ model. FIG. 29C provides an example of how the "forward" error decreases over inverse iterations. The forward error decreases in parallel to the inverse error, which is a fundamental aspect of the use of the PDE-constrained algorithm.

Disk Phantom: Case 2

The optical properties of the second phantom are in the regime where the diffusion model is increasingly a poor approximation, with highly absorbing regions (i.e., $\mu_a$=0.5 cm$^{-1}$) and an area with low scattering values (i.e., $\mu'_s$=2.5 cm$^{-1}$). The background properties are $\mu_a$=0.1 cm$^{-1}$ and $\mu'_s$=10.0 cm$^{-1}$, which values closely resemble absorption and scattering of NIR light in various biological media, including the human breast ($\mu_a \in [0.34, 0.8]$ cm$^{-1}$, $\mu'_s \in [181.0, 492.0]$ cm$^{-1}$, g$\in[0.95, 0.98]$) and human brain gray matter ($\mu_a \in [0.16, 0.49]$ cm$^{-1}$ and $\mu'_s \in [5.9, 9.3]$ cm$^{-1}$). Reconstructions of $\mu_a$ and $\mu'_s$ are presented in FIGS. 30A-30J. In particular, FIGS. 30A-30E show $\mu_a$ distribution in the second phantom based on an exact distribution, $SP_1$ unconstrained reconstruction, $SP_1$ PDE-constrained reconstruction, $SP_3$ unconstrained reconstruction, and $SP_3$ PDE-constrained reconstruction, respectively. FIGS. 30E-30J show $\mu'_s$ distribution in the second phantom based on an exact distribution, $SP_1$ unconstrained reconstruction, $SP_1$ PDE-constrained reconstruction, $SP_3$ unconstrained reconstruction, and $SP_3$ PDE-constrained reconstruction, respectively.

As is apparent from FIGS. 30A-30J, the reconstructions obtained with the $SP_3$ model are more accurate than those obtained with the $SP_1$ model. The $\mu_a$ objects are more accurately resolved (based on separation) by the $SP_3$ model compared to the $SP_1$ model. In the case of $\mu'_s$, the reconstructions with the $SP_1$ model have more significant boundary artifacts compared to the reconstructions with the $SP_3$ model. The $SP_3$ model yields more accurate reconstructions than the $SP_1$ model, while reconstructions obtained with the PDE-constrained algorithm are as accurate as those obtained with the unconstrained algorithm.

Table 23 presents the correlation coefficients between the reconstruction and the analytical solutions for the second phantom. With the PDE-constrained algorithm, the correlation coefficient of the $SP_3$ model for $\mu_a$ is 0.68, while it is only 0.63 for the $SP_1$ model. In the case of $\mu'_s$, the correlation coefficients are 0.82 and 0.79, for the $SP_3$ and $SP_1$ models, respectively. As in the case of the first phantom, the scattering coefficient reconstruction is more accurate than the absorption reconstruction.

TABLE 23

Correlation coefficient between reconstruction and analytical solutions for the second phantom

|  | $SP_1$ | $SP_1$ (PDE) | $SP_3$ | $SP_3$ (PDE) |
|---|---|---|---|---|
| c ($\mu_a$) [%] | 0.64 | 0.64 | 0.68 | 0.68 |
| c ($\mu'_s$) [%] | 0.79 | 0.80 | 0.82 | 0.82 |

Figure 31:
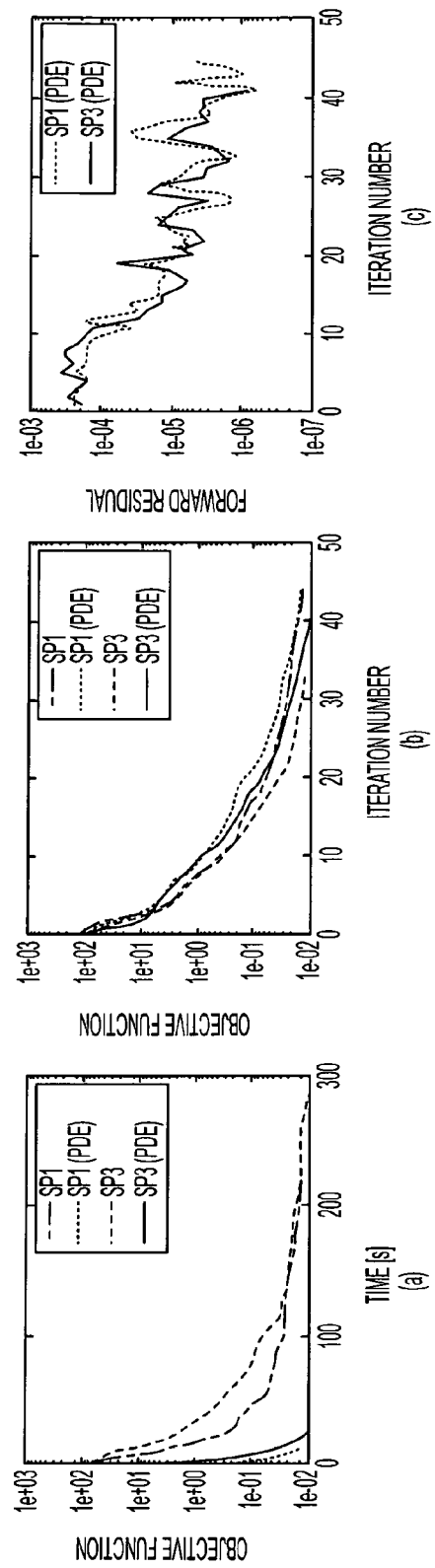
FIGS. 31A-31C are graphs reflecting the performance profile of the different reconstruction models applied to the second disk phantom, according to one or more embodiments of the disclosed subject matter.
Figure 32:
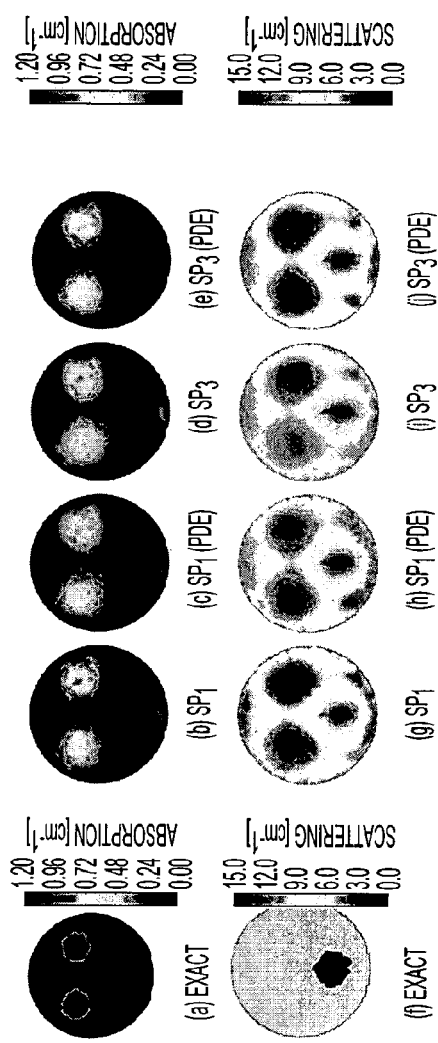
FIGS. 32A-32J show the distribution of exact values and reconstruction images of absorption and scattering coefficients computed using different models for a third disk phantom, according to one or more embodiments of the disclosed subject matter.

FIGS. 31A-31C illustrate the performance profile of the reconstruction algorithms on the second phantom. In particular, the value of the objective function over time is plotted for each of the four reconstruction methods in FIG. 31A and at the conclusion of each inverse iteration in FIG. 31B. FIG. 31C shows the evolution of the forward model residual associated with the PDE-constrained algorithm across each inverse iteration.

As is apparent from FIGS. 31A-31C, the PDE-constrained algorithm achieves speedup factors of 16.6 and 10.7 compared to the unconstrained algorithm, using the $SP_1$ and $SP_3$ models, respectively. The difference in computation times between the $SP_1$ and $SP_3$ models is surprisingly minimal, suggesting that the traditional computation superiority of the $SP_1$ model over higher order models is diminished when considering optical properties outside the diffuse regime. The similarities in computation performance between then $SP_1$ and $SP_3$ models are evident by considering the value of the objective function over inverse iterations, as shown in FIG. 31B, and the value of the forward model error over inverse iterations, as shown in FIG. 31C. The performance of the $SP_3$ model is thus almost identical to that of the $SP_1$ model.

Disk Phantom: Case 3

The optical properties of the third phantom are chosen to be well outside the diffuse regime, with highly absorbing regions (i.e., $\mu_a$=1.0 cm$^{-1}$) and a region with low scattering values (i.e., $\mu'_s$, =2.5 cm$^{-1}$), all inside a moderately diffuse background. The background properties are $\mu_a$=0.1 cm$^{-1}$ and $\mu'_s$=10.0 cm$^{-1}$. These absorption and scattering values closely approximate the properties of most biological media.

Reconstructions of $\mu_a$ and $\mu'_s$ are presented in FIGS. 32A-32J. In particular, FIGS. 32A-32E show $\mu_a$ distribution in the second phantom based on an exact distribution, $SP_1$ unconstrained reconstruction, $SP_1$ PDE-constrained reconstruction, $SP_3$ unconstrained reconstruction, and $SP_3$ PDE-constrained reconstruction, respectively. FIGS. 32F-32J show $\mu'_s$ distribution in the second phantom based on an exact distribution, $SP_1$ unconstrained reconstruction, $SP_1$ PDE-constrained reconstruction, $SP_3$ unconstrained reconstruction, and $SP_3$ PDE-constrained reconstruction, respectively.

As in the case of the first two phantoms, including the diffuse phantom, the reconstructions obtained with the $SP_3$ models are more accurate than those obtained with the $SP_1$ model. In contrast to the diffuse phantom (i.e., the first phantom), the difference in accuracy between the $SP_1$ and $SP_3$ models is only marginal, as the correlation coefficients of the reconstructions obtained with the $SP_3$ model are only 0.02 larger than the correlation coefficients of reconstructions with the $SP_1$ model. Furthermore, the accuracies of the $\mu_a$ and $\mu'_s$ reconstructions are similar, with a correlation coefficient between 0.71 and 0.73. Table 24 presents the correlation coefficients for the third phantom.

TABLE 24

Correlation coefficient between reconstruction and analytical solutions for the third phantom

|  | $SP_1$ | $SP_1$ (PDE) | $SP_3$ | $SP_3$ (PDE) |
|---|---|---|---|---|
| c ($\mu_a$) [%] | 0.71 | 0.72 | 0.73 | 0.73 |
| c ($\mu'_s$) [%] | 0.71 | 0.71 | 0.73 | 0.73 |

Figure 33:
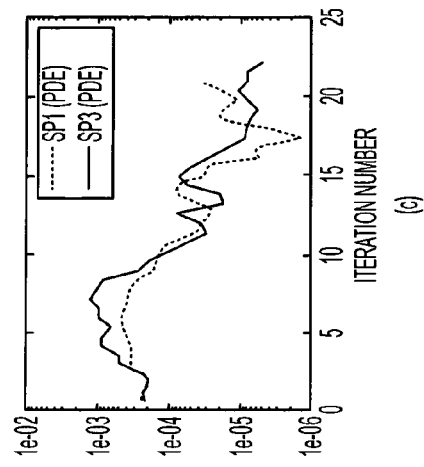
FIGS. 33A-33C are graphs reflecting the performance profile of the different reconstruction models applied to the third disk phantom, according to one or more embodiments of the disclosed subject matter.
Figure 33:
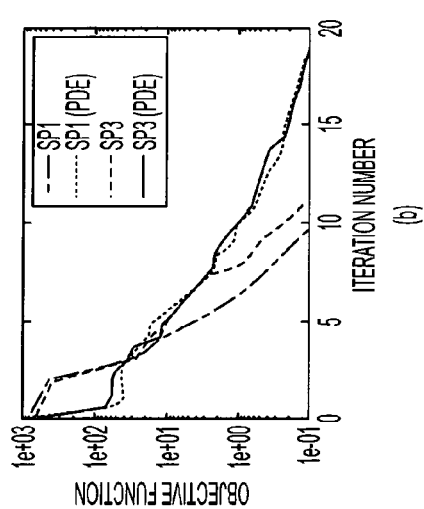
Figure 33:
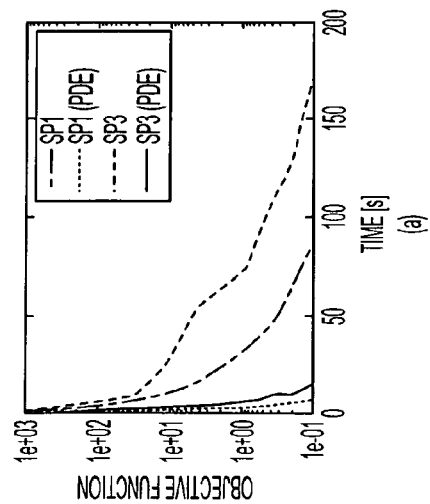
Figure 34:
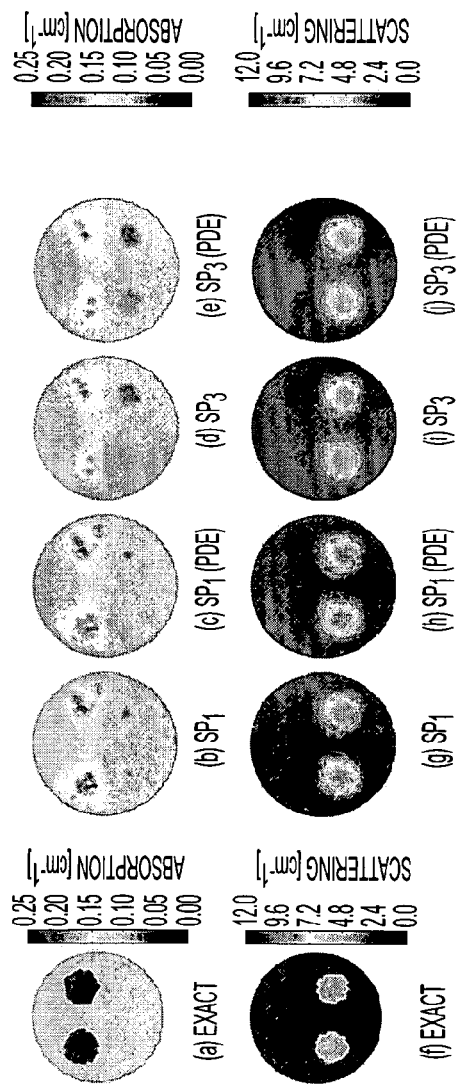
FIGS. 34A-34J show the distribution of exact values and reconstruction images of absorption and scattering coefficients computed using different models for a fourth disk phantom, according to one or more embodiments of the disclosed subject matter.

FIGS. 33A-33C illustrate the performance profile of the reconstruction algorithms on the third phantom. In particular, the value of the objective function over time is plotted for each of the four reconstruction methods in FIG. 33A and at the conclusion of each inverse iteration in FIG. 33B. FIG. 33C shows the evolution of the forward model residual associated with the PDE-constrained algorithm across each inverse iteration.

As is apparent from FIGS. 33A-33C, computationally, the PDE-constrained algorithm performs significantly better than the unconstrained algorithm, achieving speedup factors of approximately 12.3 and 15.2 with the $SP_1$ and $SP_3$ models, respectively.

Disk Phantom: Case 4

The optical properties of the fourth phantom are chosen to be well outside the diffuse regime, with two absorbing inclusions (i.e., $\mu_a$=0.2 cm$^{-1}$) and two regions with low scattering values (i.e., $\mu'_s$=6.0 cm$^{-1}$), all inside a moderately diffuse background. The background properties are $\mu_a$=0.1 cm$^{-1}$ and $\mu'_s$=10.0 cm$^{-1}$.

Reconstructions of $\mu_a$ and $\mu'_s$ are presented in FIGS. 34A-34J. In particular, FIGS. 34A-34E show $\mu_a$ distribution in the second phantom based on an exact distribution, $SP_1$ unconstrained reconstruction, $SP_1$ PDE-constrained reconstruction, $SP_3$ unconstrained reconstruction, and $SP_3$ PDE-constrained reconstruction, respectively. FIGS. 34F-34J show $\mu'_s$ distribution in the second phantom based on an exact distribution, $SP_1$ unconstrained reconstruction, $SP_1$ PDE-constrained reconstruction, $SP_3$ unconstrained reconstruction, and $SP_3$ PDE-constrained reconstruction, respectively.

Reconstruction images of the $\mu'_s$ are more accurate than reconstructions of the $\mu_a$, as the scattering objects are very accurately resolved while the absorbing objects appear as single continuous objects, as shown in FIGS. 34A-34J. The $SP_3$ model achieves better resolution of the absorbing objects compared to the $SP_1$ model. Table 25 presents the correlation coefficients for the fourth phantom. As is apparent from Table 25, the reconstructions with the $SP_3$ model are more accurate than the reconstructions with the $SP_1$ model.

TABLE 25

Correlation coefficient between reconstruction
and analytical solutions for the fourth phantom

|  | $SP_1$ | $SP_1$ (PDE) | $SP_3$ | $SP_3$ (PDE) |
|---|---|---|---|---|
| c ($\mu_a$) [%] | 0.64 | 0.64 | 0.67 | 0.67 |
| c ($\mu'_s$) [%] | 0.77 | 0.77 | 0.87 | 0.87 |

Figure 35:
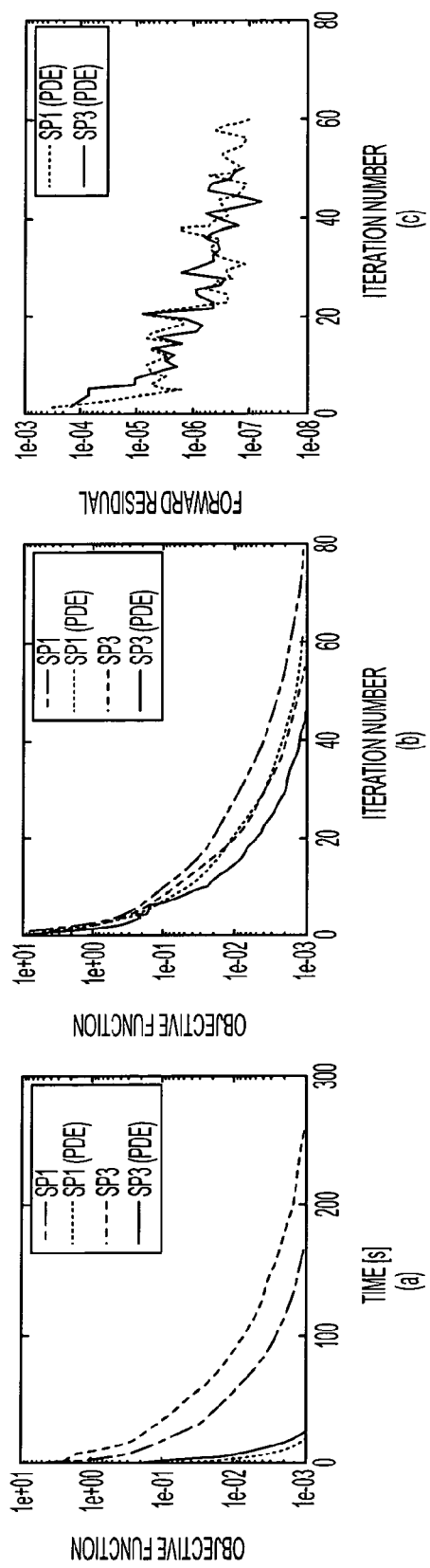
FIGS. 35A-35C are graphs reflecting the performance profile of the different reconstruction models applied to the fourth disk phantom, according to one or more embodiments of the disclosed subject matter.
Figure 36:
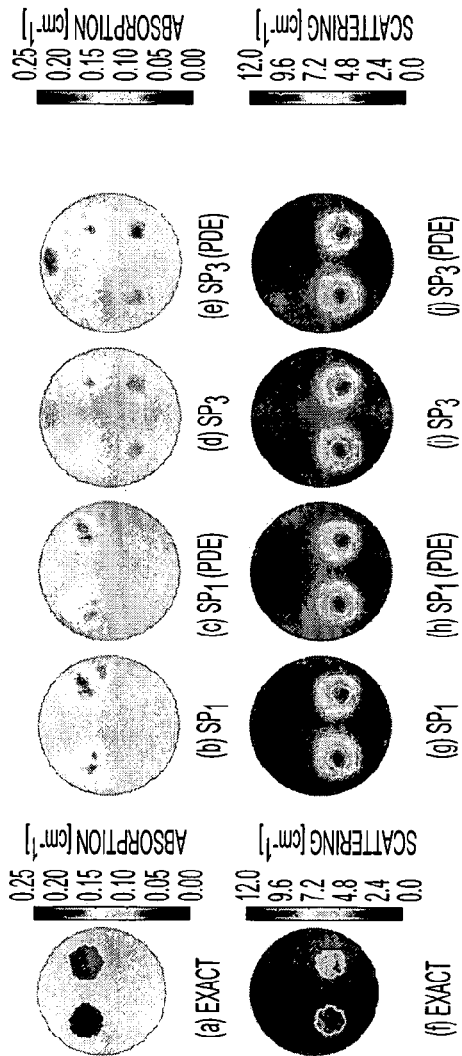
FIGS. 36A-36J show the distribution of exact values and reconstruction images of absorption and scattering coefficients computed using different models for a fifth disk phantom, according to one or more embodiments of the disclosed subject matter.

FIGS. 35A-35C illustrate the performance profile of the reconstruction algorithms on the fourth phantom. In particular, the value of the objective function over time is plotted for each of the four reconstruction methods in FIG. 35A and at the conclusion of each inverse iteration in FIG. 35B. FIG. 35C shows the evolution of the forward model residual associated with the PDE-constrained algorithm across each inverse iteration.

As is apparent from FIGS. 35A-35C, computationally, the PDE-constrained algorithm performs significantly better than the unconstrained algorithm, achieving speedup factors of approximately 9.6 and 9.7 with the $SP_1$ and $SP_3$ models, respectively.

Disk Phantom: Case 5

The optical properties of the fifth phantom are chosen to have moderately absorbing inclusions (i.e., $\mu_a$=0.2 cm$^{-1}$) and two regions with low scattering values (i.e., $\mu'_s$=4.0 cm$^{-1}$) in a moderately diffuse background. The background properties are $\mu_a$=0.1 cm$^{-1}$ and $\mu'_s$i=10.0 cm$^{-1}$. Thus, the fifth phantom is similar to the fourth phantom, but with a different value for the low scattering regions.

Reconstructions of $\mu_a$ and $\mu'_s$ are presented in FIGS. 36A-36J. In particular, FIGS. 36A-36E show $\mu_a$ distribution in the second phantom based on an exact distribution, $SP_1$ unconstrained reconstruction, $SP_1$ PDE-constrained reconstruction, $SP_3$ unconstrained reconstruction, and $SP_3$ PDE-constrained reconstruction, respectively. FIGS. 36F-36J show $\mu'_s$ distribution in the second phantom based on an exact distribution, $SP_1$ unconstrained reconstruction, $SP_1$ PDE-constrained reconstruction, $SP_3$ unconstrained reconstruction, and $SP_3$ PDE-constrained reconstruction, respectively.

As in the case of the fourth phantom, the $SP_3$ model performs better than the $SP_1$ model and the $\mu'_s$ reconstruction is more accurate than the $\mu_a$ reconstruction. However, in contrast to the fourth phantom, where the $SP_3$ model performed significantly better than the $SP_1$ model, the differences in accuracy between the $SP_1$ and $SP_3$ models are smaller in this example, as illustrated by the correlation coefficients listed in Table 26. The accuracy of the $\mu_a$ reconstruction decreases compared to reconstruction of the fourth phantom 5.6, where the scattering inclusions were defined by $\mu'_s$=6.0 cm$^{-1}$ The accuracy of the $\mu'_s$ reconstructions with the $SP_3$ model thus remains relatively unchanged, while the accuracy of the $\mu'_s$ reconstructions with the $SP_1$ model improves. This change may be due to the significant decrease in the scattering values of the inclusions ($\mu'_s$=6.0 cm$^{-1}$ to $\mu'_s$=4.0 cm$^{-1}$). It is expected that approximations to the ERT will perform increasingly poorly as the optical properties of the tissue approach low-scattering media (i.e., void-like).

TABLE 26

Correlation coefficient between reconstruction
and analytical solutions for the fifth phantom

|  | $SP_1$ | $SP_1$ (PDE) | $SP_3$ | $SP_3$ (PDE) |
|---|---|---|---|---|
| c ($\mu_a$) [%] | 0.61 | 0.61 | 0.62 | 0.62 |
| c ($\mu'_s$) [%] | 0.82 | 0.82 | 0.86 | 0.86 |

Figure 37:
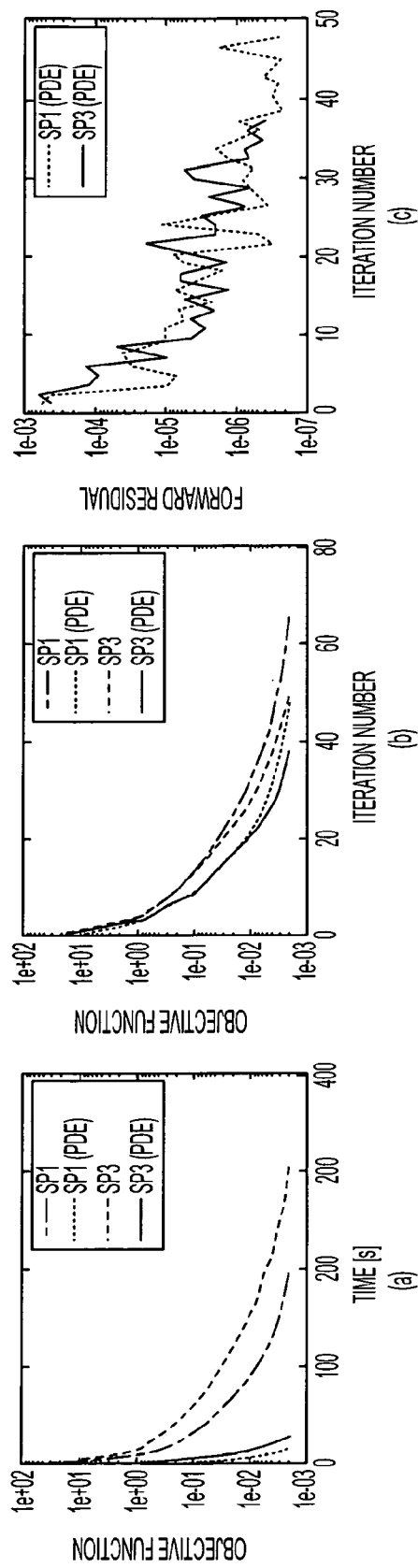
FIGS. 37A-37C are graphs reflecting the performance profile of the different reconstruction models applied to the fifth disk phantom, according to one or more embodiments of the disclosed subject matter.

FIGS. 37A-37C illustrate the performance profile of the reconstruction algorithms on the fifth phantom. In particular, the value of the objective function over time is plotted for each of the four reconstruction methods in FIG. 37A and at the conclusion of each inverse iteration in FIG. 37B. FIG. 37C shows the evolution of the forward model residual associated with the PDE-constrained algorithm across each inverse iteration.

As is apparent from FIGS. 37A-37C, computationally, the PDE-constrained algorithm performs significantly better than the unconstrained algorithm, achieving speedup factors of approximately 11.1 and 10.5 with the $SP_1$ and $SP_3$ models, respectively.

Finger Phantom

Figure 38B:
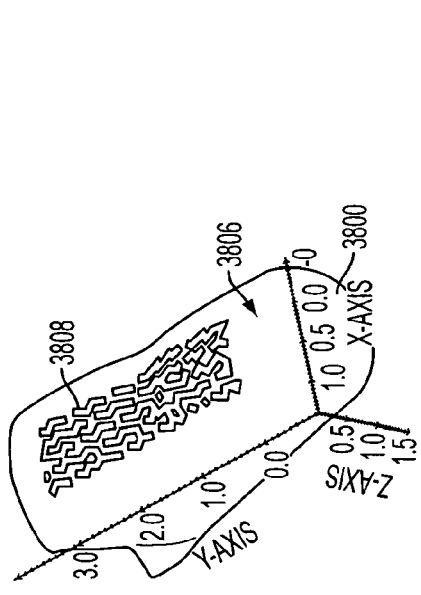
FIGS. 38A-38B show the posterior surface and the anterior surface, respectively, of a finger-like phantom and exemplary locations of sources and detectors, according to one or more embodiments of the disclosed subject matter.
Figure 38A:
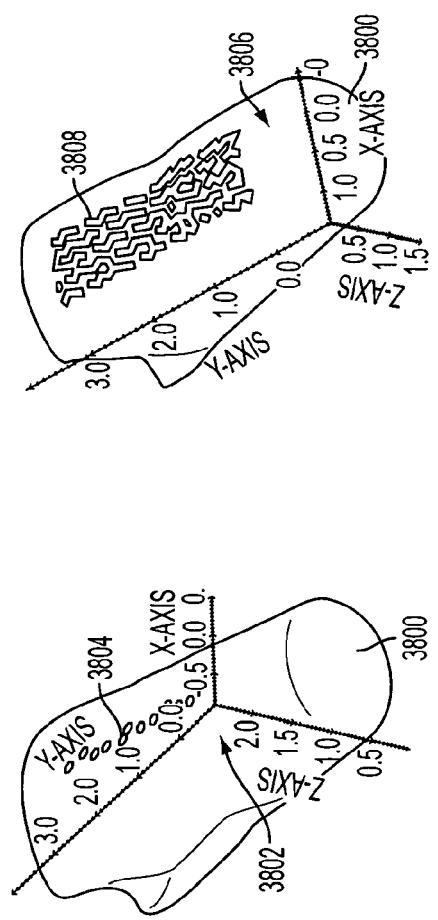

In this section, a three-dimensional numerical phantom is considered, which is based on the surface geometry of a human finger. The source and detector configuration of this phantom is modeled after a trans-illumination imaging setup, where the finger 3800 is illuminated on the posterior (dorsal) side 3802 and escaping photons are measured on the anterior (palmar) side 3806, as shown in FIGS. 38A-38B. For example, eleven (11) distinct point sources 3804 (only one is labeled in FIG. 38A) can be provided, with one-hundred and fifty-five (155) detector points 3808 (only one is labeled in FIG. 38B) on the anterior side 3806.

Figure 39:
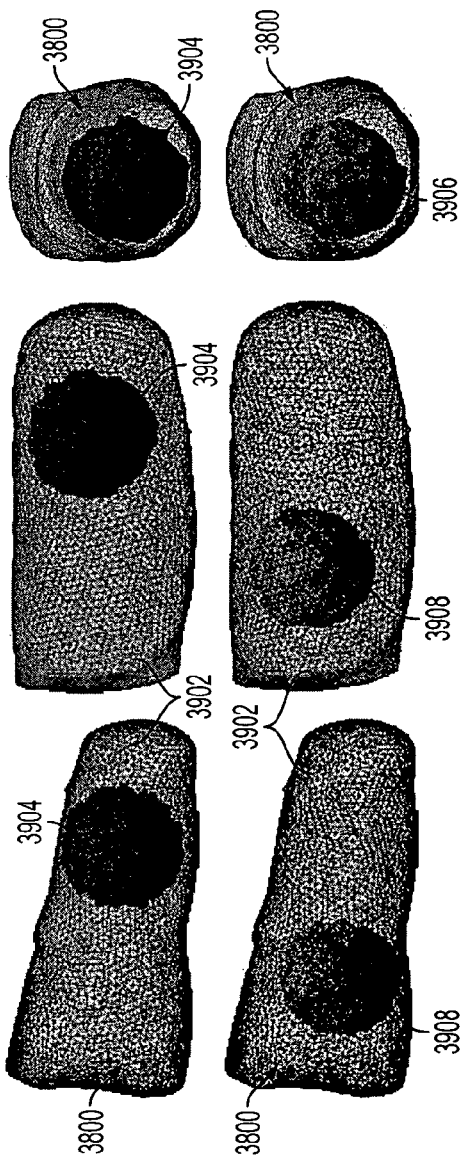
FIG. 39 shows different views of a finger-like phantom showing the locations of an absorbing inclusion (top row) and a scattering inclusion (bottom row), according to one or more embodiments of the disclosed subject matter.

Two cases of the finger phantom are considered. In both cases, one inclusion 3904 with elevated absorption and one inclusion 3908 with lower scattering than the background medium 3902 are provided, as illustrated in FIG. 39. Note that FIG. 39 shows different views of the finger phantom. The section of the finger under consideration is approximately 4.0 cm in length (y-axis) and has width and height of approximately 2.0 cm. The inclusions are spheres with a 1.5 cm diameter. The reconstruction process is allowed to continue until the inverse error decreases by a factor of 0.0001 (or to 0.01% of the original value).

Optical properties are chosen to closely resemble those typically found in and around the proximal interphalangeal (PIP) joint of the human hand. The inclusions are chosen to resemble regions of high absorption and low scattering that can be found in and around the PIP joint cavity. In the first case, the background media is defined with $\mu_a$=0.01 cm$^{-1}$ and $\mu'_s$=12.5 cm$^{-1}$ (g=0.95); the absorption inclusion has $\mu_a$=0.05 cm$^{-1}$ and the scattering inclusion has $\mu'_s$=10.0 cm$^{-1}$. The second finger phantom is similar, with only differences in the value of the optical properties. The background media is defined with $\mu_a$=0.1 cm$^{-1}$ and $\mu'_s$=12.5 cm$^{-1}$ (g=0.95); the absorption inclusion has $\mu_a$=0.25 cm$^{-1}$ and the scattering inclusion has $\mu'_s$=7.5 cm$^{-1}$. The reconstruction of these optical properties allow for a determination of how accurately each algorithm can determine the underlying optical properties and their individual computational efficiency. Moreover, these simulations closely resemble clinical applications.

The accuracy of reconstructions obtained with the $SP_1$ and $SP_3$ models are summarized in Tables 27 and 28, respectively. In both cases, the reconstructions obtained with the $SP_3$ model are more accurate than the reconstructions obtained with the SP1 model. The differences between the models are more significant for the first finger phantom.

TABLE 27

Correlation coefficient between reconstruction and analytical solutions for the first finger phantom

|  | $SP_1$ | $SP_1$ (PDE) | $SP_3$ | $SP_3$ (PDE) |
|---|---|---|---|---|
| c ($\mu_a$) [%] | 0.54 | 0.54 | 0.67 | 0.66 |
| c ($\mu'_s$) [%] | 0.60 | 0.60 | 0.71 | 0.71 |

TABLE 28

Correlation coefficient between reconstruction and analytical solutions for the second finger phantom

|  | $SP_1$ | $SP_1$ (PDE) | $SP_3$ | $SP_3$ (PDE) |
|---|---|---|---|---|
| c ($\mu_a$) [%] | 0.65 | 0.65 | 0.72 | 0.72 |
| c ($\mu'_s$) [%] | 0.60 | 0.60 | 0.67 | 0.67 |

Figure 40:
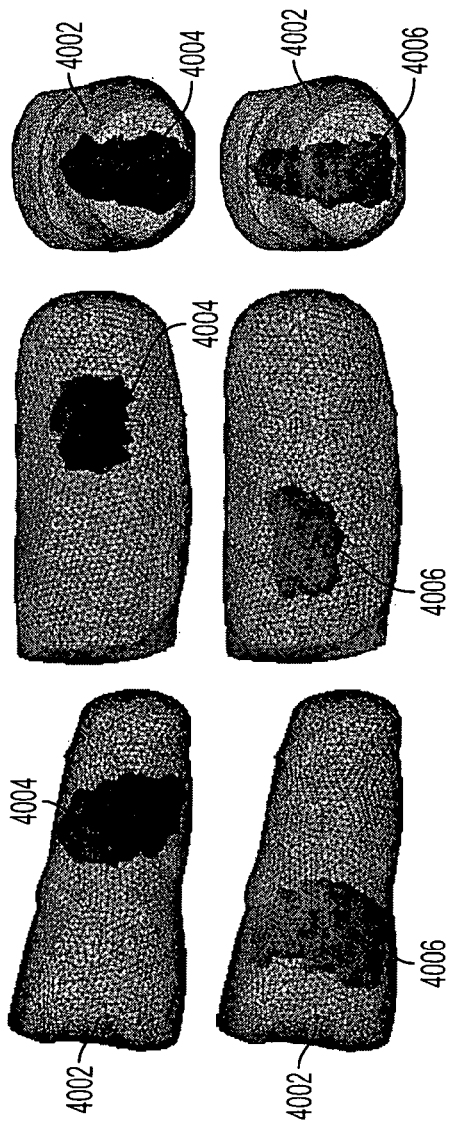
FIG. 40 shows different views of a three-dimensional reconstruction image of a finger-like phantom showing the locations of the absorption inclusion (top row) and the scattering inclusion (bottom row), according to one or more embodiments of the disclosed subject matter.
Figure 41:
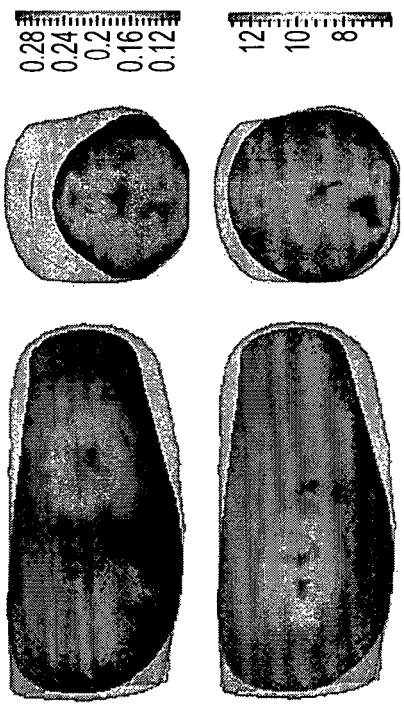
FIG. 41 shows cross-sectional slices of the finger-like phantom based on the reconstruction images obtained with a PDE-constrained $SP_3$ model of the absorption coefficient (top row) and the scattering coefficient (bottom row), according to one or more embodiments of the disclosed subject matter.
Figure 42:
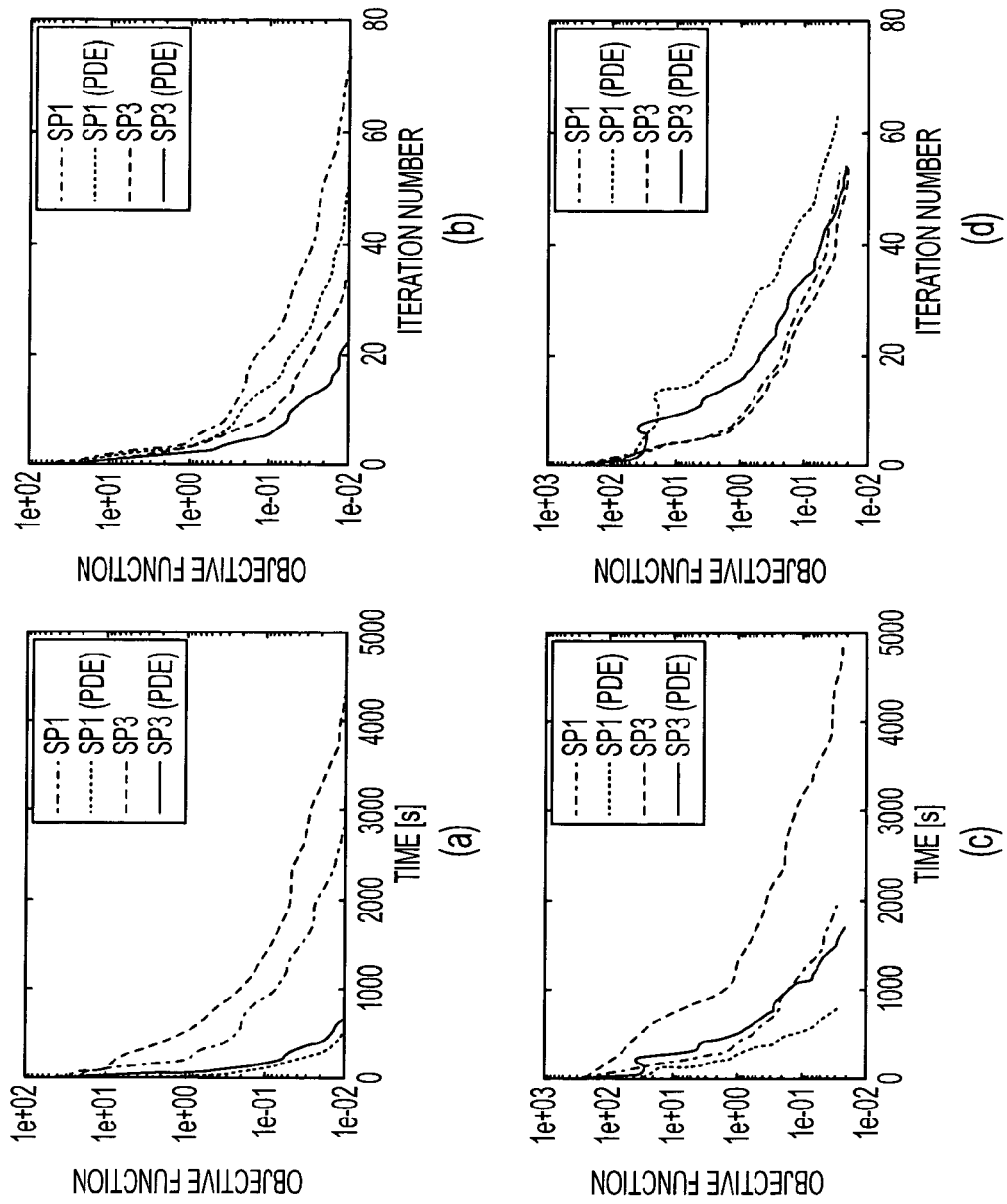
FIGS. 42A-42D are graphs reflecting the performance profile of the different reconstruction models applied to first and second finger-like phantoms, according to one or more embodiments of the disclosed subject matter.

An example of the absorption and scattering coefficient maps obtained with the $SP_3$ model using the PDE-constrained algorithm for the second finger phantom is shown in FIG. 40. In particular, the absorption inclusion 4004 in media 4002 corresponds to the absorption inclusion 3904 of FIG. 39, while the scattering void 4006 corresponds to the scattering inclusion 3906 of FIG. 39. FIG. 41 further illustrates cross-section slices inside the finger phantom of the reconstruction images of the absorption (top row) and scattering (bottom row) coefficients obtained with the PDE-constrained $SP_3$ models for the second finger phantoms. Thus, the algorithm is able to accurately locate the inhomogeneities and can accurately identify the value of the absorption and scattering coefficients in the same general location.

FIGS. 42A-42D illustrate the performance profile of the reconstruction algorithms on the first and second finger phantoms. In particular, the value of the objective function over time is plotted for each of the four reconstruction methods for the first and second finger phantoms in FIGS. 42A and 42C, respectively, and at the conclusion of each inverse iteration for the first and second finger phantoms in FIGS. 42B and 42D, respectively.

As is apparent from FIGS. 42A-42D, the PDE-constrained algorithms significantly outperform the unconstrained algorithms in the reconstruction of both phantoms. However, the computational efficiencies gained by the PDE-constrained algorithm are more significant in solving for the first phantom. In that case, computational gain factors of up to five (5) are obtained. Another computational aspect of interest is the system memory (RAM) requirements of each algorithm, as these two finger phantoms closely resemble clinical applications. Reconstructions with the $SP_1$ model requires up to 177.5 MB, while up to 212.7 MB are used by the $SP_3$ algorithm. These computational requirements are on the order of the RAM found in typical desktop computers (e.g., 12 GB of RAM was used in the desktop computer for these studies). This reflects the efficient memory management afforded by the use of the disclosed algorithms and models, which efficiency is expected to translate to other DOT applications and is not intended to be limited to the specific simulations presented herein. In particular, similar efficiencies can be realized in a clinical setting, for example, in RA diagnosis via DOT imaging, as discussed in detail below.

Objective Function for Use with Clinical Data

When working with experimental data, the objective function of the inverse problem can be modified. The general form of the objective function that is used to solve the unconstrained optimization problem is given by:

$$f(\mu, u) = \frac{1}{2}(M - P)^T\overline{(M - P)}. \quad (10.1)$$

Since the absolute strength of the boundary source (W cm$^{-2}$ sr$^{-1}$) (e.g., a laser) may not be precisely known, it may not be possible to directly compare the predicted measurement values (P) with the true measurement data (M). The inability to directly compare these vectors can be due to a mismatch in scale that can occurs when the source strength is not precisely known. As a result, the true measurement data can be normalized by the average overall measured intensity.

The normalized measurement data ($\tilde{M}$) can be given by:

$$\tilde{M}_{ij} = (\overline{M})^{-1} M_{ij}. \quad (10.2)$$

The indices i∈S and j∈D denote all possible sources and detectors, respectively. Here, $\overline{M}$ represents the average measured intensity, which is a complex valued number when considering frequency domain DOT, and is given by:

$$\overline{M} = \frac{1}{SD}\sum_{i=1}^{S}\sum_{j=1}^{D}(M)_{ij}. \quad (10.3)$$

Mirroring the normalization of M, the predicted detector measurements P can be normalized in a similar manner. The normalized predicted partial current can be computed as follows:

$$\tilde{P} = (\overline{P})^{-1} P. \quad (10.4)$$

Here, P is the average predicted partial current across all source-detector pairs and is defined as $$\overline{P} = \frac{1}{SD}\sum_{i=1}^{S}\sum_{j=1}^{D}(Qu)_{ij}. \quad (10.5)$$

After incorporating these changes, the augmented objective function can be stated as follows:

$$f(\mu, u) = \frac{1}{2}(\tilde{M} - \tilde{P})^T\overline{(\tilde{M} - \tilde{P})}. \quad (10.6)$$

The right hand side of the adjoint equation is more complicated because P itself is a function of u, the variable over which differentiation occurs. The adjoint equation for the constrained and unconstrained approach is discussed in detail above and is given by Eqn. 9.21. A numerical recipe for using the solution to the adjoint equation in the PDE-constrained algorithm is also described above and given by Eqn. 9.49. Given the changes introduced as a result of normalizing measurement data, the correct adjoint equation becomes:

$$A^T \lambda = Q^T \left( \frac{\tilde{P}^T (\tilde{M} - \tilde{P})^* \frac{1}{SD} 1 - (\tilde{M} - \tilde{P})^*}{\tilde{P}} \right). \quad (10.7)$$

Normalization of each element of the error (or difference) vector $(\tilde{M}-\tilde{P})_{ij}$ by the corresponding norm of the measurement element (i.e., $|\tilde{M}|_{ij}$) often leads to improved convergence (where $i \in S$ and $j \in D$ denote the source-detector pair). In this case, the objective function can be redefined as:

$$f(\mu, u) = \frac{1}{2} \frac{\left(\tilde{M} - \frac{Qu}{\tilde{P}}\right)^T \left(\tilde{M} - \frac{Qu}{\tilde{P}}\right)}{\tilde{M}^T \tilde{M}}. \quad (10.8)$$

The only change to Eqn. 10.7 is the use of the appropriate normalized terms when computing the difference between predicted measurements and true measurements, $(\tilde{M}-\tilde{P})$.

Clinical Data

The clinical data includes 219 PIP joints that were imaged using a sagittal trans-illumination frequency-domain DOT scanner. PIP joints II-IV were imaged on the dominant hand of 33 subjects with RA and on both hands of 20 healthy control subjects, resulting in 99 joints from subjects with RA and 120 joints of subjects without RA. Scanning was performed at 600, 300, and 0 MHz. The source laser illuminated the joint on the posterior (dorsal) side and escaping photons were measured on the anterior (palmar) side using an intensified CCD-based detection system. In total, 11 distinct point sources 4304 (only three of which are specifically referenced in FIG. 43A) and over 100 detector points 4306, as shown in FIG. 43B were defined for each joint 4302.

An example of transillumination from a single surface source, as captured by the ICCD-based detector system, on the posterior (or palmar) surface of the finger is presented in FIGS. 44A-44B. In particular, the image in FIG. 44A is for a PIP joint belonging to a subject with RA, while FIG. 44B is for a PIP joint belonging to a healthy subject. The value of the detector mesh points can be obtained by mapping those pixels onto the ICCD image and then extracting the measured data at the corresponding pixels.

Reconstruction Results

Reconstruction of the absorption and scattering coefficients of each imaged joint is performed using the PDE-constrained $SP_3$ algorithm. Qualitatively, the images appear as expected, with regions of low absorption and scattering within the area where the PIP joint cavity is expected. Each reconstruction requires between 150 to 200 MB of RAM and is completed in less than 15 minutes. The objective function typically decreases to between 1.0% and 10.0% of the original objective function value. The 10,000 fold reduction of the inverse error from its original value achieved in the numerical simulations described above is not, in general, obtained in the reconstructions of clinical data. The inability to obtain more substantial reductions in the objective function can be attributed to the loss of information that arises from normalizing the measurement data by the average overall measured intensity. However, reconstruction results without normalization may be susceptible to inaccuracies and may be otherwise unreliable when using clinical data. Indeed, attempting to reconstruct clinical data without performing the aforementioned normalization may lead to premature termination of the reconstruction process (i.e., the algorithm cannot progress beyond the initial guess) or if left unchecked, the value of the objective function can increase dramatically, which may occur if a specific constraint on allowable values of the objective function is not added, such as requiring the objective function to constantly decrease at each inverse iteration.

Figure 45:
FIGS. 45A-45D and FIGS. 46A-46D show absorption coefficient and scattering coefficient cross-sections of distinct joints from subjects with and without RA, according to one or more embodiments of the disclosed subject matter.
Figure 46:

The reconstruction images of absorption and scattering within and around the imaged PIP joint show distinct differences between subjects with RA and the control group. The $\mu_a$ and $\mu'_s$ images of 40 joints are presented in FIGS. 45A-45D and FIGS. 46A-46D. In particular, FIGS. 45A and 46A show, in columnar form, the absorption coefficients in cross-section of distinct joints from subjects without RA. FIGS. 45B and 46B show, in columnar form, the absorption coefficients in cross-section of distinct joints from subjects with RA. FIGS. 45C and 46C show, in columnar form, the scattering coefficients in cross-section of distinct joints from subjects without RA. FIGS. 45D and 46D show, in columnar form, the scattering coefficients in cross-section of distinct joints from subjects with RA.

In FIGS. 45A-45D and 46A-46D, it is clear that compared to joints of healthy subjects, subjects with RA have elevated regions of absorption and scattering around the PIP joint. In these images, a region of low scattering and absorption is identifiable around the location where the PIP joint is expected. This region may correspond to the synovial cavity of the joint, which is expected to have lower absorption and scattering compared to the surrounding tissues (bone, muscle, ligament, tendon). This region is identifiable in all joints of healthy subjects and some joints of subjects with RA. However, these same regions exhibit elevated absorption and scattering (compared to the background) in joints of subjects with RA. This may suggest that the synovial cavity of these joints has experienced significant changes in physiology that results in an elevated concentration of absorbers and scatterers. Such changes can be expected due to the onset of symptoms associated with RA.

TABLE 29

Summary of values assigned to reconstruction variables

| Parameter Name | Value |
| --- | --- |
| Background $\mu_a$ | 0.3 cm$^{-1}$ |
| Background $\mu_s$ | 200.0 cm$^{-1}$ |
| Anisotropy factor g | 0.95 |
| Refractive index of medium n | 1.4 |
| Refractive index of air n | 1.0 |
| Modulation frequency $\omega$ | 600.0 MHz |
| Speed of light in medium c | 299.87 × 10$^8$ |
| GMRES forward model tolerance ($\tau$) | 1.0 × 10$^{-12}$ |
| GMRES adjoint model tolerance ($\tau$) | 1.0 × 10$^{-4}$ |
| GMRES inexact forward model tolerance ($\tau$) | 1.0 × 10$^{-4}$ |
| GMRES maximum number of iterations | 500 |
| GMRES restart iterations (mr) | 50 |
| Boundary regularization | No |
| Inverse tolerance | 0.01 |
| Minimum decay rate | 1.0 × 10$^{-8}$ |
| Boundary source power | 1.0 W cm$^{-2}$ sr$^{-1}$ |
| Discrete ordinates | S$_{12}$ (168) |
| Absorption rescaling range | [0.0, 0.4] cm$^{-1}$ |
| Scattering rescaling range | [0.0, 400.0] cm$^{-1}$ |

The reconstruction parameters used to obtain the above noted results are summarized by Table 29. The absorption and scattering coefficients were rescaled by transforming the absorption range of [0.0, 0.4] cm$^{-1}$ and the scattering range of [0.0, 1.0] cm$^{-1}$. This rescaling does not imply that the acceptable solutions were restricted to lie within this range. Rather, the acceptable range of solutions itself is not restricted.

Analysis of SPN Reconstruction Data with CAD

The reconstruction results obtained with the SPN model can then be used to diagnose RA. The k-fold cross-validation technique can be used to gauge the ability to diagnose RA with this new data. Here, approximately ⅔ of the data is used to train and ⅓ is used to test. The training set includes 22 subsets with RA (or 66 PIP joints) and 14 healthy individuals (or 84 PIP joints), together comprising 150 distinct joints. The testing set includes 11 subjects with RA (or 33 PIP joints) and six healthy patients (or 36 PIP joints). The allocation of subjects into the training of the testing group is done randomly to help minimize any potential bias.

The rule for selecting the top thirty features for use in the optimization algorithm is given by:

$$Y^*|(Se, Sp) = Se + Sp + \alpha L_{Se} + \beta L_{Sp} - \delta d - 1. \quad (10.9)$$

This term, referred to as "augmented" Youden index, is a function of sensitivity (Se) and specificity (Sp), and the lower bounds of the confidence intervals (for example, 95% confidence interval) of Se and Sp are given by $L_{Se}$ and $L_{Sp}$, respectively.

The k-fold method can be used to enhance the cross-validation process. The process is summarized by the flowchart in FIG. 47. With k=2, the entire data set 4702 can be segmented into two sets, a training set 4706 and a testing set 4704. The training set 4706 is subjected to the data-mining process 4708, which yields a set of optimal feature vectors 4712 and the corresponding choice of classification algorithm 4710 for the training data. The testing set is not used until the optimal classifier (features and classification algorithm) is chosen. The resulting classifier 4714 is used to subsequently evaluate at 4716 the ability to diagnose RA with the testing data. Performance, in particular sensitivity and/or specificity, can be evaluated at 4718.

Figure 48:
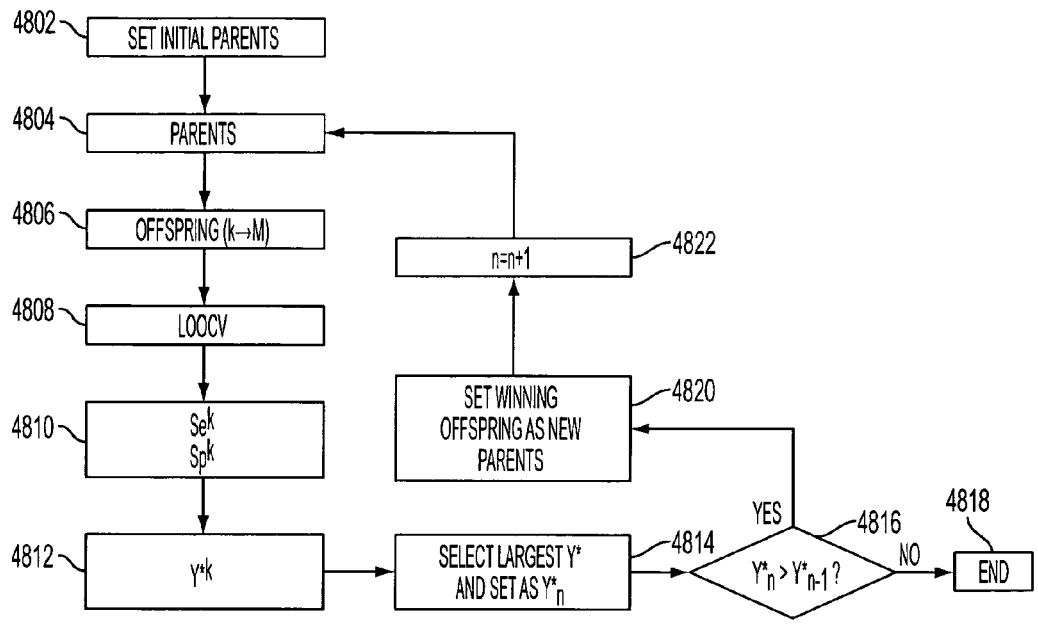
FIG. 48 is a process flow chart of an exemplary method for data mining to select optimal features and classification algorithm for diagnosing RA, according to one or more embodiments of the disclosed subject matter.

The data mining process that selects optimal features and the best classification algorithm for diagnosing RA from DOT images is summarized by the flowchart in FIG. 48. This process can be performed on reconstruction images obtained with the SP$_1$, SP$_3$, and/or ERT models. For example, an evolution strategy algorithm can be employed. Such an algorithm may be a single-parent evolution strategy or greedy feature selection rule. At 4802, an initial set of parent features is set and becomes the first stage of parents at 4804. At 4806, at total of M mutants are created an compete with their parents. A leave one-out cross-validation procedure (LOOCV) can be performed at 4808. Subsequently, the sensitivity (Se) and specificity (Sp) for each generation k can be determined at 4810 and the augmented Youden index (Y*) calculated at 4812. Of all the mutants and their parents for generation k, the combination with the largest Y* can be selected at 4814. At 4816, it is determined if Y*$_n$ has improved with respect to the previous generation. If not, the process can terminate at 4818. Otherwise, the combination can be set as the new parents at 4820 and the process repeated for the next generation after incrementing a counter at 4822.

For each data set (i.e., SP$_1$, SP$_3$, or ERT based reconstructions), the sensitivity and the specificity obtained when the data mining results are used to classify the testing data is reported. Classification results are summarized in Tables 30 and 31. The sensitivity and specificity (and their respective confidence intervals) achieved when using the reconstruction images generated with the SP$_1$, SP$_3$, and ERT models are summarized in Table 30. The number of true positives (TP), false negatives (FN), true negatives (TN), and false positives (FP) are also summarized in Table 30.

TABLE 30

Classification results for SPN and ERT based reconstructions with the k-fold method

| Model | TP | FN | TN | FP | Se [% (95% CI)] | Sp [% (95% CI)] | Youden | Number of Features |
|---|---|---|---|---|---|---|---|---|
| SP1 | 22 | 11 | 34 | 8 | 66.7 (46.6, 100) | 81.1 (64.8, 100) | 0.48 | 8 |
| SP3 | 29 | 4 | 39 | 3 | 87.9 (78.1, 100) | 92.9 (84.6, 100) | 0.81 | 3 |
| ERT | 30 | 3 | 41 | 1 | 90.9 (83.1, 100.0) | 97.6 (85.1, 100.0) | 0.88 | 5 |

TABLE 31

Name of optimal features selected during the training phase of the k-fold method using SPN and ERT based reconstructions.

| Model | Name of Optimal Features |
|---|---|
| SP1 | F01:ST:a, F04:GT:a, F34:SV:a, F16:VS:a, F03:SV:s, F04:VS:s, F05:VS:s, F04:VT:s |
| SP3 | F01:SV:a, F02:ST:a, F26:VT:a |
| ERT | F01:UV:a, F02:SV:a, F05:SV:a, F02:ST:a. F08:GS:s |

Three criteria can be considered for comparing the performance of the SP$_1$, SP$_3$, and ERT models, for example, computational efficiency, feature extraction optimality, and image classification performance. Computational efficiency refers to the total reconstruction time and the total system resources needed. The reconstruction times with the SP$_1$ and SP$_3$ models are similar, typically requiring less than 15 minutes to complete the reconstruction process. In contrast, the reconstruction time with the ERT model always exceeds 180 minutes. Indeed, the reconstruction time for the SPN models is actually orders of magnitude faster than traditional ERT-based reconstruction algorithms that do not solve the optimization problem using a PDE-constrained approach. Furthermore, the ERT-based reconstruction was obtained with a low order discrete ordinates set (i.e., S6), which is significantly lower than the recommended set of ordinates to accurate capture transport behavior (i.e., >S12). Additionally, reconstructions with the ERT required over 6 GB of RAM, while the SP$_1$ and SP$_3$ models use less than 200 MB of RAM. In the computational efficiency category, the SPN models clearly outperform the ERT model.

The second category is feature extraction optimality, where the number of "optimal" features selected during the training process are compared. Optimal feature vectors with low-dimensionality may be preferable as this helps reduce the probability of over-fitting the data. Over-fitting the data can result in classification results that do not generalize well and therefore may be an unreliable predictor of future performance. In this work, the number of optimal features is eight for the $SP_1$ model, three for the $SP_3$ model, and five for the ERT model. Because of the preference for the fewest possible features to avoid over fitting problems, the $SP_3$ model may be superior in this category to the ERT and $SP_1$ models.

The third category to compare is the classification performance of each of the three models. In this category, the sensitivity and the specificity computed by processing the data set reserved for testing with the classifier that results from the training phase is at issue. In addition to seeking values of the sensitivity and the specificity as close to 100.0% as possible, the 95% confidence interval (CI) for each parameter can also be compared. The CI provides a range within which the true values of the sensitivity and the specificity are expected to exist.

The reconstruction images computed with the $SP_3$ model allow higher sensitivity and specificity values than images obtained with the $SP_1$ model. The $SP_1$ model yields sensitivity of 66.7 (46.6, 100.0)% and specificity of 81.1 (64.8, 100.0)%. The $SP_3$ model clearly outperforms the $SP_1$ model and yields 87.9 (78.1, 100.0)% sensitivity and 92.9 (84.6, 100.0)% specificity. Images computed with the ERT-based algorithm yield 90.9 (83.1, 100.0)% sensitivity and 97.6 (85.1, 100.0)% specificity.

The upper bound of the CI for all models is 100.0%. The lower bound varies between models and between the sensitivity and the specificity. As in the case of the sensitivity and the specificity values, the CI of the ERT are smaller than those obtained with the SPN models. However, the lower bounds of the $SP_3$ model are significantly higher than the lower bounds of the $SP_1$ model. The lower bound of the sensitivity with the $SP_1$ model in only 46.6% which is significantly lower than the 78.1% lower bound that is computed with the $SP_3$ model. Furthermore, the sensitivity computed with $SP_1$ images (66.7%) is lower than the lower bound of the sensitivity computed with the $SP_3$ model (78.1%). Similar results can be observed when comparing the specificity values.

Figure 49:
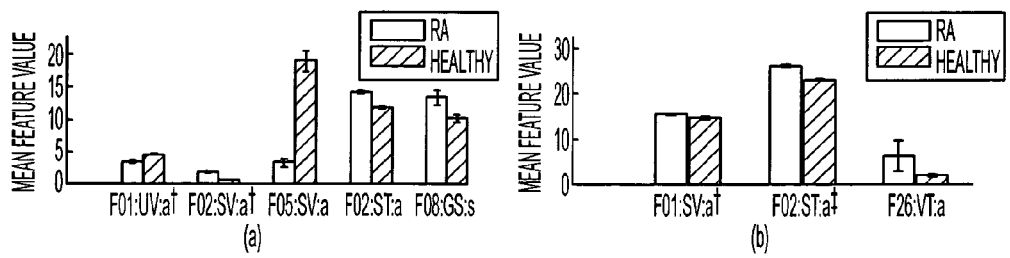
FIGS. 49A-49B are graphs showing the mean value of optimal features selected from the analysis of ERT and $SP_3$ based reconstruction images, respectively, according to one or more embodiments of the disclosed subject matter.

Overall, these results indicate that the $SP_3$-based reconstruction algorithm provides computational advantages over the ERT-based algorithm without sacrificing significant classification accuracy. In contrast, the $SP_1$ model may provide computational advantages compared to the ERT at the expense of classification accuracy. The names of the optimal features selected during the training phase and used in the testing phase are presented in Table 31. The mean value and standard error of the optimal features corresponding to the ERT and $SP_3$ models are plotted in FIGS. 49A and 49B, respectively. With respect to FIG. 49A, features denoted by † are scaled by a factor of 10. With respect to FIG. 49B, features denoted by † and ‡ are scaled by a factor of 50 and 500, respectively.

The three optimal features chosen using the $SP_3$ model are F01:SV:a, F02:ST:a, and F13:VT:a. The first two features are the maximum and minimum values of the three dimensional data and the sum of transverse slices, respectively. The third feature corresponds to the largest coefficient of the Fourier transform of the variance between transverse slices. The five optimal features chosen using ERT-based reconstruction images are F01:UV:a, F02:SV:a, F05:SV:a, F02:ST:a, and F08:GS:s. The first three features are the maximum, minimum, and ratio values of the three dimensional data, respectively. The fourth feature is the minimum of the sum of transverse slices. The fifth feature is a Gaussian mixture model (GMM) parameter, more specifically, the second eigenvalue of the dominant positive Gaussian.

Parallel Computing

The reduced computing resources afforded by use of a PDE-constrained SPN model can take advantage of various computing and processing architectures. For example, the decrease in computational resources allows for implementation of parallel computing strategies that can result in significant acceleration of the image reconstruction process, which would not otherwise be possible with the more resource-intensive ERT algorithm. As discussed above, the SPN model requires significantly less computation resources (~200 MB per finger) compared to the ERT model (>6 GB per finger).

Using the SPN model it is possible to decompose the DOT problem into tasks that can be computed in parallel to achieve close to linear speed-up factor (e.g., ~12× speed-up when using a 12 core computer). For example, parallel computing for use in the DOT problem based on the PDE-constrained SPN algorithm can be exploited in two methodologies, although other methodologies and configurations are also possible according to one or more contemplated embodiments.

A "forward" and an "adjoint" problem can be solved for each source in the DOT problem (i.e., for each projection for which data is captured during the scanning process). The system of equations that can be solved for each source are below:

$$\Delta u^k = -(A^k)^{-1} \left[ (A^k u^k - b) + u^{k^T} \frac{\partial A^k}{\partial \mu} \Delta \mu^k \right] \quad (11.1)$$

$$\lambda^{k+1} = -\left(A(\mu^{k+1})^T\right)^{-1} \left[ Q^T \overline{(Qu^{k+1} - M)} \right] \quad (11.2)$$

Eqn. 11.1 represents an update to forward variable, while Eqn. 11.2 represents an update to the Lagrange (adjoint) variable. Solving these two problems requires ~200 MB with the SPN model (as compared to greater than 6 GB with the ERT model). If the above problems were solved sequentially, algorithmic execution would be slowed and the availability of multiple cores is not taken advantage of. However, this problem can be solved in parallel, assuming a sufficient number of cores are present. For example, if the total memory is ~200 MB*x, where x is the number of sources, then the memory requirements of the PDE-constrained model remains modest for most imaging problems. For example, for DOT imaging of a finger where x=11 (i.e., 11 distinct sources), the memory requirements would be on the order of 2.2 GB. In contrast, the ERT model would require greater than 66 GB (i.e., 6 GB*11) to execute the same problem in parallel. Such a large amount of memory makes the execution of the algorithm impractical with the ERT model.

The line search subroutine can also be accelerated with parallel computing. Each iteration of the inverse problem computes the optimal step size (α). Inside this line-search subroutine, the "adjoint" problem is solved for each source position. The above-noted strategy for parallel computing can be used to decompose this problem and thereby use the parallel cores to obtain a linear speed-up in the reconstruction process. For example, the following problem can be solved inside the line-search subroutine for each source:

$$\lambda^{k+1} = -\left(A(\mu^{k+1})^T\right)^{-1}\left[Q^T\overline{(Q\mu^{k+1} - M)}\right] \quad (11.3)$$

While certain discussions herein have focused on the derivation of equations with respect to frequency domain (FD), embodiments of the disclosed subject matter are not limited thereto. Rather, the detailed derivation of the algorithms for solving the finite volume (FV) simplified spherical harmonics approximation equations (SPN) using a PDE-constrained algorithm can be applied to FD, time-domain (TD), and constant wave (CW) techniques. Moreover, embodiments of the disclosed subject matter are not limited to the specific systems and applications described herein. Rather, the combined PDE-SPN codes can be applied to CW, FD, TD or other approaches. In addition, the disclosed methods can be implemented in finite-element, finite-volume, or in any other configuration.

Moreover, presented above are spherical harmonics approximations using N=3 as an example. However, the order N of the FD-SPN equations can vary, for example, from N=1, 3, 5, and 7 according to one or more contemplated embodiments. It is noted that each of the equations $SP_1$, $SP_3$, $SP_5$, and $SP_7$ are different, but can be derived for proper implementation in the proposed optical tomography algorithm in view of the discussion herein and the above noted derivation.

In one or embodiments of the disclosed subject matter, non-transitory computer-readable storage media and a computer processing systems can be provided. In one or embodiments of the disclosed subject matter, non-transitory computer-readable storage media can be embodied with a sequence of programmed instructions for producing tomographic images by employing PDE-constrained spherical harmonics algorithms, the sequence of programmed instructions embodied on the computer-readable storage medium causing the computer processing systems to perform one or more of the disclosed methods.

In first embodiments, a computer-aided diagnostic system can include a data storage and a processor. The data storage can be configured to receive optical tomographic data representing interrogated tissues of a living animal. The processor can be configured to retrieve the optical tomographic data from the data storage and estimate volumetric properties of the living animal. The processor can be further configured to output display data and/or classification data representing said volumetric properties and/or classifying clinical features of said living animal. The processor can also be configured to execute instructions to estimate said properties using a method for performing a partial differential equation (PDE)-constrained reduced Hessian sequential quadratic programming (rSQP) optimization in which a constraint is defined by a simplified spherical harmonics approximation of the equation of radiative transfer.

In second embodiments, a computer-aided diagnostic system can include a data storage system and a processor. The data storage system can be configured to receive optical tomographic data representing interrogated tissues of a living animal. The processor can be configured to retrieve said optical tomographic data from said data storage system and estimate volumetric properties of the living animal. The processor can be further configured to output display data and/or classification data representing said volumetric properties and/or classifying clinical features of said living animal. The processor can be configured to execute instructions to estimate said properties, the instructions embodying a method for performing a partial differential equation (PDE)-constrained optimization in which optical tomography inverse and forward problems are solved simultaneously and independently. The forward problem can be represented by solving a simplified spherical harmonics approximation of the equation of radiative transfer for simplified spherical harmonics coefficients.

In first or second embodiments or any of the embodiments, the spatially distributed properties can include at least one of: volumetric absorption, volumetric scattering, volumetric fat distribution, volumetric distribution of oxygenated hemoglobin, and/or de-oxygenated hemoglobin, volumetric fluorophore concentration and/or distribution, and/or volumetric quantum yield.

In first or second embodiments or any of the embodiments, the PDE-constrained optimization can include minimizing a Lagrangian function.

In first or second embodiments or any of the embodiments, the processor can include multiple computing cores. The processor can be configured to perform the PDE-constrained optimization in parallel using said multiple cores.

In first or second embodiments or any of the embodiments, the simplified spherical harmonics approximation can include a finite-volume frequency-domain SPN equation.

In first or second embodiments or any of the embodiments, the simplified spherical harmonics approximation can include only real-valued diffusion coefficients.

In first or second embodiments or any of the embodiments, diffusion-like coefficients of the simplified spherical harmonics approximation can be only real-valued.

In first or second embodiments or any of the embodiments, the spherical harmonics approximation can include complex-valued diffusion coefficients.

In first or second embodiments or any of the embodiments, diffusion-like coefficients of the simplified spherical harmonics approximation can be complex-valued.

In first or second embodiments or any of the embodiments, the simplified spherical harmonics approximation can include real-valued moments of radiance coefficients.

In first or second embodiments or any of the embodiments, the simplified spherical harmonics approximation can include complex-valued moments of radiance coefficients.

In first or second embodiments or any of the embodiments, wherein the simplified spherical harmonics approximation can have a model order, N, greater than 1.

In first or second embodiments or any of the embodiments, the simplified spherical harmonics approximation can be an $SP_3$ model.

In first or second embodiments or any of the embodiments, the processor can be configured to use less than or equal to 400 MB of RAM in performing the PDE-constrained optimization.

In first or second embodiments or any of the embodiments, the instructions can be such that the processor may, in performing the optimization, use one tenth of the memory space required based directly on the equation of radiative transfer.

In first or second embodiments or any of the embodiments, the system can include a diffuse optical tomography (DOT) device can be coupled to the data storage for transmitting optical tomographic data thereto. The DOT device can include at least one illumination source and at least one detector.

In first or second embodiments or any of the embodiments, the system can include at least one illumination source can be configured to provide near-infrared radiation to the interrogated tissue.

In first or second embodiments or any of the embodiments, the system can include at least one illumination source can be configured to provide near-infrared radiation at a modulation frequency in a range of 200 MHz to 800 MHz.

In first or second embodiments or any of the embodiments, the system can include a CCD camera or photodiodes connected to an optical fiber that detect radiation emanating from the interrogated tissue.

In first or second embodiments or any of the embodiments, the system can include a display coupled to said processor and configured to display a classification of the clinical features of said living animal outputted by the processor.

In first or second embodiments or any of the embodiments, the processor can be configured to perform the PDE-constrained optimization by implementing a reduced Hessian sequential quadratic programming (rSQP) scheme.

In first or second embodiments or any of the embodiments, the processor can be configured to normalize the optical tomographic data based on average overall measured intensity.

In first or second embodiments or any of the embodiments, the processor can be configured to classify clinical features of the living animal based at least in part on the estimated volumetric properties.

In first or second embodiments or any of the embodiments, the processor can be configured to provide an indication of rheumatoid arthritis in a joint of the animal.

In first or second embodiments or any of the embodiments, the processor can be configured to receive input from a user, and the method for performing the PDE-constrained optimization can be responsive to the input from the user.

In first or second embodiments or any of the embodiments, the processor can be configured to receive input from a user, the method for performing the PDE-constrained optimization can be responsive to the input from the user, and the input from the user can include an indication of a region of interest of the living animal for estimating said properties.

In first or second embodiments or any of the embodiments, the system can include at least one input device coupled to the processor for providing input from a user to the processor.

In first or second embodiments or any of the embodiments, the system can include at least one of a mouse, keyboard, touchscreen, or pointer for providing input from a user to the processor.

In third embodiments or any of the embodiments, a system for optical tomography can employ a partial differential equation (PDE)-constrained reduced Hessian sequential quadratic programming algorithm in a generalized inverse problem of a tomographic reconstruction, wherein a simplified spherical harmonic algorithm can be employed with respect to a corresponding forward problem of the tomographic reconstruction.

In third embodiments or any of the embodiments, the constrained optimization can include minimizing a Lagrangian function.

In third embodiments or any of the embodiments, the system can include multiple computing cores configured to solve the forward and inverse problems in parallel.

In third embodiments or any of the embodiments, the simplified spherical harmonics approximation can be a finite-volume frequency-domain SPN equation.

In third embodiments or any of the embodiments, the simplified spherical harmonics algorithm can include only real-valued diffusion coefficients.

In third embodiments or any of the embodiments, the simplified spherical harmonics algorithm can include complex-valued diffusion coefficients.

In third embodiments or any of the embodiments, the simplified spherical harmonics approximation can include real-valued moments of the radiance coefficients.

In third embodiments or any of the embodiments, the simplified spherical harmonics approximation can include complex-valued moments of the radiance coefficients.

In third embodiments or any of the embodiments, the simplified spherical harmonics algorithm is an $SP_3$ model.

In third embodiments or any of the embodiments, the system has less than or equal to 400 MB of RAM for use in solving the forward and inverse problems.

In fourth embodiments or any of the embodiments, a method for optical tomographic imaging of a sample can include reconstructing one or more images indicative of properties in the sample using a reconstruction algorithm employing a simplified spherical harmonic equation and a partial differential equation (PDE)-constrained algorithm.

In fourth embodiments or any of the embodiments, the PDE-constrained algorithm can be a sequential quadratic programming algorithm.

In fourth embodiments or any of the embodiments, said one or more images can be three-dimensional images.

In fourth embodiments or any of the embodiments, the one or more images can be of absorption and scattering coefficients in the sample.

In fourth embodiments or any of the embodiments, the reconstructing can be performed using multiple computing cores operating in parallel.

In fourth embodiments or any of the embodiments, the reconstructing can include minimizing a Lagrangian function.

In fourth embodiments or any of the embodiments, the simplified spherical harmonics equation can be a finite-volume frequency-domain SPN equation.

In fourth embodiments or any of the embodiments, the simplified spherical harmonics equation can be an $SP_3$ model.

In fourth embodiments or any of the embodiments, the sample can be a human hand, and the reconstructing can be performed using less than or equal to 400 MB of RAM and in less than one hour.

In fourth embodiments or any of the embodiments, the sample can be a human hand, the method can include interrogating fingers thereof with near infra-red radiation and detecting radiation emanating from the finger, the reconstructing can be based on the detected radiation, and the reconstructing can be completed less than one hour after the detecting.

In fourth embodiments or any of the embodiments, the one or more images can be of absorption and scattering coefficients in the sample, and the method can include classifying a status of the sample based at least in part on the reconstructed absorption and scattering coefficient images.

In fourth embodiments or any of the embodiments, the sample can be a finger of a living animal, and the classifying can be with respect to a presence of rheumatoid arthritis in said finger.

In fifth embodiments or any of the embodiments, a method for diagnosing a medical condition using diffuse optical tomographic imaging can include illuminating tissue of a patient with near-infrared photons and detecting at one or more detectors radiation emanating from the illuminated tissue; by an image processor, reconstructing maps of absorption and scattering coefficients in the tissue responsively to a simplified spherical harmonics (SPN) algorithm and a reduced-Hessian sequential quadratic programming (rSQP) partial differential equation (PDE)-constrained optimization; and by a classification processor, determining the presence of the medical condition in the patient responsively to the reconstructed absorption and scattering coefficient maps.

In fifth embodiments or any of the embodiments, the maps can be volumetric maps of absorption and scattering coefficients.

In fifth embodiments or any of the embodiments, the tissue can be a joint of the patient and the condition can be rheumatoid arthritis.

In fifth embodiments or any of the above embodiments, the condition can be an autoimmune disorder.

In fifth embodiments or any of the embodiments, the condition can be one of Systemic lupus erythematosus, Addison's disease, Celiac disease, Dermatomyositis, Graves disease, Hashimoto's thyroiditis, Multiple sclerosis, Myasthenia gravis, Pernicious anemia, Reactive arthritis, Rheumatoid arthritis, Sjogren syndrome, Systemic lupus erythematosus, and Type I diabetes.

In fifth embodiments or any of the embodiments, the tissue can be a joint of a finger of the patient, and the illuminating and detecting, the reconstructing, and the determining can be performed within one hour of each other.

In fifth embodiments or any of the embodiments, the image processor can include multiple computing cores operating in parallel to perform said reconstructing.

In fifth embodiments or any of the embodiments, the reconstructing can include minimizing a Lagrangian function.

In fifth embodiments or any of the embodiments, the simplified spherical harmonics algorithm can be an $SP_N$ model, with N being greater than or equal to 3.

In fifth embodiments or any of the embodiments, the tissue can be a joint of a finger of the patient, and the image processor can have 400 MB of RAM or less.

In fifth embodiments or any of the embodiments, the illuminating can include modulating the illuminating at a modulation frequency in a range of 200 MHz to 800 MHz.

In sixth embodiments or any of the embodiments, a system for generating an image can include an optical tomographic imaging transducer and a processor. The optical tomographic imaging transducer can have multiples sources and detectors configured to generate optical data from a target sample. The processor can be configured to receive the optical data and can be programmed to reconstruct data representing one or more three-dimensional images of absorption and scattering coefficients in the sample by solving forward and inverse scattering and absorption problems, further by using a partial differential equation (PDE)-constrained algorithm, and still further by employing simplified spherical harmonics to estimate light propagation in said target sample.

In sixth embodiments or any of the embodiments, the PDE-constrained algorithm can include a sequential quadratic programming algorithm.

In sixth embodiments or any of the embodiments, the target sample can be living tissue, for example, a human hand or finger thereof.

In sixth embodiments or any of the embodiments, the processor can include multiple computing cores, reconstructing can be performed using the multiple computing cores operating in parallel, and the processor can be programmed to decompose the solving forward and inverse scattering and absorption problems into sequential steps that can be computed in parallel. In sixth embodiments or any of the embodiments, the reconstructing can include minimizing a Lagrangian function.

In sixth embodiments or any of the embodiments, the simplified spherical harmonics can include a finite-volume frequency-domain SPN equation.

In sixth embodiments or any of the embodiments, the simplified spherical harmonics can be an $SP_3$ model.

In sixth embodiments or any of the embodiments, the sample can be a finger of a living animal, and the processor can be configured to reconstruct the data in less than one hour.

In seventh embodiments or any of the embodiments, a computer aided diagnostic system can include a data processor. The data processor can be configured to receive optical tomographic data representing interrogated tissues of a living animal and to estimate volumetric properties of the living animal from the receive optical tomographic data. The processor can be further configured to output display data and/or classification data representing said volumetric properties and/or classifying clinical features of said living animal and to execute instructions to estimate said properties using a method for performing a partial differential equation (PDE)-constrained reduced Hessian sequential quadratic programming (rSQP) optimization in which a constraint is defined by a simplified spherical harmonics approximation of the equation of radiative transfer.

In eighth embodiments or any of the embodiments, a computer aided diagnostic system can include a data storage system and a processor. The data storage system can be configured to receive optical tomographic data representing interrogated tissues of a living animal. The processor can be configured to retrieve said optical tomographic data from said data storage system and estimate volumetric properties of the living animal. The processor can be configured to output display data and/or classification data representing said volumetric properties and/or classifying clinical features of said living animal and to execute instructions to estimate said properties, the instructions embodying a method for performing a partial differential equation (PDE)-constrained optimization in which optical tomography inverse and forward problems are solved simultaneously and independently and wherein the forward problem is represented by spherical harmonics coefficients.

In seventh or eighth embodiments or any of the embodiments, the spatially distributed properties can include at least one of: volumetric absorption, volumetric scattering, volumetric fat distribution, volumetric distribution of oxygenated hemoglobin, and/or de-oxygenated hemoglobin, volumetric fluorophore concentration and/or distribution, and/or volumetric quantum yield.

In seventh or eighth embodiments or any of the embodiments, the PDE-constrained optimization can include minimizing a Lagrangian function.

In seventh or eighth embodiments or any of the embodiments, the processor can comprise multiple computing cores, and the processor can be configured to perform the PDE-constrained optimization in parallel using said multiple cores.

In seventh or eighth embodiments or any of the embodiments, the simplified spherical harmonics approximation can be a finite-volume frequency-domain SPN equation.

In seventh or eighth embodiments or any of the embodiments, the simplified spherical harmonics approximation can include only real-valued diffusion coefficients.

In seventh or eighth embodiments or any of the embodiments, diffusion-like coefficients of the simplified spherical harmonics approximation can be only real-valued.

In seventh or eighth embodiments or any of the embodiments, the spherical harmonics approximation can include complex-valued diffusion coefficients.

In seventh or eighth embodiments or any of the embodiments, diffusion-like coefficients of the simplified spherical harmonics approximation can be complex-valued.

In seventh or eighth embodiments or any of the embodiments, the simplified spherical harmonics approximation can include real-valued moments of radiance coefficients.

In seventh or eighth embodiments or any of the embodiments, the simplified spherical harmonics approximation can include complex-valued moments of radiance coefficients.

In seventh or eighth embodiments or any of the embodiments, the simplified spherical harmonics approximation can have a model order, N, greater than 1.

In seventh or eighth embodiments or any of the embodiments, the simplified spherical harmonics approximation can be an $SP_3$ model.

In any of the embodiments, the system can include at least 10 times less RAM than would otherwise be required when using an equation of radiative transfer (ERT).

In any of the embodiments, the method can use at least 10 times less RAM than would otherwise be required when using an equation of radiative transfer (ERT).

In any of the embodiments, a system can be perform any method disclosed herein. In any of the embodiments, a non-transitory computer-readable storage medium upon which is embodied a sequence of programmed instructions, and a computer processing system which executes the sequence of programmed instructions embodied on the computer-readable storage medium to cause the computer processing system to perform any of the methods disclosed herein.

It will be appreciated that the modules, processes, systems, and devices described above can be implemented in hardware, hardware programmed by software, software instruction stored on a non-transitory computer readable medium or a combination of the above. For example, a method for producing tomographic images by employing PDE-constrained spherical harmonics algorithms can be implemented, for example, using a processor configured to execute a sequence of programmed instructions stored on a non-transitory computer readable medium. For example, the processor can include, but is not limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and devices can be implemented as a single processor or as a distributed processor. Further, it should be appreciated that the steps mentioned herein may be performed on a single or distributed processor (single and/or multi-core). Also, the processes, modules, and sub-modules described in the various figures of and for embodiments herein may be distributed across multiple computers or systems or may be co-located in a single processor or system. Exemplary structural embodiment alternatives suitable for implementing the modules, systems, or processes described herein are provided below.

The modules, processes, systems, and devices described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the methods, processes, modules, devices, and systems (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the methods, systems, or a computer program products (software program stored on a non-transitory computer readable medium).

Furthermore, embodiments of the disclosed methods, processes, modules, devices, systems, and computer program product may be readily implemented, fully or partially, in software using, for example, object or object-oriented software development environments that provide portable source code that can be used on a variety of computer platforms. Alternatively, embodiments of the disclosed methods, processes, modules, devices, systems, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the methods, processes, modules, devices, systems, and computer program product can be implemented in hardware and/or software using any known or later developed systems or structures, devices and/or software by those of ordinary skill in the applicable art from the function description provided herein and with knowledge of tomography systems, imaging systems, and/or computer programming arts.

Furthermore, the foregoing descriptions apply, in some cases, to examples generated in a laboratory, but these examples can be extended to production techniques. Where quantities and techniques apply to the laboratory examples, they should not be understood as limiting. Features of the disclosed embodiments may be combined, rearranged, omitted, etc., within the scope of the invention to produce additional embodiments. Furthermore, certain features may sometimes be used to advantage without a corresponding use of other features.

It is thus apparent that there is provided in accordance with the present disclosure, system, methods, and devices for image reconstruction using combined PDE-constrained and simplified spherical harmonics algorithm. Many alternatives, modifications, and variations are enabled by the present disclosure. While specific embodiments have been shown and described in detail to illustrate the application of the principles of the present invention, it will be understood that the invention may be embodied otherwise without departing from such principles. Accordingly, Applicants intend to embrace all such alternatives, modifications, equivalents, and variations that are within the spirit and scope of the present invention.

The invention claimed is:

1. A computer aided diagnostic system, comprising:
a data storage configured to receive optical tomographic data representing interrogated tissues of a living animal;
a processor configured to retrieve said optical tomographic data from said data storage and estimate volumetric properties of the living animal,
said processor being further configured to output display data and/or classification data representing said volumetric properties and/or classifying clinical features of said living animal,
wherein the processor is configured to execute instructions to estimate said properties using a method for performing a partial differential equation (PDE)-constrained reduced Hessian sequential quadratic programming (rSQP) optimization in which a constraint is defined by a simplified spherical harmonics approximation of the equation of radiative transfer.

2. The system of claim 1, wherein the spatially distributed properties include at least one of: volumetric absorption, volumetric scattering, volumetric fat distribution, volumetric distribution of oxygenated hemoglobin, and/or de-oxygenated hemoglobin, volumetric fluorophore concentration and/or distribution, and/or volumetric quantum yield.

3. The system of claim 1, wherein the PDE-constrained optimization includes minimizing a Lagrangian function.

4. The system of claim 1, wherein the processor comprise multiple computing cores, the processor being configured to perform the PDE-constrained optimization in parallel using said multiple cores.

5. The system of claim 1, wherein the simplified spherical harmonics approximation includes a finite-volume frequency-domain SPN equation.

6. The system of claim 1, wherein the simplified spherical harmonics approximation is an $SP_3$ model.

7. The system of claim 1, wherein the processor is configured to use less than or equal to 400 MB of RAM in performing the PDE-constrained optimization.

8. The system of claim 1, further comprising a diffuse optical tomography (DOT) device coupled to the data storage for transmitting optical tomographic data thereto, the DOT device including at least one illumination source and at least one detector.

9. The system of claim 1, further comprising at least one illumination source configured to provide near-infrared radiation at a modulation frequency in a range of 200 MHz to 800 MHz.

10. The system of claim 1, further comprising a CCD camera or photodiodes connected to an optical fiber that detect radiation emanating from the interrogated tissue.

11. The system claim 1, wherein the processor is configured to classify clinical features of the living animal based at least in part on the estimated volumetric properties.

12. A computer aided diagnostic system, comprising:
a data processor configured to receive optical tomographic data representing interrogated tissues of a living animal;
the data processor being configured to estimate volumetric properties of the living animal from the receive optical tomographic data,
said processor being further configured to output display data and/or classification data representing said volumetric properties and/or classifying clinical features of said living animal,
wherein the processor is configured to execute instructions to estimate said properties using a method for performing a partial differential equation (PDE)-constrained reduced Hessian sequential quadratic programming (rSQP) optimization in which a constraint is defined by a simplified spherical harmonics approximation of the equation of radiative transfer.

13. The system of claim 12, wherein the spatially distributed properties include at least one of: volumetric absorption, volumetric scattering, volumetric fat distribution, volumetric distribution of oxygenated hemoglobin, and/or de-oxygenated hemoglobin, volumetric fluorophore concentration and/or distribution, and/or volumetric quantum yield.

14. The system of claim 12, wherein the PDE-constrained optimization includes minimizing a Lagrangian function.

15. The system of claim 12, wherein the processor comprise multiple computing cores, the processor being configured to perform the PDE-constrained optimization in parallel using said multiple cores.

16. The system of claim 12, wherein the simplified spherical harmonics approximation is a finite-volume frequency-domain SPN equation.

17. The system of claim 12, wherein the simplified spherical harmonics approximation is an $SP_3$ model.

* * * * *